(12) United States Patent
Reed et al.

(10) Patent No.: US 6,214,971 B1
(45) Date of Patent: Apr. 10, 2001

(54) **COMPOUNDS AND METHODS FOR THE DIAGNOSIS AND TREATMENT OF *BABESIA MICROTI* INFECTION**

(75) Inventors: Steven G. Reed, Bellevue; Michael J. Lodes, Seattle; Raymond Houghton, Bothell, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 08/990,571

(22) Filed: Dec. 11, 1997

Related U.S. Application Data

(63) Continuation-in-part of application No. 08/845,258, filed on Apr. 24, 1997, which is a continuation-in-part of application No. 08/723,142, filed on Oct. 1, 1996.

(51) Int. Cl.$^7$ .............................. C07K 1/00; C07K 14/00; C07K 17/00; C12P 21/04
(52) U.S. Cl. ...................... 530/350; 530/822; 435/69.7; 435/71.1; 435/7.1; 435/69.3; 424/185.1; 424/192.1; 424/190.1
(58) Field of Search ...................... 530/350, 822; 435/69.7, 71.1, 7.1, 69.3; 424/185.1, 192.1, 190.1

(56) References Cited

U.S. PATENT DOCUMENTS

| | | |
|---|---|---|
| 4,879,213 | 11/1989 | Fox et al. ................................ 435/5 |
| 5,171,685 | 12/1992 | McElwain et al. ............. 435/252.33 |
| 5,837,545 | * 11/1998 | Guy et al. ............................ 435/419 |

FOREIGN PATENT DOCUMENTS

WO 90/11776   10/1990   (WO).

OTHER PUBLICATIONS

Examination & Board Review, Medical Microbiology Immunology. Edited by Levinson et al, 1994.*
Rudinger et al in "Peptide Hormones", edited by Parson, University Park Press, Jun. 1976.*
J Cell Biol 111:2129–2138 Burgess et al., 1990.*
Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue", *The Journal of Cell Biology* 111:2129–2138, 1990.
Foglino et al., "Nucleotide sequence of the pepN gene encoding aminopeptidase N of *Escherichia coli,*" Gene 49: 303–309, 1986.
Lazar et al., "Transforming Growth Factor α: Mutation of Aspartic Acid 47 Leucine 48 Results in Different Biological Activities," *Molecular and Cellular Biology* 8(3): 1247–1252, 1988.
McCaman and Gabe, "The nucleotide sequence of the pepN gene and its over–expression in *Escherichia coli,*" Gene 48: 145–153, 1986.
Plotkin et al., Vaccines, W.B. Saunders Company, Philadelphia, 1988, Chapter 29, p. 571 ($2^{nd}$ full paragraph).
Tetzlaff et al., "Isolation and characterization of a gene associated with a virulent strain of *Babesia microti,*" *Molecular and Biochemical Parasitology* 40: 183–192, 1990.

* cited by examiner

*Primary Examiner*—Phuong T. Bui
*Assistant Examiner*—Li Lee
(74) *Attorney, Agent, or Firm*—Seed Intellectual Property Law Group PLLC

(57) ABSTRACT

Compounds and methods for the diagnosis and treatment of *Babesia microti* infection are disclosed. The compounds provided include polypeptides that contain at least one antigenic portion of a *B. microti* antigen and DNA sequences encoding such polypeptides. Antigenic epitopes of such antigens are also provided, together with pharmaceutical compositions and vaccines comprising such polypeptides, DNA sequences or antigenic epitopes. Diagnostic kits containing such polypeptides, DNA sequences or antigenic epitopes and a suitable detection reagent may be used for the detection of *B. microti* infection in patients and biological samples. Antibodies directed against such polypeptides and antigenic epitopes are also provided.

4 Claims, 9 Drawing Sheets

```
AACTAGATGCAGCACCACAATCACTACCACGTACCAATCATATACCAATAATGTACTAATAATGTACCAATAACTATGGTTTATAAAGATGGTGTCATTTAAATCAATATTAGTTCCTTATATTA   125

M  V  S  F  K  S  I  L  V  P  Y  I

CACTCTTTTTAATGAGCGGTGCTGTCTTTGCAAGTGATACCGATCCCGAAGCTGGTGGGCCTAGTGAAGCTGGTGGGCCTAGTGGAACTGTTGGGCCCAGTGAAGCTGGTGGGCCTAGTGAAGCT   250
                                                                   Repeat Sequences
 T  L  F  L  M  S  G  A  V  F  A  S  D  T  D  P  E  A  G  G  P  S  E  A  G  G  P  S  G  T  V  G  P  S  E  A  G  G  P  S  E  A GGTGGGCCTAGTGGAACTGGTTGGCCTAGTGAAGCTGGTGGGCCTAGTGAAGCTGGTGGGCCTAGTGAAGCTGGTGGGCCTAGTGAAGCTGGTGGGCCTAGTGGAACTGGTTGGCCTAGTGGAAC   375
                                                                   Repeat Sequences
 G  G  P  S  G  T  G  W  P  S  E  A  G  G  P  S  E  A  G  G  P  S  E  A  G  G  P  S  E  A  G  G  P  S  G  T  G  W  P  S  G  T TGGTTGGCCTAGTGAAGCTGGTTGGTCTAGTGAACGATTTGGATATCAGCTTCTTCCGTATTCTAGAAGAATAGTTATATTTAATGAAGTTTGTTTATCTTATATATACAAACATAGTGTTATGA   500
         Repeat Sequences
 G  W  P  S  E  A  G  W  S  S  E  R  F  G  Y  Q  L  L  P  Y  S  R  R  I  V  I  F  N  E  V  C  L  S  Y  I  Y  K  H  S  V  M TATTGGAACGAGATAGGGTGAACGATGGTCATAAAGACTACATTGAAGAAAAAACCAAGGAGAAGAATAAATTGAAAAAAGAATTGGAAAAATGTTTTCCTGAACAATATTCCCTTATGAAGAAA   625

I  L  E  R  D  R  V  N  D  G  H  K  D  Y  I  E  E  K  T  K  E  K  N  L  K  K  E  L  E  K  C  F  P  E  Q  Y  S  L  M  K  K

GAAGAATTGGCTAGAATATTTGATAATGCATCCACTATCTCTTCAAAATATAAGTTATTGGTTGATGAAATATCAAACAAGGCCTATGGTACATTGGAAGGTCCAGCTGCTGATAATTTTGACCA   750

E  E  L  A  R  I  F  D  N  A  S  T  I  S  S  K  Y  K  L  L  V  D  E  I  S  N  K  A  Y  G  T  L  E  G  P  A  A  D  N  F  D  H

TTTCCGTAATATATGGAAGTCTATTGTACTTAAAGATATGTTTATATATTGTGACTTATTATTACAACATTTAATCTATAAATTCTATTATGACAATACCGTTAATGATATCAAGAAAAATTTTG   875

F  R  N  I  W  K  S  I  V  L  K  D  M  F  I  Y  C  D  L  L  L  Q  H  L  I  Y  K  F  Y  Y  D  N  T  V  N  D  I  K  K  N  F

ACGAATCCAAATCTAAAGCTTTAGTTTTGAGGGATAAGATCACTAAAAAGGATGGAGATTATAACACTCATTTTGAGGACATGATTAAGGAGTTGAATAGTGCAGCAGAAGAATTTAATAAAATT  1000

D  E  S  K  S  K  A  L  V  L  R  D  K  I  T  K  K  D  G  D  Y  N  T  H  F  E  D  M  I  K  E  L  N  S  A  A  E  E  F  N  K  I

GTTGACATCATGATTTCCAACATTGGGGATTATGATGAGTATGACAGTATTGCAAGTTTCAAACCATTTCTTTCAATGATCACCGAAATCACTAAAATCACCAAAGTTTCTAATGTAATAATTCC  1125

V  D  I  M  I  S  N  I  G  D  Y  D  E  Y  D  S  I  A  S  F  K  P  F  L  S  M  I  T  E  I  T  K  I  T  K  V  S  N  V  I  I  P

TGGAATTAAGGCACTAACTTTAACCGTTTTTTTAATATTTATTACAAAATAGATGTAATACCAGATGTATACATTATTATATATTACAAAATTTACACATTATTTATGTATGAACGAACGAACAT  1250

```
CTCAGTCTTAAATGAAGAAATTGGGATAAATATGGAAATAGATTAAAGTAACATGAGAAAGATGAATATAATATTAGAATATGAAATTTAACAGAAATAAAATGAAGTAAAAGAGTGTATTTTGT    1375

AATAATTTATAATAAATTAGTATACAATGATTATATTACAGATGACTATTGATTATTGTATCAATTAAATATTGATTATTAATGATATCATATATGTATATGTTAATGATTGATTTGTTATACGT    1500

TGTGAATATGTTATATAATGACATACTATAATAATTAATATAATGTAGAGGATATTTTTTTTAATAGTATTTAATGAATATTATAGTTATAATTATAATAATGTAGATAAAAATGACATTAATTT    1625

GAATGTTTAAATTGAAATGTATGTAAAAATATGTATTTATAATCTGAATTGATTAATAATATAATATTCTACAATTAATTATTTTTGTAATTATAATAATTGATTATATTAATCTTTGAATTATT    1750

ATAAATAATATTATACTTCATTAAATTATTTCACATAAATTTCCAAATTATTATCCTTTATCTTAATGTTATCCAATTTTACACATCTTTCTTCATTACAATATTTTTTACTAATCCTGTATGC    1875

TCATATTCATATTCTTTAGAAATATAACGAAAATTAGATGTAACTTCGCCACTTACAAGTAAACTACCATCAATATAATAATAATGAATACCATTCATGTCCGTATATTCTTTATATTTTTTATC    2000

ATATTTTATTTTGTGATTATTCCATTCATTTGTATCATTATTCAATGAGAGAAATAATAGCAGAAAGATCCTTCTATAGAAACATAAAATTCAATTAATACTGGATTATTATGTTTGCAAGTATA    2125

GATGTTTAAATCAATAACACTACCAGTTGGTAATTTAGCATTGTCATCAAATTCAATTATATAATCAGAAATTTTGATTTTATCAATTTTATTCGGATGTGATAATTTATTTTGTTCTGATTCAT    2250

CGATCATGTATACAAATACTATTGTTAAAGGTTCCCTATCCTTATAATTAAAGTGGCCAATAAGATTGGCATTAATTACATTAGTAGTGTGTATTTGTAATAGTATCATTAGTGGTACTGACA    2375

GTTGTTATAGGTTTTGATTTCCATAATGAAACATCATTTTTATCTACACAATACA    2430
```

*Fig. 1B*

```
BI254     .......... ..AGDTDREA GGPSGTVGP. .......... ..........
BI1053    .......... ...GDTDREA GGPSGTVGP. .......... ..........
BI2227    .......... ..AGDTDREA GGPSGTVGP. .......... .SEAGGPSEA
BI2259    .......... ..AGDTDREA GGPSGTVGP. .......... .SEAGGPSEA
BI2253    .......... ........EA GGPSGTVGP. .......... .SEAGGPSEA
GRAC,S    .......... ...GDTDREA GGPSGTVGP. .....SEAGG PSEAGGPSEA
FISH,S    .......... ..AGDTDREA GGPSGTVGPS SAGGPSEAGG PSEAGGPSEA
MN1HAM    .......... ..AGDTDREA GGPSGTVGP. .......... .......SEA
MN2       .......... ..AGDTDREA GGPSGTVGP. .......... ..........
MN1PAT    .......... ..AGDTDREA GGPSGTVGP. .......... .......SEA
Bmni-6    YITLFLMSGA VFAGDTDREA GGPSGTVGP. .......... .......SEA
MN3       .......... ..AGDTDREA GGPSGTVGP. .......... .SEAGGPSEA
MR.T      .......... ..AGDTDREA GGPSGTVGP. .......... .SEAGGPSEA
          51                                                 100
BI254     ...SEAGGPS EAGGPSGTVG PSEAGGPSEA GGPSGTGWPS EAGGPSGTVG
BI1053    ...SEAGGPS EAGGPSGTVG PSEAGGPSEA GGPSGTGWPS EAGGPSGTVG
BI2227    GGPSEAGGPS EAGGPSEAGG PSEAGGPSEA GGPSEAGGPS EAGGPSEAGW
BI2259    GGPSEAGGPS EAGGPSEAGG PSEAGGPSEA GGPSEAGGPS EAGGPSEAGW
BI2253    GGPSEAGGPS EAGGPSEAGG PSEAGGPSEA GGPSEAGGPS EAGGPSEAGW
GRAC,S    GGPSEAGGPS EAGGPSEAGG PSEAGGPSEA GGPSEAGGPS EAGGPSEAGW
FISH,S    GGPSEAGGPS EAGGPSEAGG PSEAGGPSEA GGPSEAGGPS EAGGPSEAGW
MN1HAM    GGPSEAGGPS EAGGPSEAGG PSEAGGPSEA GGPSEAGGPS EAGGPSGTGW
MN2       ...SEAGGPS EAGGPSEAGG PSEAGGPSEA GGPSEAGGPS EAGGPSGTGW
MN1PAT    GGPSEAGGPS EAGGPSEAGG PSEAGGPSEA GGPSEAGGPS EAGGPSGTGW
Bmni-6    GGPSEAGGPS EAGGPSEAGG PSEAGGPSEA GGPSHAGGPS EAGGPSGTGW
MN3       GGPSEAGGPS EAGGPSEAGG PSEAGGPSEA GGPSEAGGPS EAGGPSGTGW
MR.T      GGPSEAGGPS EAGGPSEAGG PSEAGGPSEA GGPSEAGGPS EAGGPSGTGW
          101                                                150
BI254     PSEAGGP... .........S EAGGPSGTGW PSGTGWPSEV GWPSERFGYQ
BI1053    PSEAGGP... .........S EAGGPSGTGW PSGTGWPSEV GWPSERFGYQ
BI2227    PSEAGWPSEA GGPSGTGWPS EAGWPSEAGW PSEAGWPSEA GW........
BI2259    PSEAGWPSEA GGPSGTGWPS EAGWPSEAGW PSEAGWPSEA GWPSERFGYQ
BI2253    PSEAGWPSEA GGPSGTGWPS EAGWPSEAGW PSEAGWPSEA GWPSER....
GRAC,S    PSEAGWPSEA GGPSGTGWPS EAGWPSEAGW PSEAGWPSEA GWPSERFGYQ
FISH,S    PSEAGWPSEA GGPSGTGWPS EAGWPSEAGW PSEAGWPSEA GWPSERFGYQ
MN1HAM    PSEAGWP... .........S EAGWPSEAGW PSEAGWPSEA GWPSERFGYQ
MN2       PSEAGWP... .........S EAGWPSEAGW PSEAGWPSEA GW........
MN1PAT    PSEAGWP... .........S EAGWPSEAGW PSEAGWPSEA GWPSERFGYQ
Bmni-6    PSEAGWP... .........S EAGWPSEAGW PSEAGWPSEA GWPSERFGYQ
MN3       PSEAGWP... .........S EAGWPSEAGW PSEAGWPSEA GWPSERFGYQ
MR.T      PSEAGWP... .........S EAGWPSEAGW PSEAGWPSEA GWPSERFGYQ
```

*Fig. 6A*

```
           151              177
BI254    LLWYSRRIVI .......... .......
BI1053   LLWYSRRIVI .......... .......
BI2227   .......... .......... .......
BI2259   LLWYSRRIVI .......... .......
BI2253   .......... .......... .......
GRAC,S   LLWYS..... .......... .......
FISH,S   .......... .......... .......
MN1HAM   LLWYSRRIVI .......... .......
MN2      .......... .......... .......
MN1PAT   LLWYS..... .......... .......
Bmni-6   LLWYSRRIVI FNEIYLSHIY EHSVMIL
MN3      LLWYSR.... .......... .......
MR.T     LLWYSR.... .......... .......
```

COMPOUNDS AND METHODS FOR THE DIAGNOSIS AND TREATMENT OF *BABESIA MICROTI* INFECTION

CROSS-REFERENCE TO RELATED APPLICATIONS

This application is a continuation-in-part of U.S. application Ser. No. 08/845,258, filed Apr. 24, 1997, which is a continuation-in-part of U.S. application Ser. No. 08/723,142 filed Oct. 1, 1996.

TECHNICAL FIELD

The present invention relates generally to the detection of *Babesia microti* infection. In particular, the invention is related to polypeptides comprising a *B. microti* antigen, to antigenic epitopes of such an antigen and the use of such polypeptides and antigenic epitopes for the serodiagnosis and treatment of *B. microti* infection.

BACKGROUND OF THE INVENTION

Babesiosis is a malaria-like illness caused by the rodent parasite *Babesia microti* (*B. microti*) which is generally transmitted to humans by the same tick that is responsible for the transmission of Lyme disease and ehrlichiosis, thereby leading to the possibility of co-infection with babesiosis, Lyme disease and ehrlichiosis from a single tick bite. While the number of reported cases of *B. microti* infection in the United States is increasing rapidly, infection with *B. microti*, including co-infection with Lyme disease, often remains undetected for extended periods of time. Babesiosis is potentially fatal, particularly in the elderly and in patients with suppressed immune systems. Patients infected with both Lyme disease and babesiosis have more severe symptoms and prolonged illness compared to those with either infection alone.

The preferred treatments for Lyme disease, ehrlichiosis and babesiosis are different, with penicillins, such as doxycycline and amoxicillin, being most effective in treating Lyme disease, tetracycline being preferred for the treatment of ehrlichiosis, and anti-malarial drugs, such as quinine and clindamycin, being most effective in the treatment of babesiosis. Accurate and early diagnosis of *B. microti* infection is thus critical but methods currently employed for diagnosis are problematic.

All three tick-borne illnesses share the same flu-like symptoms of muscle aches, fever, headaches and fatigue, thus making clinical diagnosis difficult. Microscopic analysis of blood samples may provide false-negative results when patients are first seen in the clinic. Indirect fluorescent antibody staining methods for total immunoglobulins to *B. microti* may be used to diagnose babesiosis infection, but such methods are time-consuming and expensive. There thus remains a need in the art for improved methods for the detection of *B. microti* infection.

SUMMARY OF THE INVENTION

The present invention provides compositions and methods for the diagnosis and treatment of *B. microti* infection. In one aspect, polypeptides are provided comprising an immunogenic portion of a *B. microti* antigen, or a variant of such an antigen that differs only in conservative substitutions and/or modifications. In one embodiment, the antigen comprises an amino acid sequence encoded by a DNA sequence selected from the group consisting of (a) sequences recited in SEQ ID NO: 1–17, 37, 40, 42, 45, 50, 51 and 56–67; (b) the complements of said sequences; and (c) sequences that hybridize to a sequence of (a) or (b) under moderately stringent conditions.

In another aspect, the present invention provides an antigenic epitope of a *B. microti* antigen comprising the amino acid sequence -$X_1$-$X_2$-$X_3$-$X_4$-$X_5$-Ser- (SEQ ID NO: 35), wherein $X_1$ is Glu or Gly, $X_2$ is Ala or Thr, $X_3$ is Gly or Val, $X_4$ is Trp or Gly and $X_5$ is Pro or Ser. In one embodiment of this aspect, $X_1$ is Glu, $X_2$ is Ala and $X_3$ is Gly. In a second embodiment $X_1$ is Gly, $X_2$ is Thr and $X_5$ is Pro. The present invention further provides polypeptides comprising at least two of the above antigenic epitopes, the epitopes being contiguous.

In yet another aspect, the present invention provides an antigenic epitope of a *B. microti* antigen comprising an amino acid sequence selected from the group consisting of SEQ ID NO: 36 and 39, together with polypeptides comprising at least two such antigenic epitopes, the epitopes being contiguous.

In a related aspect, DNA sequences encoding the above polypeptides, recombinant expression vectors comprising these DNA sequence and host cells transformed or transfected with such expression vectors are also provided.

In another aspect, the present invention provides fusion proteins comprising either a first and a second inventive polypeptide, a first and a second inventive antigenic epitope, or, alternatively, an inventive polypeptide and an inventive antigenic epitope.

In further aspects of the subject invention, methods and diagnostic kits are provided for detecting *B. microti* infection in a patient. In one embodiment, the method comprises: (a) contacting a biological sample with at least one polypeptide comprising an immunogenic portion of a *B. microti* antigen; and (b) detecting in the sample the presence of antibodies that bind to the polypeptide, thereby detecting *B. microti* infection in the biological sample. In other embodiments, the methods comprise: (a) contacting a biological sample with at least one of the above polypeptides or antigenic epitopes; and (b) detecting in the sample the presence of antibodies that bind to the polypeptide or antigenic epitope. Suitable biological samples include whole blood, sputum, serum, plasma, saliva, cerebrospinal fluid and urine. The diagnostic kits comprise one or more of the above polypeptides or antigenic epitopes in combination with a detection reagent.

The present invention also provides methods for detecting *B. microti* infection comprising: (a) obtaining a biological sample from a patient; (b) contacting the sample with at least two oligonucleotide primers in a polymerase chain reaction, at least one of the oligonucleotide primers being specific for a DNA sequence encoding the above polypeptides; and (c) detecting in the sample a DNA sequence that amplifies in the presence of the first and second oligonucleotide primers. In one embodiment, the oligonucleotide primer comprises at least about 10 contiguous nucleotides of a DNA sequence encoding the above polypeptides.

In a further aspect, the present invention provides a method for detecting *B. microti* infection in a patient comprising: (a) obtaining a biological sample from the patient; (b) contacting the sample with an oligonucleotide probe specific for a DNA sequence encoding the above polypeptides; and (c) detecting in the sample a DNA sequence that hybridizes to the oligonucleotide probe. In one embodiment of this aspect, the oligonucleotide probe comprises at least about 15 contiguous nucleotides of a DNA sequence encoding the above polypeptides.

In yet another aspect, the present invention provides antibodies, both polyclonal and monoclonal, that bind to the polypeptides described above, as well as methods for their use in the detection of *B. microti* infection.

Within other aspects, the present invention provides pharmaceutical compositions that comprise one or more of the above polypeptides or antigenic epitopes, or a DNA molecule encoding such polypeptides, and a physiologically acceptable carrier. The invention also provides vaccines comprising one or more of the inventive polypeptides or antigenic epitopes and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above pharmaceutical compositions or vaccines.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 shows the genomic sequence of the *B. microti* antigen BMNI-3 (SEQ ID NO: 3) including a translation of the putative open reading frame (SEQ ID NO: 49). An internal six amino acid repeat sequence (SEQ ID NO: 35) is indicated by vertical lines within the open reading frame.

FIG. 6 shows an alignment of the repeat region of different homologues of the *B. microti* antigen BMNI-6, illustrating the geographic variation in the number and location of the repeats. The homologues correlate with the following SEQ ID Nos: BI254 (SEQ ID NO:68), BI1053 (SEQ ID NO:69), BI2227 (SEQ ID NO:70), BI2259 (SEQ ID NO:71), BI2253 (SEQ ID NO:72), GRAC, S (SEQ ID NO:73), FISH, S (SEQ ID NO:74), MNIHAM (SEQ ID NO:75), MN2 (SEQ ID NO:76), MNIPAT (SEQ ID NO:77), MN3 (SEQ ID NO:78), MR.T (SEQ ID NO:79), and Bmni-6 (SEQ ID NO:23).

DETAILED DESCRIPTION OF THE INVENTION

Figure 2A:
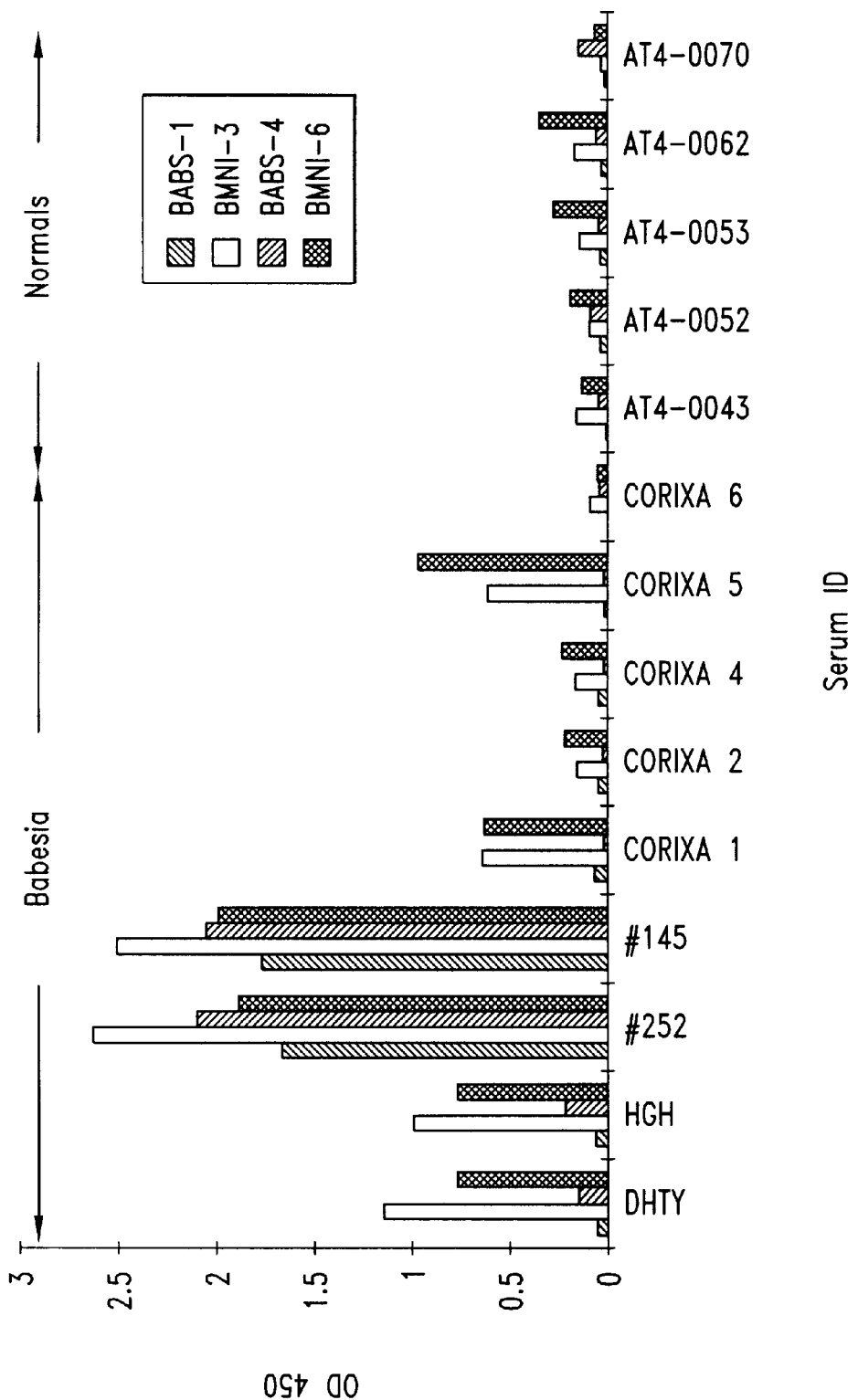
FIG. 2a shows the reactivity of the *B. microti* antigens BMNI-3 and BMNI-6, and the peptides BABS-1 and BABS-4 with sera from *B. microti*-infected individuals and from normal donors as determined by ELISA.
Figure 2B:
FIG. 2b shows the reactivity of the *B. microti* antigens BMNI-4 and BMNI-15 with sera from *B. microti*-infected individuals and from normal donors as determined by ELISA.
Figure 3:
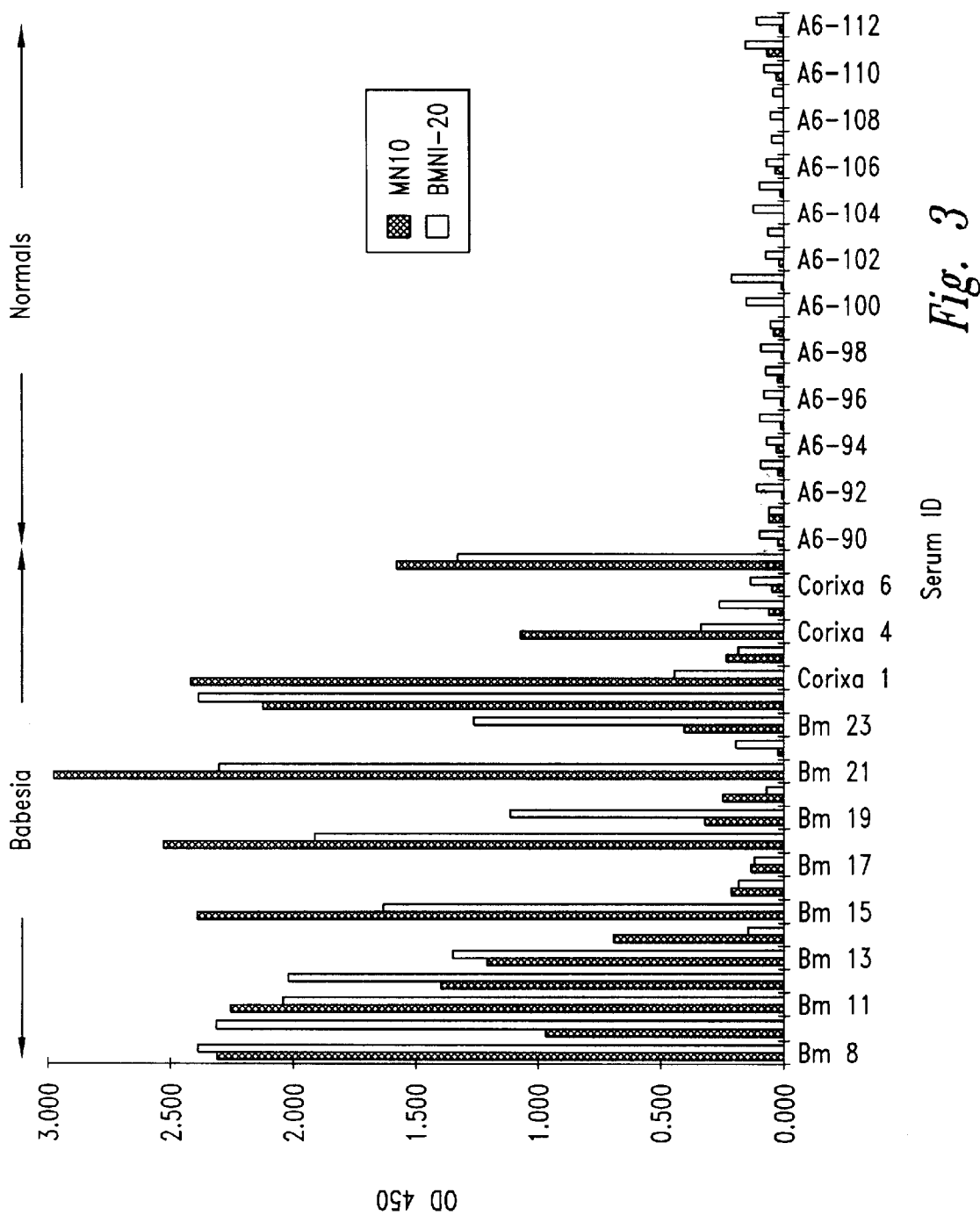
FIG. 3 shows the reactivity of the *B. microti* antigens MN-10 and BMNI-20 with sera from *B. microti*-infected patients and from normal donors as determined by ELISA.

As noted above, the present invention is generally directed to compositions and methods for the diagnosis and treatment of *B. microti* infection. In one aspect, the compositions of the subject invention include polypeptides that comprise at least one immunogenic portion of a *B. microti* antigen, or a variant of such an antigen that differs only in conservative substitutions and/or modifications.

As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *B. microti* antigen or may be heterologous, and such sequences may (but need not) be immunogenic.

An "immunogenic portion" of an antigen is a portion that is capable of reacting with sera obtained from a *B. microti*-infected individual (i.e., generates an absorbance reading with sera from infected individuals that is at least three standard deviations above the absorbance obtained with sera from uninfected individuals, in a representative ELISA assay described herein). Polypeptides comprising at least an immunogenic portion of one or more *B. microti* antigens as described herein may generally be used, alone or in combination, to detect *B. microti* in a patient.

The compositions and methods of this invention also encompass variants of the above polypeptides. A "variant," as used herein, is a polypeptide that differs from the native antigen only in conservative substitutions and/or modifications, such that the antigenic properties of the polypeptide are retained. Such variants may generally be identified by modifying one of the above polypeptide sequences, and evaluating the antigenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In specific embodiments, the subject invention discloses polypeptides comprising at least an immunogenic portion of a *B. microti* antigen (or a variant of such an antigen), that comprises one or more of the amino acid sequences encoded by (a) a DNA sequence selected from the group consisting of SEQ ID NO: 1–17, 37, 40, 42, 45 50, 51 and 56–67, (b) the complements of such DNA sequences or (c) DNA sequences substantially homologous to a sequence in (a) or (b).

The *B. microti* antigens provided by the present invention include variants that are encoded by DNA sequences which are substantially homologous to one or more of the DNA sequences specifically recited herein. "Substantial homology," as used herein, refers to DNA sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing DNA sequences are also within the scope of this invention, as are nucleotide sequences that, due to code degeneracy, encode an immunogenic polypeptide that is encoded by a hybridizing DNA sequence.

In general, B. microti antigens, and DNA sequences encoding such antigens, may be prepared using any of a variety of procedures. For example, DNA molecules encoding B. microti antigens may be isolated from a B. microti genomic or cDNA expression library by screening with sera from B. microti-infected individuals as described below in Example 1, and sequenced using techniques well known to those of skill in the art. DNA molecules encoding B. microti antigens may also be isolated by screening an appropriate B. microti expression library with anti-sera (e.g., rabbit) raised specifically against B. microti antigens.

Antigens may be induced from such clones and evaluated for a desired property, such as the ability to react with sera obtained from a B. microti-infected individual as described herein. Alternatively, antigens may be produced recombinantly, as described below, by inserting a DNA sequence that encodes the antigen into an expression vector and expressing the antigen in an appropriate host. Antigens may be partially sequenced using, for example, traditional Edman chemistry. See Edman and Berg, *Eur. J Biochem.* 80:116–132, 1967.

DNA sequences encoding antigens may also be obtained by screening an appropriate B. microti cDNA or genomic DNA library for DNA sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning: A Laboratory Manual*, Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions.

Immunogenic portions of B. microti antigens may be prepared and identified using well known techniques, such as those summarized in Paul, *Fundamental Immunology*, 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a B. microti antigen generates at least about 20%, and preferably about 100%, of the signal induced by the full length antigen in a model ELISA as described herein.

Portions and other variants of B. microti antigens may be generated by synthetic or recombinant means. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line, such as COS or CHO. The DNA sequences expressed in this manner may encode naturally occurring antigens, portions of naturally occurring antigens, or other variants thereof.

In another aspect, the present invention provides epitope repeat sequences, or antigenic epitopes, of a B. microti antigen, together with polypeptides comprising at least two such contiguous antigenic epitopes. As used herein an "epitope" is a portion of an antigen that reacts with sera from B. microti-infected individuals (i.e. an epitope is specifically bound by one or more antibodies present in such sera). As discussed above, epitopes of the antigens described in the present application may be generally identified using techniques well known to those of skill in the art.

In one embodiment, antigenic epitopes of the present invention comprise the amino acid sequence $-X_1-X_2-X_3-X_4-X_5$-Ser- (SEQ ID NO: 35), wherein $X_1$ is Glu or Gly, $X_2$ is Ala or Thr, $X_3$ is Gly or Val, $X_4$ is Trp or Gly, and $X_5$ is Pro or Ser. In another embodiment, the antigenic epitopes of the present invention comprise an amino acid sequence selected from the group consisting of SEQ ID NO: 36 and 39. As discussed in more detail below, antigenic epitopes provided herein may be employed in the diagnosis and treatment of B. microti infection, either alone or in combination with other B. microti antigens or antigenic epitopes. Antigenic epitopes and polypeptides comprising such epitopes may be prepared by synthetic means, as described generally above and in detail in Example 2.

In general, regardless of the method of preparation, the polypeptides and antigenic epitopes disclosed herein are prepared in substantially pure form. Preferably, the polypeptides and antigenic epitopes are at least about 80% pure, more preferably at least about 90% pure and most preferably at least about 99% pure.

In a further aspect, the present invention provides fusion proteins comprising either a first and a second inventive polypeptide, a first and a second inventive antigenic epitope or an inventive polypeptide and an antigenic epitope of the present invention, together with variants of such fusion proteins. The fusion proteins of the present invention may also include a linker peptide between the polypeptides or antigenic epitopes.

A DNA sequence encoding a fusion protein of the present invention is constructed using known recombinant DNA techniques to assemble separate DNA sequences encoding, for example, the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric hindrance.

In another aspect, the present invention provides methods for using polypeptides comprising an immunogenic portion of a *B. microti* antigen and the antigenic epitopes described above to diagnose babesiosis. In this aspect, methods are provided for detecting *B. microti* infection in a biological sample, using one or more of the above polypeptides and antigenic epitopes, alone or in combination. For clarity, the term "polypeptide" will be used when describing specific embodiments of the inventive diagnostic methods. However, it will be clear to one of skill in the art that the antigenic epitopes of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to *B. microti* antigens which may be indicative of babesiosis.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by to using each polypeptide individually to evaluate serum samples obtained from a series of patients known to be infected with *B. microti*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within a *B. microti*-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween $_{20}$™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-*B. microti* antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for babesiosis. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. Briefly, in this embodiment, the cut-off value may be determined from a plot of pairs of true positive rates (ie., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for babesiosis.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*B. microti* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 pg, and more preferably from about 50 ng to about 500 ng. Such tests can typically be performed with a very small amount (e.g., one drop) of patient serum or blood.

Of course, numerous other assay protocols exist that are suitable for use with the polypeptides and antigenic epitopes of the present invention. The above descriptions are intended to be exemplary only.

In yet another aspect, the present invention provides antibodies to the polypeptides and antigenic epitopes of the present invention. Antibodies may be prepared by any of a variety of techniques known to those of ordinary skill in the art. See, e.g., Harlow and Lane, *Antibodies: A Laboratory Manual*, Cold Spring Harbor Laboratory, Cold Spring Harbor, N.Y., 1988. In one such technique, an immunogen comprising the antigenic polypeptide or epitope is initially injected into any of a wide variety of mammals (e.g., mice, rats, rabbits, sheep and goats). The polypeptides and antigenic epitopes of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide or antigenic epitope may then be purified from such antisera by, for example, affinity chromatography using the polypeptide or antigenic epitope coupled to a suitable solid support.

Monoclonal antibodies specific for the antigenic polypeptide or epitope of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide or antigenic epitope of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide or antigenic epitope. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides or antigenic epitopes of this invention may be used in the purification process in, for example, an affinity chromatography step.

Antibodies may be used in diagnostic tests to detect the presence of *B. microti* antigens using assays similar to those detailed above and other techniques well known to those of skill in the art, thereby providing a method for detecting *B. microti* infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *B. microti*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect *B. microti*-specific sequences in biological samples, preferably sputum, blood, serum, saliva, cerebrospinal fluid or urine. DNA probes or primers comprising oligonucleotide sequences described above may be used alone or in combination with each other.

In another aspect, the present invention provides methods for using one or more of the above polypeptides, antigenic epitopes or fusion proteins (or DNA molecules encoding such polypeptides) to induce protective immunity against *B. microti* infection in a patient. As used herein, a "patient" refers to any warm-blooded animal, preferably a human. A patient may be afflicted with a disease, or may be free of detectable disease and/or infection. In other words, protective immunity may be induced to prevent or treat babesiosis.

In this aspect, the polypeptide, antigenic epitope, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *B. microti* antigens, either incorporated into a combination polypeptide or present within a separate polypeptide.

Alternatively, a vaccine may contain DNA encoding one or more polypeptides, antigenic epitopes or fusion proteins as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known B. microti antigen. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *B. microti* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

The following Examples are offered by way of illustration and not by way of limitation.

EXAMPLE 1

ISOLATION OF DNA SEQUENCES ENCODING *B. microti* ANTIGENS

This example illustrates the preparation of DNA sequences encoding *B. microti* antigens by screening a *B. microti* expression library with sera obtained from patients infected with *B. microti*.

*B. microti* genomic DNA was isolated from infected hamsters and sheared by sonication. The resulting randomly sheared DNA was used to construct a *B. microti* genomic expression library (approximately 0.5–4.0 kbp inserts) with EcoRI adaptors and a Lambda ZAP II/EcoRI/CIAP vector (Stratagene, La Jolla, Calif.). The unamplified library ($1.2\times10^6$/ml) was screened with an *E. coli* lysate-absorbed *B. microti* patient serum pool, as described in Sambrook et al., *Molecular Cloning: A Laboratory Manual*, Cold Spring Harbor Laboratories, Cold Spring Harbor, N.Y., 1989. Positive plaques were visualized and purified with goat-anti-human alkaline phosphatase. Phagemid from the plaques was rescued and DNA sequence for positive clones was obtained using forward, reverse, and specific internal primers on a Perkin Elmer/Applied Biosystems Inc. Automated Sequencer Model 373A (Foster City, Calif.).

Seventeen antigens (hereinafter referred to as BMNI-1-BMNI- 17) were purified and three were possibly redundant. The determined DNA sequences for BMNI-1-BMNI-17 are shown in SEQ ID NO: 1–17, respectively. The deduced amino acid sequences for BMNI-1-BMNI-6, BMNI-8 and BMNI-10-BMNI-17 are shown in SEQ ID NO: 18–32, respectively, with the predicted 5' and 3' protein sequences for BMNI-9 being shown in SEQ ID NO: 33 and 34, respectively.

The isolated DNA sequences were compared to known sequences in the gene bank using the DNA STAR system. Nine of the seventeen antigens (BMNI-1, BMNI-2, BMNI-3, BMNI-5, BMNI-6, BMNI-7, BMNI-12, BMNI-13 and BMNI-16) share some homology, with BMNI-1 and BMNI-16 being partial clones of BMNI-3. All of these nine antigens contain a degenerate repeat of six amino acids (SEQ ID NO: 35), with between nine to twenty-two repeats occurring in each antigen. The repeat portion of the sequences was found to bear some similarity to a *Plasmodium falciparum* merozoite surface antigen (MSA-2 gene). FIG. 1 shows the genomic sequence of BMNI-3 including a translation of the putative open reading frame, with the internal six amino acid repeat sequence being indicated by vertical lines within the open reading frame.

A second group of five antigens bear some homology to each other but do not show homology to any previously identified sequences (BMNI-4, BMNI-8, BMNI-9, BMNI-10 and BMNI- 11). These antigens may belong to a family of genes or may represent parts of a repetitive sequence. BMNI-17 contains a novel degenerate repeat of 32 amino acids (SEQ ID NO: 36). Similarly, the reverse complement of BMNI-17 (SEQ ID NO: 37) contains an open reading frame that encodes an amino acid sequence (SEQ ID NO: 38) having a degenerate 32 amino acid repeat (SEQ ID NO: 39).

The reverse complement of BMNI-3 (SEQ ID NO: 40) has an open reading frame which shows homology with the BMNI-4-like genes. The predicted amino acid sequence encoded by this open reading frame is shown in SEQ ID NO: 41. The reverse complement of BMNI-5 (SEQ ID NO: 42) contains a partial copy of a BMNI-3-like sequence and also an open reading frame with some homology to two yeast genes (*S. cerevisiae* G9365 ORF gene, and *S. cerevisiae* accession no. U18922). The predicted 5' and 3' amino acid sequences encoded by this open reading frame are shown in SEQ ID NO: 43 and 44, respectively. The reverse complement of BMNI-7 (SEQ ID NO: 45) contains an open reading frame encoding the amino acid sequence shown in SEQ ID NO: 46.

A telomeric repeat sequence, which is conserved over a wide range of organisms, was found in five antigens (BMNI-2, BMNI-5, BMNI-6, BMNI-7 and BMNI-16), indicating that many of the isolated genes may have a telomere-proximal location in the genome. BMNI-10 appears to include a double insert, the 3'-most segment having some homology to *E. coli* aminopeptidase N. In addition, BMNI-7 contains apparently random insertions of hamster DNA. One such insertion has characteristics of a transposible element (i.e. poly A tail and flanked by a direct repeat).

In subsequent studies, two additional *B. microti* antigens were isolated by screening the *B. microti* genomic DNA expression library described above with a serum pool from *B. microti* infected patients that showed low reactivity with recombinant proteins generated from clones BMNI-2-BMNI-17. The determined DNA sequences for these two clones, hereinafter referred to as MN-10 and BMNI-20, are provided in SEQ ID NO: 50 and 51, respectively, with the corresponding predicted amino acid sequences being provided in SEQ ID NO: 52 and 53. MN-10 was found to extend the sequence of BMNI-4 in the 3' direction and BMNI-20 was found to extend the sequence of BMNI-17 in the 5' direction.

EXAMPLE 2

SYNTHESIS OF SYNTHETIC POLYPEPTIDES

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

This procedure was used to synthesize two peptides (hereinafter referred to as BABS-1 and BABS-4) made to the repeat region of the isolated *B. microti* antigen BMNI-3. The sequences of BABS-1 and BABS-4 are shown in SEQ ID NO: 47 and 48, respectively.

EXAMPLE 3

USE OF REPRESENTATIVE ANTIGENS AND PEPTIDES FOR SERODIAGNOSIS OF *B. microti* INFECTION A. Diagnostic Properties of Representative Antigens and Peptides as Determined by ELISA The diagnostic properties of recombinant BMNI-3, BMNI-4, BMNI-6, BMNI-15, MN-10 and BMNI-20, and the BABS-1 and BABS-4 peptides were determined as follows.

Assays were performed in 96 well plates coated overnight at 4° C. with 200 ng antigen/well added in 50 μl of carbonate coating buffer. The plate contents were then removed and the wells were blocked for 2 hours with 200 μl of PBS/1% BSA. After the blocking step, the wells were washed six times with PBS/0.1% Tween 20™. Fifty microliters of sera, diluted 1:100 in PBS/0.1% Tween 20™/0.1% BSA, was then added to each well and incubated for 30 minutes at room temperature. The plates were then washed six times with PBS/0. 1% Tween 20™.

The enzyme conjugate (horseradish peroxidase-Protein A, Zymed, San Francisco, Calif.) was then diluted 1:20,000 in PBS/0.1% Tween 20™/0.1% BSA, and 50 μl of the diluted conjugate was added to each well and incubated for 30 minutes at room temperature. Following incubation, the wells were washed six times with PBS/0.1% Tween 20™. 100 μl of tetramethylbenzidine peroxidase substrate (Kirkegaard and Perry Laboratories, Gaithersburg, Md.) was added, undiluted, and incubated for 15 minutes. The reaction was stopped by the addition of 100 μl of 1N $H_2SO_4$ to each well and the plates were read at 450 nm.

FIG. 2*a* shows the reactivity of the recombinant BMNI-3 and BMNI-6 antigens and the two peptides BABS-1 and BABS-4 in the ELISA assay. The recombinant antigens and the two peptides were negative in ELISA with all seven samples from normal (*B. microti* negative) individuals. In contrast, both BMNI-3 and BMNI-6 detected six of the nine *B. microti*-infected samples, as compared to two out of the nine for the BABS-1 and BABS-4 peptides. This would suggest that BMNI-3 and BMNI-6 may contain other antigenic epitopes in addition to those present in the repeat epitopes in BABS-1 and BABS-4, or that an insufficient number of repeats are available in the peptides to fully express the antigenic epitopes present in the recombinant antigens BMNI-3 and BMNI-6.

FIG. 2*b* shows the ELISA reactivity of the recombinant antigens BMNI-4 and BMNI-15. Both recombinants were negative with all fifteen samples from normal individuals. BMNI-4 detected four out of nine *B. microti*-infected samples and BMNI-15 detected six out of nine *B. microti*-infected samples. Both BMNI-4 and BMNI-15 detected a *B. microti*-infected sample which was not detected by BMNI-3 or BMNI-6, suggesting that BMNI-4 and BMNI-15 might be complementary to BMNI-3 and BMNI-6 in the ELISA test described herein.

The ELISA reactivity of recombinant MN-10 and BMNI-20 with sera from *B. microti*-infected patients and from normal donors is shown in FIG. 3. MN-10 and BMNI-20 were found to be reactive with *B. microti*-infected sera that were not reactive with recombinant BMNI-2 through BMNI-17. Therefore, MN-10 and BMNI-20 may be usefully employed in combination with other *B. microti* antigens of the present invention for the detection of *B. microti* infection.

B. Diagnostic Properties of Representative Antigens and Peptides as Determined by Western Analysis Western blot analyses were performed on representative *B. microti* antigens as follows.

Antigens were induced as pBluescript SK- constructs (Stratagene), with 2 mM IPTG for three hours (T3), after which the resulting proteins from time 0 (T0) and T3 were separated by SDS-PAGE on 15% gels. Separated proteins were then transferred to nitrocellulose and blocked for 1 hr in 0.1% Tween 20™/PBS. Blots were then washed 3 times in 0.1% Tween 20™/PBS and incubated with a *B. microti* patient serum pool (1:200) for a period of 2 hours. After washing blots in 0.1% Tween 20™/PBS 3 times, immunocomplexes were detected by the addition of Protein A conjugated to $^{125}$I (1/25000; NEN-Dupont, Billerica, Mass.) followed by exposure to X-ray film (Kodak XAR 5; Eastman Kodak Co., Rochester, N.Y.) at −70° C. for 1 day.

Figure 4:
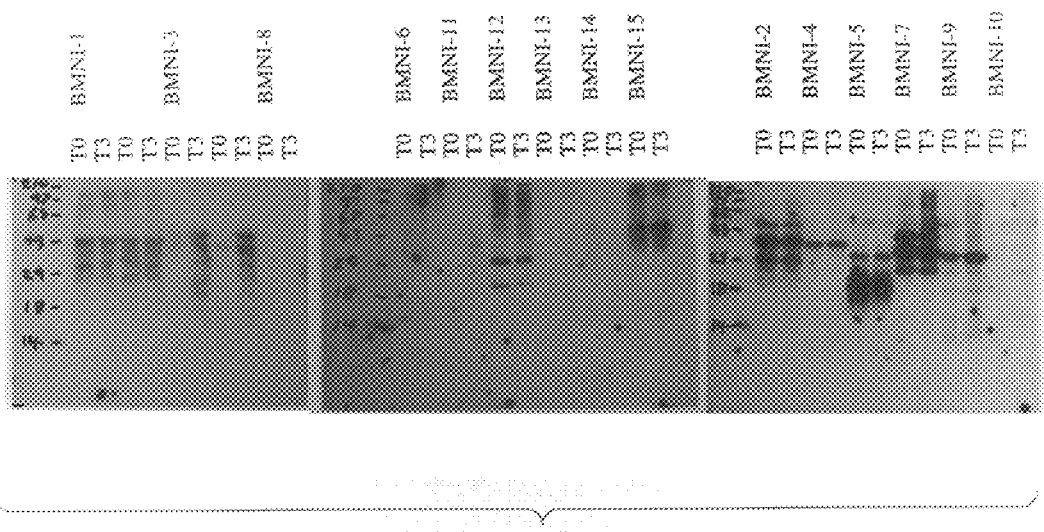
FIG. 4 shows the results of Western blot analysis of representative *B. microti* antigens of the present invention.

As shown in FIG. 4, resulting bands of reactivity with serum antibody were seen at 43 kDa for BMNI-1, 38 kDa for BMNI-2, 45 kDa for BMNI-3, 37 kDa for BMNI-4, 18 and 20 kDa for BMNI-5, 35 and 43 kDa for BMNI-7, 32 kDa for BMNI-9, 38 kDa for BMNI-11, 30 kDa for BMNI-12, 45 kDa for BMNI-15, and 43 kDa for BMNI-17 (not shown). Antigen BMNI-6, after reengineering as a pET 17b construct (Novagen, Madison, Wis.) showed a band of reactivity at 33 kDa (data not shown). Protein size standards, in kDa (Gibco BRL, Gaithersburg, MB), are shown to the left of the blots.

Western blots were performed on purified BMNI-3 recombinant antigen with a series of patient sera from *B. microti* patients and from patients with either Lyme disease or ehrlichiosis. Specifically, purified BMNI-3 (4 µg) was separated by SDS-PAGE on 12% gels. Protein was then transferred to nitrocellulose membrane for immunoblot analysis. The membrane was first blocked with PBS containing 1% Tween 20™ for 2 hours. Membranes were then cut into strips and incubated with individual sera (1/500) for two hours. The strips were washed 3 times in PBS/0.1% Tween 20™ containing 0.5 M NaCl prior to incubating with Protein A-horseradish peroxidase conjugate (1/20,000) in PBS/0.1% Tween 20™/0.5 M NaCl for 45 minutes. After further washing three times in PBS/0.1% Tween 20™/0.5 M NaCl, ECL chemiluminescent substrate (Amersham, Arlington Heights, Ill.) was added for 1 min. Strips were then reassembled and exposed to Hyperfilm ECL (Amersham) for 5–30 seconds.

Figure 5:
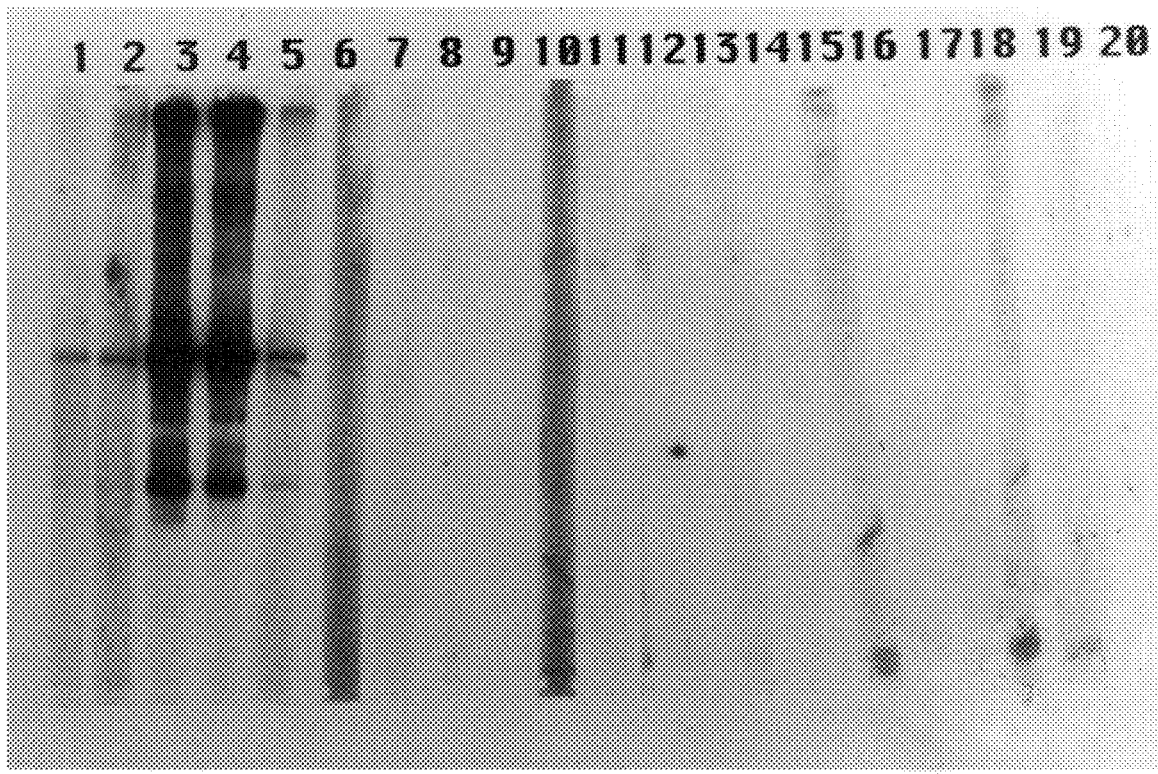
FIG. 5 shows the reactivity of purified recombinant *B. microti* antigen BMNI-3 with sera from *B. microti*-infected patients, Lyme disease-infected patients, ehrlichiosis-infected patients and normal donors as determined by Western blot analysis.

Lanes 1–9 of FIG. 5 show the reactivity of purified recombinant BMNI-3 with sera from nine *B. microti*-infected patients, of which five were clearly positive and a further two were low positives detectable at higher exposure to the hyperfilm ECL. This correlates with the reactivity as determined by ELISA. In contrast, no immunoreactivity was seen with sera from patients with either ehrlichiosis (lanes 10 and 11) or Lyme disease (lanes 12–14), or with sera from normal individuals (lanes 15–20). A major reactive band appeared at 45 kDa and a small break down band was seen at approximately 25 kDa.

EXAMPLE 4

The reactivity of the inventive antigens with sera from *B. microti* patients, as determined by Western blot, was found to vary with the U.S. location of the patients. Accordingly, geographic variation within the gene encoding the exemplary antigen BMNI-6 was examined as follows.

Two PCR primers, referred to as BMNI-6/5' and BMNI-6/3' (SEQ ID NOS: 54 and 55, respectively) were designed based on the region flanking the six amino acid degenerate repeat region of BMNI-6 (SEQ ID NO: 6). These primers were employed to amplify genomic DNA from whole blood obtained from twelve *B. microti*-infected patients and genomic DNA from whole blood from *P. leucopus* and hamsters in a Perkin Elmer 480 thermal cycler using the manufacturer's protocol. PCR products were evaluated for size on 2% agarose gels and then Southern blotted and probed with a DIG-labeled oligonucleotide. Positive clones were sequenced using an Applied Biosystems Model 373A or 377 sequencer. RT-PCR was performed on Trizol LS extracted *B. microti*-infected hamster whole blood RNA using the primers described above, and the resulting clones were sequenced as described above.

These studies resulted in the isolation of twelve BMNI-6 homologues, referred to hereinafter as BI254, BI1053, BI2227, BI2259, BI2253, BI2018, RIFS, MN1HAM, MN2, MN1PAT, MN3 and MRT with MN1HAM being obtained from hamster and the other eleven from patients. The determined DNA sequences of these clones are provided in SEQ ID NO: 56–67, respectively, with the corresponding predicted amino acid sequences being provided in SEQ ID NO: 68–79, respectively. Isolates from hamsters had the same sequences as found in the corresponding human blood, suggesting that genetic variation of BMNI-6 does not occur during passage. However, clones from different patients often showed variation in the number and location of the degenerate repeat found within BMNI-6. An alignment of the repeat regions from each of the twelve clones is provided in FIG. 6. Furthermore, strains that were closely related geographically were also closely related at the sequence level. For example, three patients from Nantucket Island, Mass., harbored clones (BI2253, BI2259 and BI2227) that were indistinguishable from each other but distinct from those found in other northeastern or upper midwestern strains. These results suggest that considerable antigenic diversity exists among isolates of *B. microti* from the U.S. and that geographic clustering of subtypes exists.

Although the present invention has been described in some detail by way of illustration and example for purposes of clarity of understanding, changes and modifications can be carried out without departing from the scope of the invention which is intended to be limited only by the scope of the appended claims.

SEQUENCE LISTING (1) GENERAL INFORMATION:

(iii) NUMBER OF SEQUENCES: 79

(2) INFORMATION FOR SEQ ID NO:1:

(i) SEQUENCE CHARACTERISTICS:
       (A) LENGTH: 792 base pairs
       (B) TYPE: nucleic acid
       (C) STRANDEDNESS: single
       (D) TOPOLOGY: linear (xi) SEQUENCE DESCRIPTION: SEQ ID NO:1:

```
CACTCTTTTT AATGAGCGGT GCTGTCTTTG CAAGTGATAC CGATCCCGAA GCTGGTGGGC     60

CTAGTGAAGC TGGTGGGCCT AGTGGAACTG TTGGGCCCAG TGAAGCTGGT GGGCCTAGTG    120

AAGCTGGTGG GCCTAGTGGA ACTGGTTGGC CTAGTGAAGC TGGTGGGCCT AGTGAAGCTG    180

GTGGGCCTAG TGAAGCTGGT GGGCCTAGTG AAGCTGGTGG GCCTAGTGGA ACTGGTTGGC    240

CTAGTGGAAC TGGTTGGCCT AGTGAAGCTG GTTGGTCTAG TGAACGATTT GGATATCAGC    300

TTCTTCCGTA TTCTAGAAGA ATAGTTATAT TTAATGAAGT TTGTTTATCT TATATATACA    360

AACATAGTGT TATGATATTG GAACGAGATA GGGTGAACGA TGGTCATAAA GACTACATTG    420

AAGAAAAAAC CAAGGAGAAG AATAAATTGA AAAAAGAATT GGAAAAATGT TTTCCTGAAC    480

AATATTCCCT TATGAAGAAA GAAGAATTGG CTAGAATATT TGATAATGCA TCCACTATCT    540

CTTCAAAATA TAAGTTATTG GTTGATGAAA TATCAAACAA GGCCTATGGT ACATTGGAAG    600

GTCCAGCTGC TGATAATTTT GACCATTTCC GTAATATATG GAAGTCTATT GTACTTAAAG    660

ATATGTTTAT ATATTGTGAC TTATTATTAC AACATTTAAT CTATAAATTC TATTATGACA    720

ATACCGTTAA TGATATCAAG AAAAATTTTG ACGAATCCAA ATCTAAAGCT TTAGTTTTGA    780

GGGATAAGAT CA                                                        792
```

(2) INFORMATION FOR SEQ ID NO:2:

(i) SEQUENCE CHARACTERISTICS:
       (A) LENGTH: 2732 base pairs
       (B) TYPE: nucleic acid
       (C) STRANDEDNESS: single
       (D) TOPOLOGY: linear (xi) SEQUENCE DESCRIPTION: SEQ ID NO:2:

```
AAACCCTAAA CCCTAAACCC TAAACCCTAA ACCCTAAACC CCTAAACCCT AAACCCTAAA     60

CCCTAAACCC TAAACCCTAA AACCCTAAAC CCTAAACCCT AAACCCTAAA CCCTAAACCC    120

TAAACCCTAA ACCCTAAACC CTAAACCCTA AACCCTAAAC CCTAAACCCT AAACCCTAAA    180

CCCTAAACCC TAAACCCTAA ACCCTAAACC CTAAACCCCT AAACCCTAAA CCCTAAACCC    240

TAAACCCTAA ACCCTAAACC CTAAACCCTA AACCCTAAAC CCTAAACCCT AAACCCTAAA    300

CCCTAAACCC TAAACCCTAA ACCCTAAACC CTAAAACCCT AAACCCTAAA CCCTAAACCC    360

TAAACCCTAA ACCCTAAACC CTAAACCCT AAACCCTAAA CCCTAAACCC TAAACCCTAA     420

ACCCCTAAAC CCTAAACCCC TAAACCCTAA ACCCTAAACC CTAAACCCTA AACCCTAAAC    480

CCTAAACCCT AAACCCTAAA CCCTAAACCC TAAACCCCTA AACCCTAAAC CCTAAACCCT    540

AAACCCTAAA CCCTAAACCC TAAACCCTAA ACCCTAACCC TAACCCTAAC CCTAACCCTA    600

ACCTAGCCTT CATTGACGTC TATCCCCAAT CTTAGAAAAA TCTTCAAATC GATTCTAGAA    660
```

```
TAACTGGAAA CAATTATCAG AAATTGTATA ACTGCTTATT AGCTTATTAG CTTATTAGTT    720

AGGATGTATG CACATTGATG ACAACTAGAT GCAGCACCAC AATCACTACC ACGTACCAAT    780

CATATACCAA TAATGTACTA ATAATGTACC AATAACTATG GTTTATAAAG ATGGTGTCAT    840

TTAAATCAAT ATTAGTTCCT TATATTACAC TCTTTTTAAT GAGCGGTGCT GTCTTTGCAA    900

GTGATACCGA TCCCGAAGCT GGTGGGCCTA GTGAAGCTGG TGGGCCTAGT GGAACTGTTG    960

GGCCCAGTGA AGCTGGTGGG CCTAGTGAAG CTGGTGGGCC TAGTGGAACT GTTGGGCCCA   1020

GTGAAGCTGG TGGGCCTAGT GAAGCTGGTG GGCCTAGTGG AACTGGTTGG CCTAGTGAAG   1080

CTGGTGGGCC TAGTGAAGCT GGTGGGCCTA GTGGAACTGT TGGGCCCAGT GAAGCTGGTG   1140

GGCCTAGTGA AGCTGGTGGG CCTAGTGAA CTGGTTGGCC TAGTGAAGCT GGTGGGCCTA   1200

GTGAAGCTGG TGGGCCTAGT GAAGCTGGTG GCCTAGTGA AGCTGGTGGG CCTAGTGGAA   1260

CTGGTTGGCC TAGTGGAACT GGTTGGCCTA GTGAAGCTGG TTGGTCTAGT GAACGATTTG   1320

GATATCAGCT TCTTCCGTAT TCTAGAAGAA TAGTTATATT TAATGAAGTT TGTTTATCTT   1380

ATATATACAA ACATAGTGTT ATGATATTGG AACGAGATAG GGTGAACGAT GGTCATAAAG   1440

ACTACATTGA AGAAAAAACC AAGGAGAAGA ATAAATTGAA AAAGAATTG GAAAAATGTT   1500

TTCCTGAACA ATATTCCCTT ATGAAGAAAG AAGAATTGGC TAGAATATTT GATAATGCAT   1560

CCACTATCTC TTCAAAATAT AAGTTATTGG TTGATGAAAT ATCAAACAAG GCCTATGGTA   1620

CATTGGAAGG TCCAGCTGCT GATAATTTTG ACCATTTCCG TAATATATGG AAGTCTATTG   1680

TACTTAAAGA TATGTTTATA TATTGTGACT TATTATTACA ACATTTAATC TATAAATTCT   1740

ATTATGACAA TACCGTTAAT GATATCAAGA AAAATTTTGA CGAATCCTGG ACACAGACAT   1800

TAAAAGAATA AGCCTGCTTG GGGGTTTCTG GGCATCTCTT CATGAGTGCC AGTCACACAA   1860

CTCTTCTGTG AGCCTTCTAC AATAAGGACT TTGTGTGCTT CGATATTTTT TTAGACTAAA   1920

GTGAACTCTC TCCTCCACCT TTGGCTTCAG TTAGTTATTT CAAATGGCAA AAGTTATTAA   1980

AAATTCCAGT GTGGAAACTG GCTTAACCAA CAGGAAAGGG GTTTTGAGGT CGCATCACTA   2040

AGCATCAAGT TTAACACCAA CATGCCTGGA GGATTGGCTT AGCCGGTTGC TAGGGCAGGC   2100

CTGTGGCAGG GTTCTTATCC CAGCTATTAA CGCTCCCTTC CCACTCCTCC AAGTCCTGCA   2160

AGTCCTGGAT ACAGTGAAAT GTAATTGCAT ATCCCATATC CTTTGCTAGT ATCAAATGGA   2220

TAAAACCCAA AATGGAGTCA TACCAAATGA TCTCATGTAT ACAATACCTG AATAGTCTTG   2280

AACTGATGCA CTGTTAGATA GTATGCACTT ACTCTTCAGC TATTCATAGT GTGCCTCTGC   2340

ACAGTGATGG AAAAGAGGAG CACTGGGGGA GCTCGGTTTT CAAGGGACAA AGGAGAATAA   2400

GACACACAAA GAAATCCAAG GTAGAGCAGA GAAAGGATGG AGACACAGAA GGTTTGCAGG   2460

AACAGGAAGC GAAGGATGCT CCAGTCTGAG GGGAGGGGA AAGAGAGCCT CTTGAGTAGC   2520

CAGCACCTGA ACTTGGCCTG GAAGCTTGGT GGATAAGGCA GGATAAAGGA GGTGTGGCCT   2580

CTTTGGTATC CTCCCATTGA TAAAGGAGCT CCCTGACCCT TCACTAGACC ATCATCAGTC   2640

CTATGGTTCT TAGACCAATA GAACACAATG GAATTGATTT GTTCCACTTT CCAGGTTAAG   2700

ACTTACAGTC AGGGAAGTTT GTTTTTCTTG CC                                 2732
```

(2) INFORMATION FOR SEQ ID NO:3:

(i) SEQUENCE CHARACTERISTICS:
        (A) LENGTH: 2430 base pairs
        (B) TYPE: nucleic acid
        (C) STRANDEDNESS: single
        (D) TOPOLOGY: linear -continued (xi) SEQUENCE DESCRIPTION: SEQ ID NO:3:

```
AACTAGATGC AGCACCACAA TCACTACCAC GTACCAATCA TATACCAATA ATGTACTAAT      60
AATGTACCAA TAACTATGGT TTATAAAGAT GGTGTCATTT AAATCAATAT TAGTTCCTTA     120
TATTACACTC TTTTTAATGA GCGGTGCTGT CTTTGCAAGT GATACCGATC CCGAAGCTGG     180
TGGGCCTAGT GAAGCTGGTG GGCCTAGTGG AACTGTTGGG CCCAGTGAAG CTGGTGGGCC     240
TAGTGAAGCT GGTGGGCCTA GTGGAACTGG TTGGCCTAGT GAAGCTGGTG GCCTAGTGA      300
AGCTGGTGGG CCTAGTGAAG CTGGTGGGCC TAGTGAAGCT GGTGGGCCTA GTGGAACTGG     360
TTGGCCTAGT GGAACTGGTT GGCCTAGTGA AGCTGGTTGG TCTAGTGAAC GATTTGGATA     420
TCAGCTTCTT CCGTATTCTA GAAGAATAGT TATATTTAAT GAAGTTTGTT TATCTTATAT     480
ATACAAACAT AGTGTTATGA TATTGGAACG AGATAGGGTG AACGATGGTC ATAAAGACTA     540
CATTGAAGAA AAAACCAAGG AGAAGAATAA ATTGAAAAAA GAATTGGAAA ATGTTTTCC      600
TGAACAATAT TCCCTTATGA AGAAAGAAGA ATTGGCTAGA ATATTTGATA ATGCATCCAC     660
TATCTCTTCA AAATATAAGT TATTGGTTGA TGAAATATCA AACAAGGCCT ATGGTACATT     720
GGAAGGTCCA GCTGCTGATA ATTTTGACCA TTTCCGTAAT ATATGGAAGT CTATTGTACT     780
TAAAGATATG TTTATATATT GTGACTTATT ATTACAACAT TTAATCTATA AATTCTATTA     840
TGACAATACC GTTAATGATA TCAAGAAAAA TTTTGACGAA TCCAAATCTA AAGCTTTAGT     900
TTTGAGGGAT AAGATCACTA AAAGGATGG AGATTATAAC ACTCATTTTG AGGACATGAT      960
TAAGGAGTTG AATAGTGCAG CAGAAGAATT TAATAAAATT GTTGACATCA TGATTTCCAA    1020
CATTGGGGAT TATGATGAGT ATGACAGTAT TGCAAGTTTC AAACCATTTC TTTCAATGAT    1080
CACCGAAATC ACTAAAATCA CCAAAGTTTC TAATGTAATA ATTCCTGGAA TTAAGGCACT    1140
AACTTTAACC GTTTTTTTAA TATTTATTAC AAAATAGATG TAATACCAGA TGTATACATT    1200
ATTATATATT ACAAAATTTA CACATTATTT ATGTATGAAC GAACGAACAT CTCAGTCTTA    1260
AATGAAGAAA TTGGGATAAA TATGGAAATA GATTAAAGTA ACATGAGAAA GATGAATATA    1320
ATATTAGAAT ATGAAATTTA ACAGAAATAA AATGAAGTAA AAGAGTGTAT TTTGTAATAA    1380
TTTATAATAA ATTAGTATAC AATGATTATA TTACAGATGA CTATTGATTA TTGTATCAAT    1440
TAAATATTGA TTATTAATGA TATCATATAT GTATATGTTA ATGATTGATT TGTTATACGT    1500
TGTGAATATG TTATATAATG ACATACTATA ATAATTAATA TAATGTAGAG GATATTTTTT    1560
TTAATAGTAT TTAATGAATA TTATAGTTAT AATTATAATA ATGTAGATAA AAATGACATT    1620
AATTTGAATG TTTAAATTGA AATGTATGTA AAAATATGTA TTTATAATCT GAATTGATTA    1680
ATAATATAAT ATTCTACAAT TAATTATTTT TGTAATTATA ATAATTGATT ATATTAATCT    1740
TTGAATTATT ATAAATAATA TTATACTTCA TTAAATTATT TCACATAAAT TTCCAAATTA    1800
TTATCCTTTA TCTTAATGTT ATCCAATTTT ACACATCTTT CTTCATTACA ATATTTTTT     1860
ACTAATCCTG TATGCTCATA TTCATATTCT TTAGAAATAT AACGAAAATT AGATGTAACT    1920
TCGCCACTTA CAAGTAAACT ACCATCAATA TAATAATAAT GAATACCATT CATGTCCGTA    1980
TATTCTTTAT ATTTTTTATC ATATTTTATT TTGTGATTAT TCCATTCATT TGTATCATTA    2040
TTCAATGAGA GAAATAATAG CAGAAAGATC CTTCTATAGA AACATAAAAT TCAATTAATA    2100
CTGGATTATT ATGTTTGCAA GTATAGATGT TTAAATCAAT AACACTACCA GTTGGTAATT    2160
TAGCATTGTC ATCAAATTCA ATTATATAAT CAGAAATTTT GATTTATCA ATTTATTCG      2220
GATGTGATAA TTTATTTTGT TCTGATTCAT CGATCATGTA TACAAATACT ATTGTTAAAG    2280
GTTCCCTATC CTTATAATTA AAGTGGCCAA TAAGATTGGC ATTAATTACA TTAGTAGTGT    2340
```

| | |
|---|---|
| GTGTATTTGT AATAGTATCA TTAGTGGTAC TGACAGTTGT TATAGGTTTT GATTTCCATA | 2400 |
| ATGAAACATC ATTTTTATCT ACACAATACA | 2430 |

(2) INFORMATION FOR SEQ ID NO:4:

(i) SEQUENCE CHARACTERISTICS:
        (A) LENGTH: 1991 base pairs
        (B) TYPE: nucleic acid
        (C) STRANDEDNESS: single
        (D) TOPOLOGY: linear (xi) SEQUENCE DESCRIPTION: SEQ ID NO:4:

| | |
|---|---|
| AATGTACAAG ATCAAAATTT CTGATTATAT AATTGAATTT GATGACAATG CTAAATTACC | 60 |
| AACTGATAAT GTTATTGGTA TATCCATCTA TACTTGTGAA CACAATAATC CAGTATTAAT | 120 |
| TGAATTTTAT GTTTCTAAAA AAGGATCAAT CTGCTATTAT TTCTACTCAA TGAATAATGA | 180 |
| TACAAATAAA TGGAATAATC ACAAAATAAA ATATGACAAA AGATTTAATG AACATACTGA | 240 |
| CATGAATGGT ATTCATTATT ATTATATTGA TGGTAGTTTA CTTGCGAGTG GCGAAGTTAC | 300 |
| ATCTAATTTT CGTTATATTT CTAAAGAATA TGAATATGAG CATACAGAAT TAGCAAAAGA | 360 |
| GCATTGCAAG AAAGAAAAAT GTGTAAATGT GGATAACATT GAGGATAATA ATTTGAAAAT | 420 |
| ATATGCGAAA CAGTTTAAAT CTGTAGTTAC TACTCCAGCT GATGTAGCGG GTGTGTCAGA | 480 |
| TGGATTTTTT ATACGTGGCC AAAATCTTGG TGCTGTGGGC AGTGTAAATG AACAACCTAA | 540 |
| TACTGTTGGT ATGAGTTTAG AACAATTCAT CAAGAACGAG CTTTATTCTT TTAGTAATGA | 600 |
| AATTTATCAT ACAATATCTA GTCAAATCAG TAATTCTTTC TTAATAATGA TGTCTGATGC | 660 |
| AATTGTTAAA CATGATAACT ATATTTTAAA AAAAGAAGGT GAAGGCTGTG AACAAATCTA | 720 |
| CAATTATGAG GAATTTATAG AAAAGTTGAG GGGTGCTAGA AGTGAGGGGA ATAATATGTT | 780 |
| TCAGGAAGCT CTGATAAGGT TTAGGAATGC TAGTAGTGAA GAAATGGTTA ATGCTGCAAG | 840 |
| TTATCTATCC GCCGCCCTTT TCAGATATAA GGAATTTGAT GATGAATTAT TCAAAAAGGC | 900 |
| CAACGATAAT TTTGGACGCG ATGATGGATA TGATTTTGAT TATATAAATA CAAGAAAAGA | 960 |
| GTTAGTTATA CTTGCCAGTG TGTTGGATGG TTTGGATTTA ATAATGGAAC GTTTGATCGA | 1020 |
| AAATTTCAGT GATGTCAATA ATACAGATGA TATTAAGAAG GCATTTGACG AATGCAAATC | 1080 |
| TAATGCTATT ATATTGAAGA AAAAGATACT TGACAATGAT GAAGATTATA AGATTAATTT | 1140 |
| TAGGGAAATG GTGAATGAAG TAACATGTGC AAACACAAAA TTTGAAGCCC TAAATGATTT | 1200 |
| GATAATTTCC GACTGTGAGA AAAAAGGTAT TAAGATAAAC AGAGATGTGA TTTCAAGCTA | 1260 |
| CAAATTGCTT CTTTCCACAA TCACCTATAT TGTTGGAGCT GGAGTTGAAG CTGTAACTGT | 1320 |
| TAGTGTGTCT GCTACATCTA ATGGAACTGA ATCTGGTGGA GCTGGTAGTG GAACTGGAAC | 1380 |
| TAGTGTGTCT GCTACATCTA CTTTAACTGG TAATGGTGGA ACTGAATCTG GTGGAACAGC | 1440 |
| TGGAACTACT ACGTCTAGTG GAACTTGGTT TGGAAAATGA AAAATTAGCT CTAGAAACAC | 1500 |
| TTTATTGTTA ATTTTTAAAA ACCTATTGAA AAATCAGATT GTAAACATA ATTCCACTTC | 1560 |
| TAACCATGCT ATGATTTAAC TAATCAGGAC AAAAAGAAAG CATAATCAAC ATTATTCATT | 1620 |
| CAGTGATGGT GACATAATTC AGAGAATGTG GCAATTGCCT CTTGAAGACC AGAGTTCCAT | 1680 |
| CCACAGGACC CACATGGTTA AAGGAGAGAG CTAACTCCTG AAAGTTGTCC TCTGACTAAC | 1740 |
| ACATTCAACT TTTGAGTGTC TCATTTATGT GTTGGCTTCT GTCTAATGTG GAAAATCAT | 1800 |
| TAAGGGCTCT TAAATCAGAT CCTCATTCTC TCTATTAATA AACTATGTGA TAACATCCTT | 1860 |
| CAGCTATGAA AATGTCAGGA GAGAGTCAGG AAAATGGAAG ATATTGTTCA GGACTTAACT | 1920 |

```
AGGTGGTGGC ACACAGTTCC TTTACACAGA TTCCTCAGGA CAAGTTTTAG GTGAGGTTTT    1980

GATCTATCCT G                                                        1991
```

(2) INFORMATION FOR SEQ ID NO:5:

(i) SEQUENCE CHARACTERISTICS:
        (A) LENGTH: 1271 base pairs
        (B) TYPE: nucleic acid
        (C) STRANDEDNESS: single
        (D) TOPOLOGY: linear (xi) SEQUENCE DESCRIPTION: SEQ ID NO:5:

```
TTCACTAGGC CAACCAGCTT CACTAGGCCA ACCAGCTTCA CTAGGCCAAC CAGCTTCACT      60

AGGCCAACCA GCTTCACTAG GCCAACCAGC TTCACTAGGC CAACCAGTTC CACTAGGCCC     120

ACCAGCTTCA CTAGGCCCAC CAGCTTCACT AGGCCCACCA GCTTCACTAG GCCAACCAGT     180

TCCACTAGGC CCACCAGCTT CACTAGGCCC ACCAGCTTCA CTAGGCCCAC CAGCTTCACT     240

AGGCCCACCA GCTTCACTAG GCCCACCAGC TTCACTAGGC CCACCAGCTT CACTAGGCCC     300

ACCAGCTTCA CTAGGCCCAC CAGCTTCACT AGGCCCAACA GTTCCACTAG GCCCACCAGC     360

TTCGCGATCG GTATCACCTG CAAAGACAGC ACCGCTCATT AAAAAGAGTG TAATATAAGG     420

AACTAATATT GATTTAAATG ACACCATCTT TATAAACCAT AGTTATTGGT ACATTATTAG     480

TACATTATTG GTATATGATT GGTACGTGGT AGTGATTGTG GTGCTGCATC TAGTTGTCAT     540

CAATGTGCAT ACATCCTAAC TAATAAGCTA ATAAGCTAAT AAGCAGTTAT ACAATTTCTG     600

ATAATTGCTT CCAGTTATTC TAGAATCGAT TTGAAGATTT TTCTAAGATT GGGGATAGAC     660

GTCAATGAAG CTAGGTTAG GGTTAGGGTT AGGGTTAGGG TTAGGGTTTA GGGTTTAGGG      720

TTTAGGGTTT AGGGTTTAGG GTTAGGGTTT AGGGTTTAGG GTTTAGGGTT TAGGCTCCCA     780

AGTTGTCCCG TGAAAGGGCC GTGTCTTTGA TAAATTTTGC CGTCCTGTAC GTTTCCTTTC     840

TAGAATGCAC AAAAACAAGA ATTTGGCAGC TAGAAACATC GTTAATCACC TCTTGGTAGA     900

GAATTTCGTT GATTGCGTTG AAACGTTTGA TAGCCTTCTT CTCCTTCACG CCATAATACA     960

CCTGCTCCAA GGGCACAGGC CTAAAGTGGC TGCCAAAGTA GAAAAGCCCT CGGTCTAGAT    1020

TAACAGTGAG AAATCTAGCC ACGTCTTCGT AGTTTGGAAG CGTGGCCGAT AGACCAACTA    1080

GCCTTACGCG TTCGGGCCTC TGACTCAGGC GGGCCACAAT AGCCTCCAGC ACTGGACCCC    1140

TAGTGTCATG GAGTAGGTGT ATTTCATCAA TTATAACCAA TCTAAGCCGC TCAAGCAGGG    1200

GCTCATTGCC TGTTTTACGT GTAACTACGT CAAACTTCTC TGGCGTAGTT ACAATTATAT    1260

GCGTTTTCTC A                                                         1271
```

(2) INFORMATION FOR SEQ ID NO:6:

(i) SEQUENCE CHARACTERISTICS:
        (A) LENGTH: 1821 base pairs
        (B) TYPE: nucleic acid
        (C) STRANDEDNESS: single
        (D) TOPOLOGY: linear (xi) SEQUENCE DESCRIPTION: SEQ ID NO:6:

```
TAAACCCTAA ACCCTAAAC CCTAAACCCT AAACCCTAAA CCCTAAACCC TAAACCCCTA       60

AACCCTAAAC CCTAAACCCT AAACCCTAAA CCCTAACCCT AAACCCTAAA CCCTAAACCC     120

TAAACCCTAA ACCCTAACCC TAACCCTAAC CTAACCCTA ACCTAGCCTT CATTGACGTC      180

TATCCCCAAT CTTAGAAAAA TCTTCAAATC GATTCTAGAA TAACTGGAAG CAATTATCAG     240
```

-continued

| | |
|---|---|
| AAATTGTATA ACTGCTTATT AGCTTATTAG CTTATTAGTT AGGATGTATG CACATTGATG | 300 |
| ACAACTAGAT GCAGCACCAC AATCACTACC ACGTACCAAT CATATACCAA TAATGTACTA | 360 |
| ATAATGTACC AATAACTATG GTTTATAAAG ATGGTGTCAT TTAAATCAAT ATTAGTTCCT | 420 |
| TATATTACAC TCTTTTTAAT GAGCGGTGCT GTCTTTGCAG GTGATACCGA TCGCGAAGCT | 480 |
| GGTGGGCCTA GTGGAACTGT TGGGCCTAGT GAAGCTGGTG GGCCTAGTGA AGCTGGTGGG | 540 |
| CCTAGTGAAG CTGGTGGGCC TAGTGAAGCT GGTGGGCCTA GTGAAGCTGG TGGGCCTAGT | 600 |
| GAAGCTGGTG GGCCTAGTGA AGCTGGTGGG CCTAGTGAAG CTGGTGGGCC TAGTGGAACT | 660 |
| GGTTGGCCTA GTGAAGCTGG TTGGCCTAGT GAAGCTGGTT GGCCTAGTGA AGCTGGTTGG | 720 |
| CCTAGTGAAG CTGGTTGGCC TAGTGAAGCT GGTTGGCCTA GTGAACGATT TGGATATCAG | 780 |
| CTTCTTTGGT ATTCTAGAAG AATAGTTATA TTTAATGAAA TTTATTTATC TCATATATAC | 840 |
| GAACATAGTG TTATGATATT GGAACGAGAT AGGGTGAACG ATGGTCATAA AGACTACATT | 900 |
| GAAGAAAAAA CCAAGGAGAA GAATAAATTG AAAAAGAAT TGGAAAAATG TTTTCCTGAA | 960 |
| CAATATTCCC TTATGAAGAA AGAAGAATTG GCTAGAATAA TTGATAATGC ATCCACTATC | 1020 |
| TCTTCAAAAT ATAAGTTATT GGTTGATGAA ATATCCAACA AAGCCTATGG TACATTGGAA | 1080 |
| GGTCCAGCTG CTGATGATTT TGACCATTTC CGTAATATAT GGAAGTCTAT TGTACCTAAA | 1140 |
| AATATGTTTC TATATTGTGA CTTATTATTA AAACATTTAA TCCGTAAATT CTATTGTGAC | 1200 |
| AATACCATTA ATGATATCAA GAAAAATTTT GACGACATAG AGAAATTGGG CTGTTTTCAA | 1260 |
| GCTAGAAGCT TCCTCCCTGT TAACTAATGT ATTCATGGTG CCAGAAGGTG CTATGCAGGT | 1320 |
| TGCTAGGGAA TCAAATTCAT CAATAGTCCT GCCCAAGAGT AGTGTGTTAA CTGGCGGTGC | 1380 |
| AAGATGTGCC CTTTGATGCA GTAGTGGCAT GCTTGTTTGT GGGGTAACCC AGTGCTTTCT | 1440 |
| GATTGAGGTC TACTCCACAG GAGGAATAGA TACCTGCTTC TGTAAACTTG GTCAAAACTT | 1500 |
| ATGACTGCAC ATGAAGACAG AGTGGAAAAG ACCTGAAAAC ACACGGGG TCAGGACTGA | 1560 |
| GGAAGACAGG GTTAGTATTA GAGAGATTTG GGGAAAAAAA GAGTTAGCAA ATATAGAGTG | 1620 |
| TGATAGTCTA ATGGGGGAT GAATGGTATC AAAATGAATT ATTTATATGT ATAAAACTGA | 1680 |
| CAATTTTTTA ATTGTGAAAA GGAATGCAAT CCGACCCATC TGGGGGAATT CTAGCTAGCA | 1740 |
| TCAGTGAGAG AAGAGGCAAG GTGTTAGGAA ATCGTGCAGA ACATGCTCAT CCAGGCTTTA | 1800 |
| TTTCTCCATT TACATCTAGA G | 1821 |

(2) INFORMATION FOR SEQ ID NO:7:

(i) SEQUENCE CHARACTERISTICS:
        (A) LENGTH: 4223 base pairs
        (B) TYPE: nucleic acid
        (C) STRANDEDNESS: single
        (D) TOPOLOGY: linear (xi) SEQUENCE DESCRIPTION: SEQ ID NO:7:

| | |
|---|---|
| CATCACAATT ATTGGCTGTT ACATCACTAT AGTGCTGTAT GTAAAAAATT ATAAAGTGTG | 60 |
| ACATCATTAT AATGCAATAT GACATCACAA TTATATACTG TGACTTCACT ATCTTGCACT | 120 |
| TTAACATCAC AATTATACAT TGTGACATCA ATATACTGCA CTATGCATC ACGATTATTG | 180 |
| ACTGTGACAT CAATACATTC TCTATGAACA CAGTTATACA CTCTGACATC ACTAGCTTGC | 240 |
| ACTGTGACAT GACAATTAAA AACTGTGACA TCAATATAAT GGACTGTGAC CTACAATTAT | 300 |
| TCACTGTGAA ACCACAACAC TGCAATTGTG TATAATTGGG ATGGGTACTG ATCTGCTGCC | 360 |
| CGAGGCTCAA TAGATTACCT AGGCCTCCTC ACTGACACCC ACATTCAGGG GGTCTTGATC | 420 |

-continued

```
AGTCCCATGA TGGATTCCCA GGCTGATGCC TGGGATTCAA GAGTTAACCT TTGTCTGGTC    480

AGCTCTTTCT GGGGGTTAAA CGGATTAAAT GTTTTAATAA TAAGTCACAA TATAGAAACA    540

TATTTTTAGG TACAATAGAC TTCCATATAT TACGGAAATG GTCAAAATCA TCAGCAGCTG    600

GACCTTCCAA TGTACCATAG GCTTTGTTGG ATATTTCATC AACCAATAAC TTATATTTTG    660

AAGAGATAGT GGATGCATTA TCAATTATTC TAGCCAATTC TTCTTTCTTC ATAAGGGAAT    720

ATTGTTCAGG AAAACATTTT TCCAATTCTT TTTTCAATTT ATTCTTCTCC TTGGTTTTTT    780

CTTCAATGTA GTCTTTATGA CCATCGTTCA CCCTATCTCG TTCCAATATC ATAACACTAT    840

GTTCGTATAT ATGAGATAAA TAAATTTCAT TAAATATAAC TATTCTTCTA GAATACCAAA    900

GAAGCTGATA TCCAAATCGT TCACTAGGCC AACCAGCTTC ACTAGGCCAA CCAGCTTCAC    960

TAGGCCAACC AGCTTCACTA GGCCAACCAG CTTCACTAGG CCAACCAGCT TCACTAGGCC   1020

AACCAGCTTC ACTAGGCCCA CCAGCTTCAC TAGGCCCACC AGCTTCACTA GGCCCACCAG   1080

CTTCACTAGG CCCAACAGTT CCACTAGGCC CACCAGCTTC ACTAGGCCCA CCAGCTTCAC   1140

TAGGCCCACC AGCTTCACTA GGCCCACCAG CTTCACTAGG CCCACCAGCT TCACTAGGCC   1200

CACCAGCTTC ACTAGGCCCA CCAGCTTCAC TAGGCCCAAC AGTTCCACTA GGCCCACCAG   1260

CTTCGCGATC GGTATCACCT GCAAAGACAG CACCGCTCAT TAAAAAGAGT GTAATATAAG   1320

GAACTAATAT TGATTTAAAT GACACCATCT TTATAAACCA TAGTTATTGG TACATTATTA   1380

GTACATTATT GGTATATGAT TGGTACGTGG TAGTGATTGT GGTGCTGCAT CTAGTTGTCA   1440

TCAATGTGCA TACATCCTAA CTAATAAGCT AATAAGCTAA TAAGCAGTTA TACAATTTCT   1500

GATAATTGCT TCCAGTTATT CTAGAATCGA TTTGAAGATT TTTCTAAGAT TGGGGATAGA   1560

CGTCAATGAA GGCTAGGTTA GGGTTAGGGT TAGGGTTAGG GTTAGGGTTT AGGGTTTAGG   1620

GTTTAGGGTT TAGGGTTTAG GGTTAGGGTT TAGGGTTTAG GGTTTAGGGT TAGGGTTTA    1680

GGGGTTTAGG GTTTAGGGTT TAGGGTTTAG GGTTTAGGGT TTAGGGTTTA GGGAAGGCTG   1740

AGAACCACTG ACTTAGACTT TCCAAGACTT TGTCATCTTA TGACTTGCCG GTTGCCTCGT   1800

TTCTCCACAC AGCAACCTAT GTTCTCTCTT ATTACAGTTT CTGTGGGACA TGTCATGCTT   1860

CCAGCTTCGA GAATGGAAGC CTATTGTCTT AATGGGTGAG CAAAGTGGGC CCATTCATTA   1920

ATCACAGACT AATCCAAAAG GAAATGTGAC ACCTGACCTA AGTCCGACCA ATAGGAGCCA   1980

GGAAAGCTCA CTTCTGGAAT TGTGACTTAG ATATCACGGA TGCATACAGA CTCTTTTTCC   2040

TGCTGAAACA AATGGTGAGG ACCTGTCCAC CCTTGTGGGA AGCTTGCAGT GTAAGATTCT   2100

AATCCATATT GGGGAAATAA GGCTGAGAAG AGAGAGTTCC AGGCCTTGTG ACAGAATCTA   2160

ATCCCTGGAT AAAGTCTCTC TTTTTACAAA GAACATCAGT GTTGCAAGCT CCAAATTCCT   2220

GTTCTTACTT TCTTGAGTCT GTTTTCTTTA TGTATAACCC AAAGCACTTT AACTGACACA   2280

GCTGTGAAGT GAGAATATTT CATAGAAATC CTATTGTTTT GATGTCTTCT AAAAAAGAAA   2340

AAAAGCAATG ATCTGTAACA TTTTTTAACT TAAATAATTA GATTGATTTA AGTGACATCA   2400

AAACATCTGG AAAATGGTGT GGACACAAAT TCACTAGAGA GCCATATTTT TTGCTAACTA   2460

ATTGAGAAAT TAATCACTGG CAAGTCTTTG GTAAAAGTAT CACCTCAGTC ATGATCTCTC   2520

CTGCCTTCAT GACATTTTCC TCATTGGTGT GAGGATGCTA TTCTGCTTTC TATGTGACCA   2580

GGAAATAGTG CTGTCTTCTG TCTAGTTATG ATTTAGGTTG TACACCAGGT TTTCACATAT   2640

GTTCCCTAAC GTCTGTAGTA GGACCAGGGA CTGGTTGGCT TCAAGTTGTT GGATATGGTT   2700

ACCTTAAGTC ATTCATGTAC AGGAACTCAT TTGAGATGAT AGGAAATGAA GTGAAAGATT   2760

TTCTTGCCCC TGTTAAGTAA GATAAAAAGG ATTGTTATGA TGGGGCAGGA GCAGATCTAT   2820
```

```
TTCCAATAAA CAGAATTTGA AGTGTTTGTG TGATATTCAG ATACCTCATT GTCATTTGAA      2880

TGAATTACTC CTGCTCTCAG TGAAGATGTC TAAGCTGCAA ATAAGAAATG GAGAGCGCTG      2940

TCAGAAGTCA GATGGAATTG AGAATAGGGG CCTGGCTGCA ATCTGTGGAG ACTGCCTAAA      3000

GCAGCTAGAT AAGAAACTAG CAGCTGGGGA GAGAAAGATC GAATTTAGTC GGCCTGTTTT      3060

ATATTTTCTT ATAAAAAATA ACTGCTTCGA AATGTTTGAG AAGATAGAGG CAATGAGCAG      3120

AAAGTTGTTC CTTAAATCAG TTATAGAATG AACACATACA CGGGCACTCA GATCAAGCCA      3180

TGCTGAGCTT GAGACACCGG GTGACGCGTG ACTTGTTTAT TCCCAGGCTG CAAAGGAGAG      3240

TAAATGAAGT AACGGGAAGG CCCGGTGTGG TAGGCACACT CCTGCCTGGC ACCATCTGCT      3300

GCTTTTGTCC CTGTTACTCC TTGTTCCTTT CCCTCCTTTT CTCCCTCCCT TCCTCCCTCC      3360

CTCTCTCCCT CCTTCACACT TCTGTCTTTA TTTCCTCCTG GGAGTTAATT GGTGGTAGCC      3420

CCTCTGTGCT GTTCTTTCGG GGGTGCCTTT AATTTCGACA ATACAATGCC ATCCATGGGG      3480

GCATTTTATA TACAGTAATA ATTGTCATTG ATGTGGCCAT AAGGTACTTT TTTGTGGTAC      3540

CCTTCTTGAA CAGAACAGAC ACAGAAGGGC GTGCGTGCGT GCGTGCGTGC GTGCGTGCGT      3600

GCGTGTGTGC GTGTGTGCGT GCGTGTGTGC GTGTGTGCGT GCGTGCGTGT GTGCGTGCGT      3660

GCGTGTGTGC GTGTGTGTGT GTGTGTGTGT GTGTGTGTGT GTGTGTGTGT GTGTGTTGGG      3720

ATGGGGTGGG GAGCGCTAGC TTCCTACTTG TTGTAGGGTG ATGAGGTTTT ATATAGTCTG      3780

TTTCTGAGAC AGTTACCAAA TCCAGCTGGG TTACTTTTTT TTTGGTTTTT TATGAGACAG      3840

GGTTTCTCTG TATTGTTTTG GAGGCTGTCG GTCCAGCCTG GTCTCGAACT CACAGAGATC      3900

CGCCTGCCTC TGCCTCCCGA GTGCTGGGAT TAAAGGTGTG CGCCACCACC GCCCGGCCCC      3960

AGCTGGGTTA CTTATCACTC AGTGGATCTT TCTCTTTTCT TTGTAAGAAG AACTTTGCAT      4020

TGTGGGTCGT CATGGAAGAA CACTTGGAAA GGTACCCTTT CTGCCCCACC CGTTTATTGA      4080

ATGAGTCTTT TTTTTTTTTA ATTAAATAGC AGAACTTTGG GGAAAGATTT AGAAAAGGCC      4140

CTTTTCATAT TATAATACGA GGTATAGGAT GGTTTAAGAT AAGAGACTTT TTGTTAGCTG      4200

TTATCAGTTG AGAAAGGCAC GAG                                            4223
```

(2) INFORMATION FOR SEQ ID NO:8:

(i) SEQUENCE CHARACTERISTICS:
        (A) LENGTH: 2287 base pairs
        (B) TYPE: nucleic acid
        (C) STRANDEDNESS: single
        (D) TOPOLOGY: linear (xi) SEQUENCE DESCRIPTION: SEQ ID NO:8:

```
TTATAAACAT ATCTAAATAT TTTAATAATA ATGATGAAAT TTAACATAGA TAAGATAATA        60

TTAATCAATT TAATAGTATT ATTGAATCGA AATGTAGTGT ATTGTGTGGA TACAAATAAT       120

AGTTCATTAA TTGAATCACA ACCAGTAACA ACTAACATTG ACACTGATAA TACAATTACA       180

ACAAATAAAT ACACTGGTAC TATAATTAAT GCCAATATTG TTGAGTACCG TGAATTTGAG       240

GATGAACCTT TAACAATAGG GTTTAGATAC ACTATAGATA AATCACAACA AAATAAATTA       300

TCACATCCAA ATAAAATTGA TAAAATCAAA TTTTCTGATT ATATAATTGA ATTTGATGAC       360

AATGCTAAAT TACCAACTGA TAATGTTATT TGTATATCCA TCTATACTTG CAAGCATAAT       420

AATCCAGTAT TAATTAGATT CTCATGTTCT ATAGAAAAAT ATTACTACCA TTACTTCTAC       480

TCAATGAATA ATGATACAAA TAAATGGAAT AATCACAAAT TAAAATATGA TAAAACATAC       540

AATGAATATA CTGACAATAA TGGTGTTAAT TATTATAAAA TCTATTATAG TGATAAACAG       600
```

```
AATTCCCCTA CTAATGGAAA TGAATATGAG GATGTAGCAT TAGCAAGAAT ACATTGTAAT      660

GAAGAAAGAT GTGCAAATGT AAAGGTAGAT AAAATTAAAT ATAAGAATTT GGAAATTTAT      720

GTGAAACAGT TAGGTACTAT AATTAATGCC AATATTGTTG AGTACCTTGT ATTTGAGGAT      780

GAACCTTTAA CAATAGGGTT TAGATACACT ATAGATAAAT CACAACAAAA TGAATTATCA      840

CATCCAAATA AAATTTATAA AATCAAATTT TCTGATTATA TAATTGAATT TGATGATGAT      900

GCTAAATTAA CAACAATTGG TACTGTTGAA GATATAACCA TCTATACTTG CAAGCATAAT      960

AATCCAGTAT TAATTAGATT CTCATGTTCT ATAGAAAAAT ATTACTACTA TTACTTCTAC     1020

TCAATGAATA ATAATACAAA TAAATGGAAT AATCACAACT TAAAATATGA ATAATAGATTC   1080

AAAGAACATA GTGACAAGAA TGGTATTAAT TATTATGAAA TCTCAGCTTT CAAATGGAGT     1140

TTCTCTTGTT TTTTCGTTAA TAAATATGAG CATAAAGAAT TAGCAAGAAT ACATTGTAAT     1200

GAAGAAAGAT GTGCAAATGT AAAGGTAGAT AAAATTAAAT ATAAGAATTT GGAAATTTAT     1260

GTGAAACAGT TAGGTACTAT AATTAATGCC AATATTGTTG AGTACCTTGT ATTTGAGGAT     1320

GAACCTTTAA CAATAGGGTT TAGATACACT ATAGATAAAT CACAACAAAA TGAATTATCA     1380

CATCCAAATA AAATTTATAA AATCAAATTT TCTGATTATA TAATTGAATT TGATGATGAT     1440

GCTAAATTAA CAACAATTGG TACTGTTGAA GATATAACCA TCTATACTTG CAAGCATAAT     1500

AATCCAGTAT TAATTAGATT CTCATGTTCT ATAGAAAAAT ATTACTACTA TTACTTCTAC     1560

TCAATGAATA ATAATACAAA TAAATGGAAT AATCACAACT TAAAATATGA ATAATAGATTC   1620

AAAGAACATA GTGACAAGAA TGGTATTAAT TATTATGAAA TCTCAGCTTT CAAATGGAGT     1680

TTCTCTTGTT TTTTCGTTAA TAAATATGAG CATAAAGAAT TAGCAAGAAT ACATTGTAAT     1740

GAAGAAAAAT GTGTAAATGT AAAGGTAGAT AACATTGGGA ATAAAAATTT GGAAATTTAT     1800

GTGAAATAAT TTAATGAAGT ATAATATTAT TTATAATAAT TCAAAGATTA ATATAATTAA     1860

TTATTATAAT TACAAAAATA ATTAATTGTA GAATATTATA TTATTAATCA ATTCAGATTA     1920

TAAATACATA TTTTTACATA CATTTCAATT TAAACATTCA AATTAATGTC ATTTTTATCT     1980

ACATTATTAT AATTATAACT ATAATATTCA TTAAATACTA TTTAAAAAAA TATCCTCTAC     2040

ATTATATCAA TCAATATAAT ATACAATTAT ATAATATATT CACAATGTAT AACAATCAAC     2100

CCTAACATGT ACATACATAA TATCATTACT AATCAATATT TAATTAATAA AATATTTAAT     2160

AGTCATCTGT AATATAATCA TTGTATACTA ATTTATTATA AATTATTACA AAATACACTC     2220

TTTTACTTCA TTTTATTTCT GTTAAATTTC ATATTCTAAT ATTATATTCA TCTTTCTCAT     2280

GTTACTT                                                              2287

(2) INFORMATION FOR SEQ ID NO:9:

(i) SEQUENCE CHARACTERISTICS:
        (A) LENGTH: 2784 base pairs
        (B) TYPE: nucleic acid
        (C) STRANDEDNESS: single
        (D) TOPOLOGY: linear (xi) SEQUENCE DESCRIPTION: SEQ ID NO:9:

CACTGCTTTC GCAGCGTTTC TTGCTTTTGG GAATATCTCA CCTGTACTTT CTGCTGGTGG       60

TAGTGGTGGT AATGGTGGTA ATGGTGGTGG TCATCAAGAG CAAAATAATG CTAATGATAG      120

TAGTAATCCC ACCGGAGCCG GTGGACAACC CAATAACGAA AGTAAGAAAA AGGCAGTAAA      180

ACTTGACTTG GACCTCATGA AAGAAACAAA GAATGTTTGC ACCACTGTTA ATACTAAACT      240

AGTCGGAAAA GCAAAGAGCA AATTAAACAA ATTAGAAGGT GAATCCCATA AGGAGTATGT      300
```

```
AGCTGAGAAA ACGAAGGAGA TAGATGAGAA AAATAAGAAA TTTAACGAGA ATCTTGTTAA    360

AATAGAGAAA AAGAAGAAAA TTAAGGTTCC TGCCGATACT GGTGCTGAAG TGGATGCTGT    420

TGATGATGGT GTTGCGGGTG CACTATCCGA TTTATCCTCC GATATCTCCG CTATTAAGAC    480

TCTCACCGAC GATGTATCCG AGAAGGTTTC TGAAAACTTG AAAGATGATG AGGCCAGTGC    540

AACAGAACAC ACTGATATAA AAGAAAAAGC CACCCTGCTT CAAGAGTCTT GCAACGGAAT    600

TGGCACTATC CTAGATAAGT TGGCCGAATA TTTAAATAAT GATACAACTC AAAATATCAA    660

GAAAGAATTT GATGAACGCA AGAAGAATCT CACCTCTTTG AAGACAAAGG TAGAAAATAA    720

GGATGAAGAT TATGTTGATG TTACCATGAC ATCAAAAACA GATCTGATAA TACACTGTTT    780

AACTTGCACA AACGATGCAC ACGGACTGTT TGATTTCGAA TCGAAGAGCT TGATAAAACA    840

AACCTTTAAA TTGAGGTCCA AGATGAAGG TGAACTCTGC TAATTTAGAT TTTAGATGGG     900

CCATGTATAT GTTAAACAGC AAGATTCATC TTATAGAAAG CAGTTTGATC GATAACTTCA    960

CCTTGGATAA TCCATCCGCA TACGAAATTT TACGCGTTTC TTATAACTCA AATGAATTTC   1020

AAGTACAATC ACCGCAGAAC ATTAACAATG AAATGGAATT TCAACGCCC GAATCCAATA    1080

TCATTTGGGT TGTACATAGT GATGTTATAA TGAAAAGGTT CAACTGTAAA AATCGCAAAT   1140

CTCTCAGTAC TCATTCACTC ACTGAAAATG ATATTCTCAA GTTTGGCCGT ATAGAACTCT   1200

CTGTTAAATG TATAATTATG GGCGCAGGTA TCACTGCATC TGATCTTAAT CTAAAGGGAT   1260

TGGGGTTTAT TAGTCCAGAT AAACAATCAA CTAATGTATG TAACTATTTT GAAGATATGC   1320

ATGAATCTTA TCATATTCTT GATACACAAA GGGCCTCGGA TTGTGTATCA GATGATGGCG   1380

CTGATATTGA TATATCCAAC TTCGACATGG TCCAAGACGG TAACATAAAT TCTGTTGACG   1440

CTGATTCTGA AACATGTATG GCAAACTCTG GCGTAACGGT CAATAATACT GAAAATGTTA   1500

GTAATAGTGA GAATTTTGGA AAATTAAAAT CATTGGTAAG CACCACCACT CCTTTGTGCC   1560

GTATTTGCCT GTGTGGTGAA TCAGACCCTG GGCCACTAGT AACCCCTTGC AATTGCAAGG   1620

GGTCCCTAAA TTATGTCCAT CTTGAATGCC TAAGGACTTG GATTAAAGGG CGGTTGTCAA   1680

TTGTGAAGGA TGATGATGCT TCCTTTTTCT GGAAAGAGCT ATCATGTGAG CTATGCGGGA   1740

AGCCGTATCC ATCGGTCCTA CAAGTAGATG ATACAGAGAC TAATTTGATG GATATAAAAA   1800

AACCGGATGC ACCATATGTG GTATTGGAAA TGAGATCAAA TTCTGGTGAT GGGTGTTTCG   1860

TTGTTTCTGT AGCTAAAAAT AAGGCGATTA TTGGACGGGG GCATGAAAGT GACGTTAGGT   1920

TGAGTGATAT TTCAGTGTCA CGAATGCATG CTTCTTTGGA ATTGGATGGT GGAAAAGTAG   1980

TGATACATGA CCAGCAATCT AAGTTTGGTA CACTCGTTAG GGCCAAAGCG CCTTTTTCAA   2040

TGCCTATAAA GGGTCCCATC TGTCTACAGG TAAGCATTTT CTTTTTGAAC TTGAAAATAT   2100

CTACTCATAG TCTAACCATG GAGAGGGCA TGGAACATGT CCTTCTCTAA TATTTCCAAA    2160

AAGGATCTAT GCCTGATAAC CTTGGTATTG AAGGTGGCTT TCTCAAAGTG AGACATTCCA   2220

TTTCTGTTGT TGGAGCTATC CTATCTGAGG TTAGTGTTCT GGTAAACATT CCTAGAAAAC   2280

TCATAAAGCA GAAATCTGTG TGTATACTAA ATTGCACAGA GAACTCCACG TGTGTGCTAG   2340

ACTTCACAGA GAACTCTGTG TGTGTGCTAA ACTGCATAGA GAAGAACATG TTGAGTGCAT   2400

CATGGTTGAG GGAAATTGCT TTATATAAAA GATTATTTT CCTAAGGTAA CTTAGGATTA    2460

ATTTTTCTGA AAGCTTAGTT TTGGTGAGCA CAATTGTGAT CTTTGTTTCT CAGATGGTCG   2520

GGAAGGCACT CCCAGAAAGC AGGTGGATAC ACACTACACT GCATGCTACA CTCTGTAGAC   2580

TAGGAGTATC GTTTTCACAC TTATGAAATA GTCACCATGC TGGGCACAAA TATCTTTTTA   2640
```

-continued

```
TACACCATAT ATTGTTCATG TTCAGGTCCA CATTTCAATT TGTATGTGAA AAGCATCCGG    2700

GGCTGTCTGA TAAACACATA GAAATGAAGG AAACAGTGTA TGTAACTGAA GCCTTCAGTC    2760

CTTTGCAATT TCTTTGATTC TTAG                                          2784
```

(2) INFORMATION FOR SEQ ID NO:10:

(i) SEQUENCE CHARACTERISTICS:
        (A) LENGTH: 3701 base pairs
        (B) TYPE: nucleic acid
        (C) STRANDEDNESS: single
        (D) TOPOLOGY: linear (xi) SEQUENCE DESCRIPTION: SEQ ID NO:10:

```
ACCTATTTAT AATATAGTAT ATTACTGGTT TGTTTTAAAT CGAAAAAATG TATTGTATTT      60

AAGAATGAAA TTATTTATTT ATCATGATTA TCATATTTCT AAATATTAAA ATCTAGTAAC     120

GGTTGCTTGA ATATTTATTT AAATTATATG TAGTAGTATT AAAATGTGTT ATATATAAGT     180

AGTGTTCTAA ATCATCATTA GTAATATTGT ATAAATTAAT TGTAAAAATT GCGATACTAC     240

AATTAATCAA CAATTAAAAT ATATCAGTAT AGATAATTTA ATAAATAAT TAGATAAGAT      300

CTTAAGGATT AAATGACGAA TTTAGAATGA TAAATAATCA TCATAGGCAT TTGTTATAAT     360

ATCATTAATT ATATTCATGT GGTTATAATT ATAAAAGTAT ATATAGTTTT GTAATTGTAA     420

TGATATAAAA TTAGAACAGA TATAATTAAT AATTCAAATA TTATATTAAT TTTATTATAT     480

ATGATTATTA TTGATATTTA TATAATTACA TATTGTTATT GTATCATTTA ATGATTATAT     540

ATCAATATCC ATATATATAT ATAATAATTG AATTATAATT AAATTAATTG GCATATTACA     600

TTTATAATAA TATATTATTA GTCAATATGA CATCATATTA TATTATCCAT CATGATTGTG     660

AATGTAACTA GAACATTGAT TATTATATTA AATCACATAT TAATACTGAT TATAATAATA     720

TCATTGATAA TCTAATAATA TAGTATTATC TCTAATAATA TTGTATTATC TCTAATATTA     780

TGGTATAATA GATACTGTGA AAATAAATTC AACTGGAGAT AAGGAAACCA TTTTGTATAG     840

ATATTTTATA CAAATTATTA TGAAATAATC TAAATAAATG ACAAAAAATC GATTATACAA     900

ATCACATTAA TGACAAACAA ACTTGTATAC ATATATTGAT TAACATTACA AAACTAAATT     960

ATAATATTTA GATTGATAAT TGTTATAATA CTTAACAATA TTCTACTTTT TAATATAATT    1020

TTTTATTCAA TAATATACTC TTTCATATTT TGTACTATTT TATATAATCA TATATATTAT    1080

ATAATTATAT ATATTTGATA ATTGAATATA TCAATAATGA TGATATACAT GAATATGCAT    1140

ATATACCCCA TATAATGTTA TTATATTTAG TGCTTACATT ATTAATTATA AATATATTTA    1200

AATAATTAAA TAATAATGAA AATTAACATA GACAATATAA TATTAATCAA TTTGATAATA    1260

TTATTGAATC GTAATGTAGT ATATTGTGTG GATAAAAATG ATGTTTCATT ATGGAAATCA    1320

AAACCTATAA CAACTGTCAG TACCACTAAT GATACTATTA CAAATAAATA CACTAGTACT    1380

GTAATTAATG CCAATTTTGC TAGCTACCGT GAATTTGAGG ATAGGGAACC TTTAACAATA    1440

GGATTTGAAT ACATGATCGA TAAATCACAA CAAGATAAAT TATCACATCC AAATAAAATT    1500

GATAAAATCA AAATTTCTGA TTATATAATT GAATTTGATG ACAATGCTAA ATTACCAACT    1560

GGTAGTGTTA ATGATATATC CATCATTACT TGCAAGCATA ATAATCCAGT ATTAATTAGA    1620

TTCTCATGTT TAATAGAAGG ATCTATCTGC TATTATTTCT ACTTATTGAA TAATGATACA    1680

AATAAATGGA ATAATCACAA ATTAAAATAT GATAAAACAT ACAATGAACA TACTGACAAT    1740

AATGGTATTA ATTATTATAA AATCGATTAT AGTGAATCTA CAGAACCTAC TACCGAATCT    1800

ACTACCTGTT TTTGTTTTCG CAAAAAAAAT CATAAATCTG AGCGTAAAGA ATTAGAAAAT    1860
```

-continued

```
TATAAATATG AGGGTACAGA ATTAGCAAGA ATACATTGTA ATAAAGGGAA ATGTGTAAAA    1920

TTGGGTGACA TTAAGATAAA GGATAAGAAT TTGGAAATTT ATGTGAAACA GTTAATGTCT    1980

GTAAATACTC CAGTAAATTT TGACAACCCT ACATCGATTA ATCTACCAAC TGTCAGTACT    2040

ACCAATGATA CTATTACAAA TAAATACACT GGTACTATAA TTAATGCCAA TATTGTTGAG    2100

TACTGTGAAT TTGAGGATGA ACCTTTAACA ATAGGGTTTA GATACACTAT AGATAAATCA    2160

CAACAAAATA AATTATCACA TCCAAATAAA ATTGATAAAA TCAAATTTTT TGATTATATA    2220

ATTGAATTTG ATGATGATGT TAAATTACCA ACAATTGGTA CTGTCAATAT TATATATATC    2280

TATACTTGCG AGCATAATAA TCCAGTATTA GTTGAATTTA TAGTTTCTAT AGAAGAATCT    2340

TACTACTTTT ACTTCTACTC AATGAATAAT AATACAAATA AATGGAATAA TCACAAATTA    2400

AAATATGATA AAAGATTCAA AAAATATACT AAGAATGGTA TTAATTGTTA TGAATATGTA    2460

CTTCGTAAAT GCAGTTCTTA TACTCGTAAA AATGAATATG AGCATAAAGA ATTAGCAAGA    2520

ATACATTGTA ATGAAGAAAA ATGTGTAAAT GTAAAGGTAG ATAACATTGA GAAAAAGAAT    2580

TTGGAAATTT ATGTAAAATA ATTTAACGAA GTGTAATATG TAAAATAGTT TAATGAAGTA    2640

TAATATTATT TAAAATAATT CAAAATTTCA GAAATTAATA TAATTAATTA TTATAAATAC    2700

AAAATAATTA ATTACAAATG TGTATTGTTA GTTATTTCAG ATTGTAAATA CATATTTTAC    2760

ATACATTTTT ATTAAAACTT TCAAATTAAT ATTTTCATTT TTATAAGCAT TATTATAATT    2820

ATATACTATA ATTATCAGTC ATCAAATAAT ATCCAAAGTT ATCCTCTACA TTATATCAAT    2880

CATACAGTAT ACAATTATAT AAAATATTAA CAACATATAA CAACCAACAT TAATATATAC    2940

ATAATATCTT TATTAATCAA TATTTAATCA ATACAATAAT TAATAGTTAA CTAACTATAC    3000

ACATAGTGTA TACTAAATTA TTATAAATTA TATGTTATAA TTACAAAAAC GTCATTTACT    3060

TATTTTATTT CAGTTATGTT TCATAGTCTA ATTTAGATTT GGTGAAACGC ATCTGGCTGA    3120

TGTGCTGGTG AGCAAGCAGT TCCACGAAGC AAACAATATG ACTGATGCGC TGGCGGCGCT    3180

TTCTGCGGCG GTTGCCGCAC AGCTGCCTTG CCGTGACGCG CTGATGCAGG AGTACGACGA    3240

CAAGTGGCAT CAGAACGGTC TGGTGATGGA TAAATGGTTT ATCCTGCAAG CCACCAGCCC    3300

GGCGGCGAAT GTGCTGGAGA CGGTGCGCGG CCTGTTGCAG CATCGCTCAT TTACCATGAG    3360

CAACCCCGAA CCGTATTCGT TCGTTGATTG GCGCGTTTGC GGGCAGCAAT CCGGCAGCGT    3420

TCCATGCCGA AGATGGCAGC GGTTACCTGT TCCTGGTGGA AATGCTTACC GACCTCAACA    3480

GCCGTAACCC GCAGGTGGCT TCACGTCTGA TTGAACCGCT GATTCGCCTG AAACGTTACG    3540

ATGCCAAACG TCAGGAGAAA ATGCGCGCGG CGCTGGAACA GTTGAAAGGG CTGGAAAATC    3600

TCTCTGGCGA TCTGTACGAG AAGATAACTA AAGCACTGGC TTGATAAAATA ACCGAATGGC    3660

GGCAATAGCG CCGCCATTCG GGGAATTTAC CCCTGTTTTC T                        3701
```

(2) INFORMATION FOR SEQ ID NO:11:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (xi) SEQUENCE DESCRIPTION: SEQ ID NO:11:

```
CTCGTGCCGC TCGTGCCGAT TATTATAAAT ATTTAGTTGA TGAATATAGT TCTCCCAGGG     60

AGGAAAGAGA ATTAGCAAGA GTACATTGTA ATGAAGAAAA ATGTGTAAAA TTGGATGGCA    120

TTAAGTTTAA GGATAAGAAT TTGGAAATTT ATGTGAAACA GTTAATGTCT GTAAATACTC    180
```

| | |
|---|---|
| CAGTTGTATT TGACAACAAT ACATTGATTA ATCCAACTAG CAGCAGTGGT GCCACTGATG | 240 |
| ACATAACATA TGAATTATCG GTGGAATCAC AACCTGTACC AACTAACATT GACACAGGTA | 300 |
| ATAATATTAC AACAAATACA TCAAATAATA ATCTAATTAA AGCTAAATTT CTTTATAATT | 360 |
| TTAATCTTCC TGGTAAACCT TCAACAGGAC TATTTGAATA CACTATAGAT AAATCAGAAC | 420 |
| AAAATAAATT ATCACATCCA AATAAAATTG ATAAAATCAA ATTTTCTGAT TATATAATTG | 480 |
| AATTTGATGA TGATGCTAAA TTACCAACAA TTGGTACTGT CAATATTATA TCCATCATTA | 540 |
| CTTGCAAGCA TAATAATCCA GTATTAGTTG AATTTATAGT TTCTACAGAA ATATATTGCT | 600 |
| ACTACAATTA CTTCTACTCA ATGAATAATA ATACAAATAA ATGGAATAAT CACAAATTAA | 660 |
| AATATGATAA AAGATATAAA GAAGAATATA CAGATGATAA TGGTATTAAT TATTATAAAT | 720 |
| TAAATGATAG TGAACCTACT GAATCTACAG AATCTACTAC CTGTTTTTGT TTTCGCAAAA | 780 |
| AAAATCATAA ATATGAAAAT GAGCGTACAG CATTAGCAAA AGAACATTGC AATGAAGAAA | 840 |
| GATGTGTAAA GGTAGATAAC ATTAAGGATA ATAATTTGGA AATTTATCTA AAATAATTTA | 900 |
| ACGAAGTATA ATATTATTTA TAATAATTCA AAATTTCAGA ATTAATATA ATTAATTATT | 960 |
| ATAAATACAA AATAATTAAT TACAAATGTG TATTGTTAGT TATTTCAGAT TGTAAATACA | 1020 |
| TATTTTACAT ACATTTTTAT TAAAACTTTC AAATTAATAT TTTCATTTTT ATAAGCATTA | 1080 |
| TTATAATTAT ATACTATAAT TATCAGTCAT CAAATAATAT CCAAAGTTAT CCTCTACATT | 1140 |
| ATATCAATCA TACAGTATAC AATTATATAA AATATTAACA ACATATAACA ACCAACATTA | 1200 |
| ATATATACAT AATATCTTTA TTAATCAATA TTTAATCAAT ACAATAATTA ATAGTTAACT | 1260 |
| AACTATACAC ATAGTGTATA CTAAATT | 1287 |

(2) INFORMATION FOR SEQ ID NO:12:

(i) SEQUENCE CHARACTERISTICS:
        (A) LENGTH: 572 base pairs
        (B) TYPE: nucleic acid
        (C) STRANDEDNESS: single
        (D) TOPOLOGY: linear (xi) SEQUENCE DESCRIPTION: SEQ ID NO:12:

| | |
|---|---|
| CTTCATTGAC GTCTATCCCC AATCTTAGAA AAATCTTCAA ATCGATTCTA GAATAACTGG | 60 |
| AAACAATTAT CAGAAATTGT ATAACTGCTT ATTAGCTTAT TAGCTTATTA GTTAGGATGT | 120 |
| ATGCACATTG ATGACAACTA GATGCAGCAC CACAATCACT ACCACGTACC AATCATATAC | 180 |
| CAATAATGTA CTAATAATGT ACCAATAACT ATGGTTTATA AAGATGGTGT CATTTAAATC | 240 |
| AATATTAGTT CCTTATATTA CACTCTTTTT AATGAGCGGT GCTGTCTTTG CAAGTGATAC | 300 |
| CGATCCCGAA GCTGGTGGGC CTAGTGAAGC TGGTGGGCCT AGTGAAGCTG GTGGGCCTAG | 360 |
| TGGAACTGTT GGGCCCAGTG AAGCTGGTGG GCCTAGTGAA GCTGGTGGGC CTAGTGGAAC | 420 |
| TGGTTGGCCT AGTGAAGCTG GTGGGCCTAG TGAAGCTGGG GGCCTAGTG GAACTGGTTG | 480 |
| GCCTAGTGAA GCTGGTTGGT CTAGTGAACG ATTTGGATAT CAGCTTCTTC CGTATTCTAG | 540 |
| AAGAATAGTT ACATTTAATG AAGTTTGTTT AT | 572 |

(2) INFORMATION FOR SEQ ID NO:13:

(i) SEQUENCE CHARACTERISTICS:
        (A) LENGTH: 2338 base pairs
        (B) TYPE: nucleic acid
        (C) STRANDEDNESS: single
        (D) TOPOLOGY: linear (xi) SEQUENCE DESCRIPTION: SEQ ID NO:13:

-continued

```
CTCGTGCCGA ATCTTAGAAA AATCTTCAAA TCGATTCTAG AATAACTGGA AACAATTATC      60

AGAAATTGTA TAACTGCTTA TTAGCTTATT AGCTTATTAG TTAGGATGTA TGCACATTGA     120

TGACAACTAG ATGCAGCACC ACAATCACTA CCACGTACCA ATCATATACC AATAATGTAC     180

TAATAATGTA CCAATAACTA TGGTTTATAA AGATGGTGTC ATTTAAATCA ATATTAGTTC     240

CTTATATTAC ACTCTTTTTA ATGAGCGGTG CTGTCTTTGC AAGTGATACC GATCCCGAAG     300

CTGGTGGGCC TAGTGGAACT GTTGGGCCCA GTGAAGCTGG TGGGCCTAGT GAAGCTGGTG     360

GGCCTAGTGG AACTGGTTGG CCTAGTGAAG CTGGTGGGCC TAGTGAAGCT GGTGGGCCTA     420

GTGGAACTGG TTGGCCTAGT GAAGCTGGTT GGTCTAGTGA ACGATTTGGA TATCAGCTTC     480

TTCCGTATTC TAGAAGAATA GTTACATTTA ATGAAGTTTG TTTATCTTAT ATATACAAAC     540

ATAGTGTTAT GATATTGGAA CGAGATAGGG TGAACGATGG TCATAAAGAC TACATTGAAG     600

AAAAAACCAA GGAGAAGAAT AAATTGAAAA AGAATTGGA AAAATGTTTT CCTGAACAAT     660

ATTCCCTTAT GAAGAAAGAA GAATTGGCTA GAATATTTGA TAATGCATCC ACTATCTCTT     720

CAAAATATAA GTTATTGGTT GATGAAATAT CAAACAAGGC CTATGGTACA TTGGAAGGTC     780

CAGCTGCTGA TAATTTTGAC CATTTCCGTA ATATATGGAA GTCTATTGTA CTTAAAGATA     840

TGTTTATATA TTGTGACTTA TTATTACAAC ATTTAATCTA TAAATTCTAT TATGACAATA     900

CCATTAATGA TATCAAGAAA AATTTTGACG AATCCAAATC TAAAGCTTTA GTTTTGAGGG     960

ATAAGATCAC TAAAAAGGAC GTGTATGTAA ATGATCACTA AACGGGCTCC ACATATCTAT    1020

TACTGGGGTA GATATTATAA GTTATGGATA AGTAAATTTA TGGCGATAGA TTCCAACAAA    1080

TTTGTGGTTA GTAGCGACAA TGATTATGGC TAGTGTGTGG AGTACTTATG AGTGAATGAT    1140

TGTAGTGGTG GCTAGCAGTG AGTATAGTTA GGTAATCCCT ACACACCCAT TTAAATAAGA    1200

TGCAAATAGC ATTTAAATTG ACATATATTG TGTGTATGTC CACGTTTATT GCGTTTCCAT    1260

GACGTATCTG CTGAGGTGTG TCTTGTGTAT CTAAGTACCA GACACAGCAC TTAAATTGTT    1320

ATGGGCATGA CGATGGATGT TAAAGGTTTA TACACTCCAA AGGCACGTTC TTCTGCTAGG    1380

GAAACGAGGG ACAAGTTCGA TTTTGCTATA CAAAGCAAGT TTCACTCCCT GGACTTTACA    1440

CTGGATGACT TTGATATAGG TGCATTCGTG GTAAACCTCA AAATTTACTC AGGGCGATGG    1500

TGCCCATGGG CAGGTTTTTT TGGCAAGGGA ACGACGTACC GGTTTTATTT GCGTGTTAAA    1560

ATGCATTTTT AAATCACAAC TTGTGAAGTA ATTGCCTAAT AATCACACAG AAATGGACAG    1620

GAAGCTATTT TCAAGCGGGA AATCGAATTG CACGGGCATC TGAGACATCC AAACATAGCA    1680

TGGTATGTAC ATATTTATCC AGCTTGTATA CCTGGTTCAC TAGCCCTACT ATGATATTCA    1740

TAGTGATGGA ATATTGTTAC AATGGCGATC TATTTAATTA TATGTCAAAA CATGGCCAAC    1800

TGAGTGAAGA AAGGGTATCA GAGTATACAG ATATTTACAT AGAATTTTGT TCGAAGTCAT    1860

TTGGGCCATT AGAAGCTGCC ACGACAAACG CATAGCGCAC TTGGATATTA AACCAGTAAG    1920

GTTCTATGTT ACAGAGGAGA ATATATTATT GGACCATGAA AACAGGTGTA AATTGGCGGA    1980

CTTTGGATTC TCTGCACACA TAGGGCATTT GTACCGCTCA AACGGAGTGC TCATCATCGT    2040

GGCACGCATG GTAACACGCA ATTWATGGCA GATTATTGGT CTCCGGAGCA GTGTGCCAAA    2100

CATTTGGGTC TGGGGTTGAA GTATGGGAG TATGATGAAC AAAGCGACAT ATGGGCGTTG    2160

GGCATATTGG CAGTTGAATT GTTTATTGGA TACCCTCCAT TTGGATCTAC TACTGAAGAG    2220

CCCAACAATG TGATTATGAA CAGAATCCAC ACTTACCACT GGACCAAACA TGTACTTTTA    2280

TCTATTACGC AGATTTTTGA AATGAAGAGG GAAAAACATC TACTCTCGTC GACGCCTG      2338
```

(2) INFORMATION FOR SEQ ID NO:14:

(i) SEQUENCE CHARACTERISTICS:
        (A) LENGTH: 729 base pairs
        (B) TYPE: nucleic acid
        (C) STRANDEDNESS: single
        (D) TOPOLOGY: linear (xi) SEQUENCE DESCRIPTION: SEQ ID NO:14:

```
TTGCCTGGAC CTTCTCTGTC CTAGAATTAC AGGAATTCTC TTATACTGTT TAATACAAAA    60
CACTTGGAAG AATTTCACCA ATTGCATATG AAACATGGAA TCCAAGAGAC CAAAATTTAA   120
AACCTTGAAA TAGAAGCACT TATGCCAATA TTGGAAATTA CTTAGTGAAG TGATCCAAAG   180
TACTGATTTG GTCAGAAGAC ATCACCAGGG CACTAGCTGG CCTAGTGACC TGAGTATTTG   240
TGAAAGCTGA TTTTAATGTT GAGAACATGA AGGAAGCAGT ATTGAGGTAA TGGAATCTTG   300
TAGATTATAG TAGAAGCCAA CTGAGACCAA GAAATGTACG GTAGGAATGA AATAAGGTCT   360
TGGGTGGTCA TTGCATGGAG CTGTGAAAGT GAAGCGTTGT TGGGGTATAG ATTCGCAAGT   420
CTTGGGGCAT GACTATGTGG GGTTACCAAG GTTAGGTTAA CTGAGGTGGA AGATCCACT    480
CTAAATGGGG GAGTTACCAT TTCATGTGCT GGGATCCCAG AGATGTCAAA GGAGAAAATA   540
AGCTATTGAA TAAGAGCATC TATATCCCTT GCTTCTTGGC TATGGATGTT ATGTGACTAG   600
TCATCTCTTA GTCTTACCTT CACCATTATA ACAAGATTTT CTAGAACTTT GGGTTAAATT   660
AAATCCTTTA TTCCTCACGT TGCTGTCTTA GTTACTTTCC TGTTGCTTTG ATAAAGCATT   720
CTGGCCAAG                                                           729
```

(2) INFORMATION FOR SEQ ID NO:15:

(i) SEQUENCE CHARACTERISTICS:
        (A) LENGTH: 1448 base pairs
        (B) TYPE: nucleic acid
        (C) STRANDEDNESS: single
        (D) TOPOLOGY: linear (xi) SEQUENCE DESCRIPTION: SEQ ID NO:15:

```
ACATGTTGAC TTTTGGAAAT ATACGTTTTC ATAATATAAA TCTCCCACCA TTTTCATTGG    60
GCATAATTCA CTCGATTACG GTAGAAAAGG CGATTAACTC TGAAGATTTT GACGGAATAC   120
AAACACTTTT ACAAGTGTCT ATCATTGCTA GTTACGGTCC ATCTGGCGAT TACAGTAGTT   180
TTGTGTTCAC TCCAGTTGTA ACAGCAGACA CCAACGTTTT TTACAAATTA GAGACGGATT   240
TCAAACTTGA TGTTGATGTT ATTACTAAGA CATCACTAGA ATTGCCCACA AGTGTTCCTG   300
GCTTTCACTA CACCGAAACT ATTTACCAAG GCACAGAATT GTCAAAATTT AGCAAGCCTC   360
AGTGCAAACT TAACGATCCT CCTATTACAA CAGGATCGGG GTTGCAAATA ATACATGATG   420
GTTTGAATAA TTCGACAATT ATAACCAACA AGAAGTTAA TGTGGATGGA ACAGATTTAG    480
TTTTTTTTGA ATTGCTCCCT CCATCGGATG GCATTCCCAC CTTGCGATCA AAATTATTTC   540
CCGTCCTGAA ATCAATTCCA ATGATATCTA CCGGGGTTAA TGAATTACTG TTGGAAGTAC   600
TCGAGAACCC CTCTTTCCCT AGTGCAATTA GCAATTACAC CGGACTGACA GGCCGACTTA   660
ACAAATTACT TACAGTTTTA GACGGTATTG TTGATAGCGC CATTAGTGTC AAGACTACAG   720
AAACTGTCCC TGACGACGCA GAAACTTCTA TTTCTTCATT GAAATCATTG ATAAAGGCAA   780
TACGAGATAA TATTACTACC ACTCGAAACG AAGTTACCAA AGATGATGTT TATGCATTGA   840
AGAAGGCCCT CACTTGTCTA ACGACACACC TAATATATCA TTCAAAAGTA GATGGTATAT   900
CATTCGACAT GCTGGGAACA CAAAAAAATA AATCTAGCCC ACTAGGCAAG ATCGGAACGT   960
```

| CTATGGACGA TATTATAGCC ATGTTTTCGA ATCCCAATAT GTATCTTGTG AAGGTGGCGT | 1020 |
| ACTTGCAAGC CATTGAACAC ATTTTTCTCA TATCAACCAA ATACAATGAT ATATTTGATT | 1080 |
| ACACCATTGA TTTTAGTAAG CGTGAAGCTA CTGATTCTGG ATCATTTACC GATATATTGC | 1140 |
| TCGGAAACAA GGTGAAGGAA TCTTTGTCAT TTATTGAGGG TTTGATTTCT GACATAAAAT | 1200 |
| CTCACTCATT GAAAGCTGGG GTTACAGGAG GTATATCAAG TTCATCATTA TTTGATGAAA | 1260 |
| TCTTCGACGA GTTAAATTTG GATCAAGCAA CAATTAGAAC CCTTGTTGCA CCATTAGATT | 1320 |
| GGCCACTTAT CTCAGACAAA AGCCTCCACC CTTCACTGAA GATGGTTGTG GTCCTGCCAG | 1380 |
| GATTTTTCAT AGTTCCTTAA TAACATGACA TTTCATAGTC CCTTCAGTCC TGATGACAAG | 1440 |
| ACGGTGAA | 1448 |

(2) INFORMATION FOR SEQ ID NO:16:

(i) SEQUENCE CHARACTERISTICS:
        (A) LENGTH: 1350 base pairs
        (B) TYPE: nucleic acid
        (C) STRANDEDNESS: single
        (D) TOPOLOGY: linear (xi) SEQUENCE DESCRIPTION: SEQ ID NO:16:

| GCCTAAGCCC AAATGGGATT TAAGCAGGAG GGGATAAAAC AGATGACCTC CACCATGCCC | 60 |
| TACTAACTCT AAGCTAAGGA AATCCAGCCT GCTGGCTATT TACCTGCTTT CCTCGAAGTG | 120 |
| AAAGGCCAGA GTCACCCCCA ATCTTTCCCA AAAGATTGAA GTCACTCTCT CCATGCCGGC | 180 |
| AAAGGTAGAT GGTGCGAGGC TGGACATGGA TATTCATAAG GTAGTAGACA ATTTTACTCT | 240 |
| GGATGTAGTC CTGGACTCTG TTGACCAGAA ATCTCTGGCC TACATTAATC ACCTTGATGA | 300 |
| AGACAGATCC CTAGGACAGA GTAGAAAGAG CAATTTTATG GTCAGAAAAT CTGAAACTAG | 360 |
| GAGTGTGGCA AGCAAGGGGG CAAGGCTATC AGCACCTAGT GACAATCCCA GCACTTAGAA | 420 |
| GGCTTAGCTG GAAGGGGCTT AGGTTTGACC CTGACTCAAG ACAAATGAAC ATATGAAAAG | 480 |
| TATGGGAGA ATGATCTGTG TATTGACTGG TAGGGCCTCA TCAGCTATTC CTTCTCTCCC | 540 |
| TGTCACTGCC ATCTCGTGCC GAATTCGGCA CGAGCTCGTG CCGAAACCCT AAACCCTAAA | 600 |
| CCCCTAAACC CTAAACCCTA AACCCTAAAC CCTAAACCCT AAACCCTAAA CCCTAAACCC | 660 |
| TAAACCCCTA AACCCTAAA CCCTAAACCC TAAACCCTAA ACCCTAAACC CTAAACCCTA | 720 |
| AACCCTAACC CTAACCCTAA CCCTAACCCT AACCTAGCCT TCATTGACGT CTATCCCCAA | 780 |
| TCTTAGAAGA ATCTTCAAAT CGATTCTAGA ATAACTGGAA ACAATTATCA GAAATTGTAT | 840 |
| AACTGCTTAT TAGCTTATTA GCTTATTAGT TAGGATGTAT GCACATTGAT GACAACTAGA | 900 |
| TGCAGCACCA CAATCACTAC CACGTACCAA TCATATACCA ATAATGTACT AATAATGTAC | 960 |
| CAATAACTAT GGTTTATAAA GATGGTGTCA TTTAAATCAA TATTAGTTCC TTATATTACA | 1020 |
| CTCTTTTTAA TGAGCGGTGC TGTCTTTGCA AGTGATACCG ATCCCGAAGC TGGTGGGCCT | 1080 |
| AGTGAAGCTG GTGGGCCTAG TGGAACTGTT GGGCCCAGTG AAGCTGGTGG GCCTAGTGAA | 1140 |
| GCTGGTGGGC CTAGTGGAAC TGGTTGGCCT AGTGAAGCTG GTGGGCCTAG TGAAGCTGGT | 1200 |
| GGGCCTAGTG AAGCTGGTGG GCCTAGTGAA GCTGGTGGGC CTAGTGGAAC TGGTTGGCCT | 1260 |
| AGTGGAACTG GTTGGCCTAG TGAAGCTGGT TGGTCTAGTG AACGATTTGG ATATCAGCTT | 1320 |
| CTTCCGTATT CTAGAAGAAT AGTTATATTT | 1350 |

(2) INFORMATION FOR SEQ ID NO:17:

(i) SEQUENCE CHARACTERISTICS:
    (A) LENGTH: 1820 base pairs
    (B) TYPE: nucleic acid
    (C) STRANDEDNESS: single
    (D) TOPOLOGY: linear (xi) SEQUENCE DESCRIPTION: SEQ ID NO:17:

```
GGAAAGCCTT AAACATGCAT GGGAATAATG AAATAGTAAA AATTGCAGCC ATGGCAATGT      60

AATAATGAGT GGATGTTTCA GTCTTGAGGC TCTTTAACAA GAGTGTTGTC TTGTAGTCAA     120

AGACAAAGTG ATTCGTCATG CCGCATTCGC AGCCACCATC ATCATCAGGC GACGACGGGT     180

CTCTTTCATT ATCCTCGGGC TTATTATTGC AACCATGACA CCCTTCTTTA CAAAAGTCTT     240

TTTTTTTCAG CGGTGTCTGA GTATTATGCG ATTTTATTCC AGCCTTCCCA CTTTTATTCT     300

TATTGAGATT GCCATGCTCT TCTTCATGAG CGTCACTTGT TTCCTGCGGT GTCTGAGTAT     360

CATACGATTT TATTCCAGCA TTTCCACTTT TATTCTTATT GATTTTGTCA TGCCCTTCTT     420

CACACTCTTC ACATATTTCT TGCGTTGTCT GAGTATCATG CGATTTTCTT TCAGCCTTCT     480

CACTTTTATT CGTATTGATT TTGTCATGCC CTTCTTCATG AGCGTCACTT GTTTCCTGCG     540

GTGTCTGAGT ATCATACGAT TTTATTCCAG CATTTCCACT TTTATTCTTA TTGATTTTGT     600

CATGCCCTTC TTCACACTCT TCACATATTT CTTGCGTTGT CTGAGTATCA TACGATTTTA     660

TTCCAGCATT TCCACTTTTA TTCTTATTGA TTTTGTCATG CCCTTCTTCA CACTCTTCAC     720

ATATTTCTTG CGTTGTCTGA GTATCATGCG ATTTTCTTTC AGCCTTCTCA CTTTTATTCG     780

TATTGGGTTT GCCATGCCCT TCTTTACGCT CTTCATATAT TTCTTGTGCC GTTAGTCTCA     840

GTAAGTTGTC AAGCTCTTCA TATATTTCTT GCGGTGTCTG AGTATCATGC GATTTTCTTT     900

CAGTCTTCTC ACTTTTATTC GTATTGAGTT TGCCATTCCC TTCTTCATGA TCGTCACTTG     960

TTTCTTGCGC CGTTAGTCTC ATTAAGTTGT CAAGCTCTTC ATCATCTATT GAATGGTATG    1020

GAGCTGTATC TTCCCAGGGT GGTTGAATTA TGTCATTCTC GCCGATTTTA AATGATGGTT    1080

CTTCATCATT TATATCAGAT GCCATGTCTG AGTGGTGCCC TAATCTAGAG AATTGGTGTG    1140

GTACCCCCTC ATCCAAACTT TCGGGCAACA CCCTGGTATC AGAATCCATT TGTTCGAGCG    1200

GCTCACTATC GCAAGCGTCT TGTGGATTGA TGTTATCATG TTCCTGGATT TCAACATGTA    1260

CAGATTCTGA ATCCGCATTG GGTTCTGGAA TATAGTTGGT AACTACATTT GTTTCTAGAG    1320

AAGTATCATT CTTATATTAA TTCATCTAAG ATCTGTGCTT CTTTGTTTCT ACACATACAG    1380

GGTGTCTCTT TTCCCAACAT AATATCTGTA AATTCTTCCC AGAAGCAGAA CCTTGTTGGT    1440

ACCAGACAGC ATCGGGTCTC TGTGAGTTTC TATTCAGGCA ACAGGTGTAT TCTGTTTGCC    1500

AGTCCAAGTG CATCCTGTAT TCTAGTACTG GCTTACTACC CCAAGCAAAT CACTGGCATC    1560

AACATCTAGC ACTGAGTGAA GCATGATCTC TTCTACAAGG TGTTTTTCCA TTGTGTTGTA    1620

AGCCCGTATA CAAGGCTGTT CCCACTCAAC AATGAAGAGA CCTCTTAGCA TGAATGGCCA    1680

GATGTCTGTT CTTTAAATTA AATCAATATG TTTTGCTCAA TATGTCAGAC TTGTTTGTGG    1740

TGGAGCCAAA ATTGGAGGTC CCATCGAGAT TTGGAGAAAC TTGAAATGAA TGCAAAAGAT    1800

GGTGGGGGCT ACTCGTGCCG                                                1820
```

(2) INFORMATION FOR SEQ ID NO:18:

(i) SEQUENCE CHARACTERISTICS:
    (A) LENGTH: 263 amino acids
    (B) TYPE: amino acid
    (C) STRANDEDNESS:
    (D) TOPOLOGY: linear -continued (xi) SEQUENCE DESCRIPTION: SEQ ID NO:18:

```
Leu Phe Leu Met Ser Gly Ala Val Phe Ala Ser Asp Thr Asp Pro Glu
1               5                  10                  15

Ala Gly Gly Pro Ser Glu Ala Gly Gly Pro Ser Gly Thr Val Gly Pro
            20                  25                  30

Ser Glu Ala Gly Gly Pro Ser Glu Ala Gly Gly Pro Ser Gly Thr Gly
        35                  40                  45

Trp Pro Ser Glu Ala Gly Gly Pro Ser Glu Ala Gly Gly Pro Ser Glu
    50                  55                  60

Ala Gly Gly Pro Ser Glu Ala Gly Gly Pro Ser Gly Thr Gly Trp Pro
65                  70                  75                  80

Ser Gly Thr Gly Trp Pro Ser Glu Ala Gly Trp Ser Ser Glu Arg Phe
                85                  90                  95

Gly Tyr Gln Leu Leu Pro Tyr Ser Arg Arg Ile Val Ile Phe Asn Glu
            100                 105                 110

Val Cys Leu Ser Tyr Ile Tyr Lys His Ser Val Met Ile Leu Glu Arg
            115                 120                 125

Asp Arg Val Asn Asp Gly His Lys Asp Tyr Ile Glu Glu Lys Thr Lys
        130                 135                 140

Glu Lys Asn Lys Leu Lys Lys Glu Leu Glu Lys Cys Phe Pro Glu Gln
145                 150                 155                 160

Tyr Ser Leu Met Lys Lys Glu Glu Leu Ala Arg Ile Phe Asp Asn Ala
                165                 170                 175

Ser Thr Ile Ser Ser Lys Tyr Lys Leu Leu Val Asp Glu Ile Ser Asn
            180                 185                 190

Lys Ala Tyr Gly Thr Leu Glu Gly Pro Ala Ala Asp Asn Phe Asp His
        195                 200                 205

Phe Arg Asn Ile Trp Lys Ser Ile Val Leu Lys Asp Met Phe Ile Tyr
    210                 215                 220

Cys Asp Leu Leu Leu Gln His Leu Ile Tyr Lys Phe Tyr Tyr Asp Asn
225                 230                 235                 240

Thr Val Asn Asp Ile Lys Lys Asn Phe Asp Glu Ser Lys Ser Lys Ala
                245                 250                 255

Leu Val Leu Arg Asp Lys Ile
            260
```

(2) INFORMATION FOR SEQ ID NO:19:

(i) SEQUENCE CHARACTERISTICS:
        (A) LENGTH: 310 amino acids
        (B) TYPE: amino acid
        (C) STRANDEDNESS:
        (D) TOPOLOGY: linear (xi) SEQUENCE DESCRIPTION: SEQ ID NO:19:

```
Met Ser Gly Ala Val Phe Ala Ser Asp Thr Asp Pro Glu Ala Gly Gly
1               5                  10                  15

Pro Ser Glu Ala Gly Gly Pro Ser Gly Thr Val Gly Pro Ser Glu Ala
            20                  25                  30

Gly Gly Pro Ser Glu Ala Gly Gly Pro Ser Gly Thr Val Gly Pro Ser
        35                  40                  45

Glu Ala Gly Gly Pro Ser Glu Ala Gly Gly Pro Ser Gly Thr Gly Trp
    50                  55                  60

Pro Ser Glu Ala Gly Gly Pro Ser Glu Ala Gly Gly Pro Ser Gly Thr
65                  70                  75                  80
```

```
Val Gly Pro Ser Glu Ala Gly Gly Pro Ser Glu Ala Gly Gly Pro Ser
                 85                  90                  95

Gly Thr Gly Trp Pro Ser Glu Ala Gly Gly Pro Ser Glu Ala Gly Gly
                100                 105                 110

Pro Ser Glu Ala Gly Gly Pro Ser Glu Ala Gly Gly Pro Ser Gly Thr
                115                 120                 125

Gly Trp Pro Ser Gly Thr Gly Trp Pro Ser Glu Ala Gly Trp Ser Ser
130                 135                 140

Glu Arg Phe Gly Tyr Gln Leu Leu Pro Tyr Ser Arg Arg Ile Val Ile
145                 150                 155                 160

Phe Asn Glu Val Cys Leu Ser Tyr Ile Tyr Lys His Ser Val Met Ile
                165                 170                 175

Leu Glu Arg Asp Arg Val Asn Asp Gly His Lys Asp Tyr Ile Glu Glu
                180                 185                 190

Lys Thr Lys Glu Lys Asn Lys Leu Lys Lys Glu Leu Glu Lys Cys Phe
                195                 200                 205

Pro Glu Gln Tyr Ser Leu Met Lys Lys Glu Glu Leu Ala Arg Ile Phe
                210                 215                 220

Asp Asn Ala Ser Thr Ile Ser Ser Lys Tyr Lys Leu Leu Val Asp Glu
225                 230                 235                 240

Ile Ser Asn Lys Ala Tyr Gly Thr Leu Glu Gly Pro Ala Ala Asp Asn
                245                 250                 255

Phe Asp His Phe Arg Asn Ile Trp Lys Ser Ile Val Leu Lys Asp Met
                260                 265                 270

Phe Ile Tyr Cys Asp Leu Leu Leu Gln His Leu Ile Tyr Lys Phe Tyr
                275                 280                 285

Tyr Asp Asn Thr Val Asn Asp Ile Lys Lys Asn Phe Asp Glu Ser Trp
290                 295                 300

Thr Gln Thr Leu Lys Glu
305                 310

(2) INFORMATION FOR SEQ ID NO:20:

(i) SEQUENCE CHARACTERISTICS:
        (A) LENGTH: 367 amino acids
        (B) TYPE: amino acid
        (C) STRANDEDNESS:
        (D) TOPOLOGY: linear (xi) SEQUENCE DESCRIPTION: SEQ ID NO:20:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Glu Ala Gly Gly Pro Ser Gly Thr Val
                35                  40                  45

Gly Pro Ser Glu Ala Gly Gly Pro Ser Glu Ala Gly Gly Pro Ser Gly
50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Gly Thr Gly Trp Pro Ser Glu Ala Gly Trp Ser Ser Glu
                100                 105                 110

Arg Phe Gly Tyr Gln Leu Leu Pro Tyr Ser Arg Arg Ile Val Ile Phe
                115                 120                 125
```

```
Asn Glu Val Cys Leu Ser Tyr Ile Tyr Lys His Ser Val Met Ile Leu
    130                 135                 140
Glu Arg Asp Arg Val Asn Asp Gly His Lys Asp Tyr Ile Glu Glu Lys
145                 150                 155                 160
Thr Lys Glu Lys Asn Lys Leu Lys Lys Glu Leu Glu Lys Cys Phe Pro
                165                 170                 175
Glu Gln Tyr Ser Leu Met Lys Lys Glu Leu Ala Arg Ile Phe Asp
            180                 185                 190
Asn Ala Ser Thr Ile Ser Ser Lys Tyr Lys Leu Leu Val Asp Glu Ile
            195                 200                 205
Ser Asn Lys Ala Tyr Gly Thr Leu Glu Gly Pro Ala Ala Asp Asn Phe
    210                 215                 220
Asp His Phe Arg Asn Ile Trp Lys Ser Ile Val Leu Lys Asp Met Phe
225                 230                 235                 240
Ile Tyr Cys Asp Leu Leu Leu Gln His Leu Ile Tyr Lys Phe Tyr Tyr
                245                 250                 255
Asp Asn Thr Val Asn Asp Ile Lys Lys Asn Phe Asp Glu Ser Lys Ser
            260                 265                 270
Lys Ala Leu Val Leu Arg Asp Lys Ile Thr Lys Lys Asp Gly Asp Tyr
    275                 280                 285
Asn Thr His Phe Glu Asp Met Ile Lys Glu Leu Asn Ser Ala Ala Glu
    290                 295                 300
Glu Phe Asn Lys Ile Val Asp Ile Met Ile Ser Asn Ile Gly Asp Tyr
305                 310                 315                 320
Asp Glu Tyr Asp Ser Ile Ala Ser Phe Lys Pro Phe Leu Ser Met Ile
                325                 330                 335
Thr Glu Ile Thr Lys Ile Thr Lys Val Ser Asn Val Ile Ile Pro Gly
            340                 345                 350
Ile Lys Ala Leu Thr Leu Thr Val Phe Leu Ile Phe Ile Thr Lys
    355                 360                 365

(2) INFORMATION FOR SEQ ID NO:21:

(i) SEQUENCE CHARACTERISTICS:
        (A) LENGTH: 492 amino acids
        (B) TYPE: amino acid
        (C) STRANDEDNESS:
        (D) TOPOLOGY: linear (xi) SEQUENCE DESCRIPTION: SEQ ID NO:21:

Met Tyr Lys Ile Lys Ile Ser Asp Tyr Ile Ile Glu Phe Asp Asp Asn
1               5                   10                  15
Ala Lys Leu Pro Thr Asp Asn Val Ile Gly Ile Ser Ile Tyr Thr Cys
            20                  25                  30
Glu His Asn Asn Pro Val Leu Ile Glu Phe Tyr Val Ser Lys Lys Gly
        35                  40                  45
Ser Ile Cys Tyr Tyr Phe Tyr Ser Met Asn Asn Asp Thr Asn Lys Trp
50                  55                  60
Asn Asn His Lys Ile Lys Tyr Asp Lys Arg Phe Asn Glu His Thr Asp
65                  70                  75                  80
Met Asn Gly Ile His Tyr Tyr Ile Asp Gly Ser Leu Leu Ala Ser
                85                  90                  95
Gly Glu Val Thr Ser Asn Phe Arg Tyr Ile Ser Lys Glu Tyr Glu Tyr
            100                 105                 110
Glu His Thr Glu Leu Ala Lys Glu His Cys Lys Lys Glu Lys Cys Val
```

```
              115                 120                 125
Asn Val Asp Asn Ile Glu Asp Asn Leu Lys Ile Tyr Ala Lys Gln
    130                 135                 140

Phe Lys Ser Val Val Thr Thr Pro Ala Asp Val Ala Gly Val Ser Asp
145                 150                 155                 160

Gly Phe Phe Ile Arg Gly Gln Asn Leu Gly Ala Val Gly Ser Val Asn
                165                 170                 175

Glu Gln Pro Asn Thr Val Gly Met Ser Leu Glu Gln Phe Ile Lys Asn
            180                 185                 190

Glu Leu Tyr Ser Phe Ser Asn Glu Ile Tyr His Thr Ile Ser Ser Gln
        195                 200                 205

Ile Ser Asn Ser Phe Leu Ile Met Met Ser Asp Ala Ile Val Lys His
    210                 215                 220

Asp Asn Tyr Ile Leu Lys Lys Glu Gly Glu Gly Cys Glu Gln Ile Tyr
225                 230                 235                 240

Asn Tyr Glu Glu Phe Ile Glu Lys Leu Arg Gly Ala Arg Ser Glu Gly
                245                 250                 255

Asn Asn Met Phe Gln Glu Ala Leu Ile Arg Phe Arg Asn Ala Ser Ser
            260                 265                 270

Glu Glu Met Val Asn Ala Ala Ser Tyr Leu Ser Ala Ala Leu Phe Arg
        275                 280                 285

Tyr Lys Glu Phe Asp Asp Glu Leu Phe Lys Lys Ala Asn Asp Asn Phe
    290                 295                 300

Gly Arg Asp Asp Gly Tyr Asp Phe Asp Tyr Ile Asn Thr Lys Lys Glu
305                 310                 315                 320

Leu Val Ile Leu Ala Ser Val Leu Asp Gly Leu Asp Leu Ile Met Glu
                325                 330                 335

Arg Leu Ile Glu Asn Phe Ser Asp Val Asn Asn Thr Asp Asp Ile Lys
            340                 345                 350

Lys Ala Phe Asp Glu Cys Lys Ser Asn Ala Ile Ile Leu Lys Lys Lys
        355                 360                 365

Ile Leu Asp Asn Asp Glu Asp Tyr Lys Ile Asn Phe Arg Glu Met Val
    370                 375                 380

Asn Glu Val Thr Cys Ala Asn Thr Lys Phe Glu Ala Leu Asn Asp Leu
385                 390                 395                 400

Ile Ile Ser Asp Cys Glu Lys Lys Gly Ile Lys Ile Asn Arg Asp Val
                405                 410                 415

Ile Ser Ser Tyr Lys Leu Leu Leu Ser Thr Ile Thr Tyr Ile Val Gly
            420                 425                 430

Ala Gly Val Glu Ala Val Thr Val Ser Val Ser Ala Thr Ser Asn Gly
        435                 440                 445

Thr Glu Ser Gly Gly Ala Gly Ser Gly Thr Gly Thr Ser Val Ser Ala
    450                 455                 460

Thr Ser Thr Leu Thr Gly Asn Gly Gly Thr Glu Ser Gly Gly Thr Ala
465                 470                 475                 480

Gly Thr Thr Thr Ser Ser Gly Thr Trp Phe Gly Lys
                485                 490

(2) INFORMATION FOR SEQ ID NO:22:

(i) SEQUENCE CHARACTERISTICS:
        (A) LENGTH: 138 amino acids
        (B) TYPE: amino acid
        (C) STRANDEDNESS:
        (D) TOPOLOGY: linear
```

(xi) SEQUENCE DESCRIPTION: SEQ ID NO:22:

Ser Leu Gly Gln Pro Ala Ser Leu Gly Gln Pro Ala Ser Leu Gly Gln
1               5                   10                  15

Pro Ala Ser Leu Gly Gln Pro Ala Ser Leu Gly Gln Pro Ala Ser Leu
            20                  25                  30

Gly Gln Pro Val Pro Leu Gly Pro Ala Ser Leu Gly Pro Pro Ala
        35                  40                  45

Ser Leu Gly Pro Pro Ala Ser Leu Gly Gln Pro Val Pro Leu Gly Pro
50                      55                  60

Pro Ala Ser Leu Gly Pro Pro Ala Ser Leu Gly Pro Pro Ala Ser Leu
65                  70                  75                  80

Gly Pro Pro Ala Ser Leu Gly Pro Pro Ala Ser Leu Gly Pro Pro Ala
                85                  90                  95

Ser Leu Gly Pro Pro Ala Ser Leu Gly Pro Pro Ala Ser Leu Gly Pro
            100                 105                 110

Thr Val Pro Leu Gly Pro Pro Ala Ser Arg Ser Val Ser Pro Ala Lys
            115                 120                 125

Thr Ala Pro Leu Ile Lys Lys Ser Val Ile
130                 135

(2) INFORMATION FOR SEQ ID NO:23:

(i) SEQUENCE CHARACTERISTICS:
        (A) LENGTH: 303 amino acids
        (B) TYPE: amino acid
        (C) STRANDEDNESS:
        (D) TOPOLOGY: linear (xi) SEQUENCE DESCRIPTION: SEQ ID NO:23:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
            35                  40                  45

Gly Pro Ser Glu Ala Gly Gly Pro Ser Glu Ala Gly Gly Pro Ser Glu
50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Glu Ala Gly Trp Pro Ser Glu Ala Gly Trp Pro Ser Glu
            100                 105                 110

Ala Gly Trp Pro Ser Glu Ala Gly Trp Pro Ser Glu Ala Gly Trp Pro
            115                 120                 125

Ser Glu Arg Phe Gly Tyr Gln Leu Leu Trp Tyr Ser Arg Arg Ile Val
            130                 135                 140

Ile Phe Asn Glu Ile Tyr Leu Ser His Ile Tyr Glu His Ser Val Met
145                 150                 155                 160

Ile Leu Glu Arg Asp Arg Val Asn Asp Gly His Lys Asp Tyr Ile Glu
            165                 170                 175

Glu Lys Thr Lys Glu Lys Asn Lys Leu Lys Lys Glu Leu Glu Lys Cys
            180                 185                 190

Phe Pro Glu Gln Tyr Ser Leu Met Lys Lys Glu Glu Leu Ala Arg Ile
            195                 200                 205

```
Ile Asp Asn Ala Ser Thr Ile Ser Ser Lys Tyr Lys Leu Leu Val Asp
    210                 215                 220

Glu Ile Ser Asn Lys Ala Tyr Gly Thr Leu Glu Gly Pro Ala Ala Asp
225                 230                 235                 240

Asp Phe Asp His Phe Arg Asn Ile Trp Lys Ser Ile Val Pro Lys Asn
                245                 250                 255

Met Phe Leu Tyr Cys Asp Leu Leu Lys His Leu Ile Arg Lys Phe
                260                 265                 270

Tyr Cys Asp Asn Thr Ile Asn Asp Ile Lys Lys Asn Phe Asp Asp Ile
            275                 280                 285

Glu Lys Leu Gly Cys Phe Gln Ala Arg Ser Phe Leu Pro Val Asn
290                 295                 300
```

(2) INFORMATION FOR SEQ ID NO:24:

(i) SEQUENCE CHARACTERISTICS:
        (A) LENGTH: 592 amino acids
        (B) TYPE: amino acid
        (C) STRANDEDNESS: single
        (D) TOPOLOGY: linear (xi) SEQUENCE DESCRIPTION: SEQ ID NO:24:

```
Met Met Lys Phe Asn Ile Asp Lys Ile Ile Leu Ile Asn Leu Ile Val
1               5                   10                  15

Leu Leu Asn Arg Asn Val Val Tyr Cys Val Asp Thr Asn Asn Ser Ser
                20                  25                  30

Leu Ile Glu Ser Gln Pro Val Thr Thr Asn Ile Asp Thr Asp Asn Thr
            35                  40                  45

Ile Thr Thr Asn Lys Tyr Thr Gly Thr Ile Ile Asn Ala Asn Ile Val
        50                  55                  60

Glu Tyr Arg Glu Phe Glu Asp Glu Pro Leu Thr Ile Gly Phe Arg Tyr
65                  70                  75                  80

Thr Ile Asp Lys Ser Gln Gln Asn Lys Leu Ser His Pro Asn Lys Ile
                85                  90                  95

Asp Lys Ile Lys Phe Ser Asp Tyr Ile Ile Glu Phe Asp Asp Asn Ala
                100                 105                 110

Lys Leu Pro Thr Asp Asn Val Ile Cys Ile Ser Ile Tyr Thr Cys Lys
            115                 120                 125

His Asn Asn Pro Val Leu Ile Arg Phe Ser Cys Ser Ile Glu Lys Tyr
        130                 135                 140

Tyr Tyr His Tyr Phe Tyr Ser Met Asn Asn Asp Thr Asn Lys Trp Asn
145                 150                 155                 160

Asn His Lys Leu Lys Tyr Asp Lys Thr Tyr Asn Glu Tyr Thr Asp Asn
                165                 170                 175

Asn Gly Val Asn Tyr Tyr Lys Ile Tyr Tyr Ser Asp Lys Gln Asn Ser
                180                 185                 190

Pro Thr Asn Gly Asn Glu Tyr Glu Asp Val Ala Leu Ala Arg Ile His
            195                 200                 205

Cys Asn Glu Glu Arg Cys Ala Asn Val Lys Val Asp Lys Ile Lys Tyr
        210                 215                 220

Lys Asn Leu Glu Ile Tyr Val Lys Gln Leu Gly Thr Ile Ile Asn Ala
225                 230                 235                 240

Asn Ile Val Glu Tyr Leu Val Phe Glu Asp Glu Pro Leu Thr Ile Gly
                245                 250                 255

Phe Arg Tyr Thr Ile Asp Lys Ser Gln Gln Asn Glu Leu Ser His Pro
```

```
                 260                 265                 270
Asn Lys Ile Tyr Lys Ile Lys Phe Ser Asp Tyr Ile Ile Glu Phe Asp
            275                 280                 285

Asp Asp Ala Lys Leu Thr Thr Ile Gly Thr Val Glu Asp Ile Thr Ile
        290                 295                 300

Tyr Thr Cys Lys His Asn Asn Pro Val Leu Ile Arg Phe Ser Cys Ser
305                 310                 315                 320

Ile Glu Lys Tyr Tyr Tyr Tyr Phe Tyr Ser Met Asn Asn Asn Thr
                325                 330                 335

Asn Lys Trp Asn Asn His Asn Leu Lys Tyr Asp Asn Arg Phe Lys Glu
            340                 345                 350

His Ser Asp Lys Asn Gly Ile Asn Tyr Tyr Glu Ile Ser Ala Phe Lys
        355                 360                 365

Trp Ser Phe Ser Cys Phe Phe Val Asn Lys Tyr Glu His Lys Glu Leu
    370                 375                 380

Ala Arg Ile His Cys Asn Glu Glu Arg Cys Ala Asn Val Lys Val Asp
385                 390                 395                 400

Lys Ile Lys Tyr Lys Asn Leu Glu Ile Tyr Val Lys Gln Leu Gly Thr
                405                 410                 415

Ile Ile Asn Ala Asn Ile Val Glu Tyr Leu Val Phe Glu Asp Glu Pro
            420                 425                 430

Leu Thr Ile Gly Phe Arg Tyr Thr Ile Asp Lys Ser Gln Gln Asn Glu
        435                 440                 445

Leu Ser His Pro Asn Lys Ile Tyr Lys Ile Lys Phe Ser Asp Tyr Ile
    450                 455                 460

Ile Glu Phe Asp Asp Ala Lys Leu Thr Thr Ile Gly Thr Val Glu
465                 470                 475                 480

Asp Ile Thr Ile Tyr Thr Cys Lys His Asn Asn Pro Val Leu Ile Arg
                485                 490                 495

Phe Ser Cys Ser Ile Glu Lys Tyr Tyr Tyr Tyr Phe Tyr Ser Met
            500                 505                 510

Asn Asn Asn Thr Asn Lys Trp Asn Asn His Asn Leu Lys Tyr Asp Asn
        515                 520                 525

Arg Phe Lys Glu His Ser Asp Lys Asn Gly Ile Asn Tyr Tyr Glu Ile
    530                 535                 540

Ser Ala Phe Lys Trp Ser Phe Ser Cys Phe Phe Val Asn Lys Tyr Glu
545                 550                 555                 560

His Lys Glu Leu Ala Arg Ile His Cys Asn Glu Glu Lys Cys Val Asn
                565                 570                 575

Val Lys Val Asp Asn Ile Gly Asn Lys Asn Leu Glu Ile Tyr Val Lys
            580                 585                 590
```

(2) INFORMATION FOR SEQ ID NO:25:

(i) SEQUENCE CHARACTERISTICS:
        (A) LENGTH: 463 amino acids
        (B) TYPE: amino acid
        (C) STRANDEDNESS: single
        (D) TOPOLOGY: linear (xi) SEQUENCE DESCRIPTION: SEQ ID NO:25:

```
Ile Ile Met Lys Ile Asn Ile Asp Asn Ile Ile Leu Ile Asn Leu Ile
1               5                   10                  15

Ile Leu Leu Asn Arg Asn Val Val Tyr Cys Val Asp Lys Asn Asp Val
            20                  25                  30
```

-continued

```
Ser Leu Trp Lys Ser Lys Pro Ile Thr Thr Val Ser Thr Thr Asn Asp
        35                  40                  45

Thr Ile Thr Asn Lys Tyr Thr Ser Val Ile Asn Ala Asn Phe Ala
     50                  55                  60

Ser Tyr Arg Glu Phe Glu Asp Arg Glu Pro Leu Thr Ile Gly Phe Glu
 65                  70                  75                  80

Tyr Met Ile Asp Lys Ser Gln Gln Asp Lys Leu Ser His Pro Asn Lys
                 85                  90                  95

Ile Asp Lys Ile Lys Ile Ser Asp Tyr Ile Ile Glu Phe Asp Asp Asn
                100                 105                 110

Ala Lys Leu Pro Thr Gly Ser Val Asn Asp Ile Ser Ile Ile Thr Cys
            115                 120                 125

Lys His Asn Asn Pro Val Leu Ile Arg Phe Ser Cys Leu Ile Glu Gly
            130                 135                 140

Ser Ile Cys Tyr Tyr Phe Tyr Leu Leu Asn Asn Asp Thr Asn Lys Trp
145                 150                 155                 160

Asn Asn His Lys Leu Lys Tyr Asp Lys Thr Tyr Asn Glu His Thr Asp
                165                 170                 175

Asn Asn Gly Ile Asn Tyr Tyr Lys Ile Asp Tyr Ser Glu Ser Thr Glu
            180                 185                 190

Pro Thr Thr Glu Ser Thr Thr Cys Phe Cys Phe Arg Lys Lys Asn His
        195                 200                 205

Lys Ser Glu Arg Lys Glu Leu Glu Asn Tyr Lys Tyr Glu Gly Thr Glu
    210                 215                 220

Leu Ala Arg Ile His Cys Asn Lys Gly Lys Cys Val Lys Leu Gly Asp
225                 230                 235                 240

Ile Lys Ile Lys Asp Lys Asn Leu Glu Ile Tyr Val Lys Gln Leu Met
                245                 250                 255

Ser Val Asn Thr Pro Val Asn Phe Asp Asn Pro Thr Ser Ile Asn Leu
            260                 265                 270

Pro Thr Val Ser Thr Thr Asn Asp Thr Ile Thr Asn Lys Tyr Thr Gly
        275                 280                 285

Thr Ile Ile Asn Ala Asn Ile Val Glu Tyr Cys Glu Phe Glu Asp Glu
    290                 295                 300

Pro Leu Thr Ile Gly Phe Arg Tyr Thr Ile Asp Lys Ser Gln Gln Asn
305                 310                 315                 320

Lys Leu Ser His Pro Asn Lys Ile Asp Lys Ile Lys Phe Phe Asp Tyr
                325                 330                 335

Ile Ile Glu Phe Asp Asp Val Lys Leu Pro Thr Ile Gly Thr Val
            340                 345                 350

Asn Ile Ile Tyr Ile Tyr Thr Cys Glu His Asn Asn Pro Val Leu Val
    355                 360                 365

Glu Phe Ile Val Ser Ile Glu Glu Ser Tyr Tyr Phe Tyr Phe Tyr Ser
370                 375                 380

Met Asn Asn Asn Thr Asn Lys Trp Asn His Lys Leu Lys Tyr Asp
385                 390                 395                 400

Lys Arg Phe Lys Lys Tyr Thr Lys Asn Gly Ile Asn Cys Tyr Glu Tyr
                405                 410                 415

Val Leu Arg Lys Cys Ser Ser Tyr Thr Arg Lys Asn Glu Tyr Glu His
            420                 425                 430

Lys Glu Leu Ala Arg Ile His Cys Asn Glu Glu Lys Cys Val Asn Val
        435                 440                 445

Lys Val Asp Asn Ile Glu Lys Lys Asn Leu Glu Ile Tyr Val Lys
```

```
      450              455              460
```

(2) INFORMATION FOR SEQ ID NO:26:

(i) SEQUENCE CHARACTERISTICS:
        (A) LENGTH: 297 amino acids
        (B) TYPE: amino acid
        (C) STRANDEDNESS:
        (D) TOPOLOGY: linear (xi) SEQUENCE DESCRIPTION: SEQ ID NO:26:

```
Arg Ala Ala Arg Ala Asp Tyr Tyr Lys Tyr Leu Val Asp Glu Tyr Ser
1               5                   10                  15

Ser Pro Arg Glu Glu Arg Glu Leu Ala Arg Val His Cys Asn Glu Glu
            20                  25                  30

Lys Cys Val Lys Leu Asp Gly Ile Lys Phe Lys Asp Lys Asn Leu Glu
            35                  40                  45

Ile Tyr Val Lys Gln Leu Met Ser Val Asn Thr Pro Val Val Phe Asp
50                  55                  60

Asn Asn Thr Leu Ile Asn Pro Thr Ser Ser Gly Ala Thr Asp Asp
65                  70                  75                  80

Ile Thr Tyr Glu Leu Ser Val Glu Ser Gln Pro Val Pro Thr Asn Ile
                85                  90                  95

Asp Thr Gly Asn Asn Ile Thr Thr Asn Thr Ser Asn Asn Asn Leu Ile
                100                 105                 110

Lys Ala Lys Phe Leu Tyr Asn Phe Asn Leu Pro Gly Lys Pro Ser Thr
            115                 120                 125

Gly Leu Phe Glu Tyr Thr Ile Asp Lys Ser Glu Gln Asn Lys Leu Ser
130                 135                 140

His Pro Asn Lys Ile Asp Lys Ile Lys Phe Ser Asp Tyr Ile Ile Glu
145                 150                 155                 160

Phe Asp Asp Asp Ala Lys Leu Pro Thr Ile Gly Thr Val Asn Ile Ile
                165                 170                 175

Ser Ile Ile Thr Cys Lys His Asn Asn Pro Val Leu Val Glu Phe Ile
                180                 185                 190

Val Ser Thr Glu Ile Tyr Cys Tyr Tyr Asn Tyr Phe Tyr Ser Met Asn
            195                 200                 205

Asn Asn Thr Asn Lys Trp Asn Asn His Lys Leu Lys Tyr Asp Lys Arg
210                 215                 220

Tyr Lys Glu Glu Tyr Thr Asp Asp Asn Gly Ile Asn Tyr Tyr Lys Leu
225                 230                 235                 240

Asn Asp Ser Glu Pro Thr Glu Ser Thr Glu Ser Thr Thr Cys Phe Cys
                245                 250                 255

Phe Arg Lys Lys Asn His Lys Tyr Glu Asn Glu Arg Thr Ala Leu Ala
            260                 265                 270

Lys Glu His Cys Asn Glu Glu Arg Cys Val Lys Val Asp Asn Ile Lys
            275                 280                 285

Asp Asn Asn Leu Glu Ile Tyr Leu Lys
            290                 295
```

(2) INFORMATION FOR SEQ ID NO:27:

(i) SEQUENCE CHARACTERISTICS:
        (A) LENGTH: 121 amino acids
        (B) TYPE: amino acid
        (C) STRANDEDNESS:
        (D) TOPOLOGY: linear (xi) SEQUENCE DESCRIPTION: SEQ ID NO:27:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Glu Ala Gly Gly Pro Ser Glu Ala Gly
            35                  40                  45

Gly Pro Ser Gly Thr Val Gly Pro Ser Glu Ala Gly Gly Pro Ser Glu
    50                  55                  60

Ala Gly Gly Pro Ser Gly Thr Gly Trp Pro Ser Glu Ala Gly Gly Pro
65                  70                  75                  80

Ser Glu Ala Gly Gly Pro Ser Gly Thr Gly Trp Pro Ser Glu Ala Gly
                85                  90                  95

Trp Ser Ser Glu Arg Phe Gly Tyr Gln Leu Leu Pro Tyr Ser Arg Arg
                100                 105                 110

Ile Val Thr Phe Asn Glu Val Cys Leu
                115                 120

(2) INFORMATION FOR SEQ ID NO:28:

(i) SEQUENCE CHARACTERISTICS:
        (A) LENGTH: 267 amino acids
        (B) TYPE: amino acid
        (C) STRANDEDNESS:
        (D) TOPOLOGY: linear (xi) SEQUENCE DESCRIPTION: SEQ ID NO:28:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
                20                  25                  30

Pro Glu Ala Gly Gly Pro Ser Gly Thr Val Gly Pro Ser Glu Ala Gly
            35                  40                  45

Gly Pro Ser Glu Ala Gly Gly Pro Ser Gly Thr Gly Trp Pro Ser Glu
    50                  55                  60

Ala Gly Gly Pro Ser Glu Ala Gly Gly Pro Ser Gly Thr Gly Trp Pro
65                  70                  75                  80

Ser Glu Ala Gly Trp Ser Ser Glu Arg Phe Gly Tyr Gln Leu Leu Pro
                85                  90                  95

Tyr Ser Arg Arg Ile Val Thr Phe Asn Glu Val Cys Leu Ser Tyr Ile
                100                 105                 110

Tyr Lys His Ser Val Met Ile Leu Glu Arg Asp Arg Val Asn Asp Gly
                115                 120                 125

His Lys Asp Tyr Ile Glu Glu Lys Thr Lys Glu Lys Asn Lys Leu Lys
            130                 135                 140

Lys Glu Leu Glu Lys Cys Phe Pro Glu Gln Tyr Ser Leu Met Lys Lys
145                 150                 155                 160

Glu Glu Leu Ala Arg Ile Phe Asp Asn Ala Ser Thr Ile Ser Ser Lys
                165                 170                 175

Tyr Lys Leu Leu Val Asp Glu Ile Ser Asn Lys Ala Tyr Gly Thr Leu
                180                 185                 190

Glu Gly Pro Ala Ala Asp Asn Phe Asp His Phe Arg Asn Ile Trp Lys
            195                 200                 205

Ser Ile Val Leu Lys Asp Met Phe Ile Tyr Cys Asp Leu Leu Leu Gln
210                 215                 220

His Leu Ile Tyr Lys Phe Tyr Tyr Asp Asn Thr Ile Asn Asp Ile Lys
225                 230                 235                 240

Lys Asn Phe Asp Glu Ser Lys Ser Lys Ala Leu Val Leu Arg Asp Lys
            245                 250                 255

Ile Thr Lys Lys Asp Val Tyr Val Asn Asp His
            260                 265

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS:
        (D) TOPOLOGY: linear (xi) SEQUENCE DESCRIPTION: SEQ ID NO:29:

Ala Trp Thr Phe Ser Val Leu Glu Leu Gln Glu Phe Ser Tyr Thr Val
1               5                   10                  15

(2) INFORMATION FOR SEQ ID NO:30:

(i) SEQUENCE CHARACTERISTICS:
        (A) LENGTH: 465 amino acids
        (B) TYPE: amino acid
        (C) STRANDEDNESS:
        (D) TOPOLOGY: linear (xi) SEQUENCE DESCRIPTION: SEQ ID NO:30:

Met Leu Thr Phe Gly Asn Ile Arg Phe His Asn Ile Asn Leu Pro Pro
1               5                   10                  15

Phe Ser Leu Gly Ile Ile His Ser Ile Thr Val Glu Lys Ala Ile Asn
            20                  25                  30

Ser Glu Asp Phe Asp Gly Ile Gln Thr Leu Leu Gln Val Ser Ile Ile
            35                  40                  45

Ala Ser Tyr Gly Pro Ser Gly Asp Tyr Ser Ser Phe Val Phe Thr Pro
50                  55                  60

Val Val Thr Ala Asp Thr Asn Val Phe Tyr Lys Leu Glu Thr Asp Phe
65                  70                  75                  80

Lys Leu Asp Val Asp Val Ile Thr Lys Thr Ser Leu Glu Leu Pro Thr
            85                  90                  95

Ser Val Pro Gly Phe His Tyr Thr Glu Thr Ile Tyr Gln Gly Thr Glu
            100                 105                 110

Leu Ser Lys Phe Ser Lys Pro Gln Cys Lys Leu Asn Asp Pro Pro Ile
            115                 120                 125

Thr Thr Gly Ser Gly Leu Gln Ile Ile His Asp Gly Leu Asn Asn Ser
130                 135                 140

Thr Ile Thr Asn Lys Glu Val Asn Val Asp Gly Thr Asp Leu Val
145                 150                 155                 160

Phe Phe Glu Leu Leu Pro Pro Ser Asp Gly Ile Pro Thr Leu Arg Ser
            165                 170                 175

Lys Leu Phe Pro Val Leu Lys Ser Ile Pro Met Ile Ser Thr Gly Val
            180                 185                 190

Asn Glu Leu Leu Leu Glu Val Leu Glu Asn Pro Ser Phe Pro Ser Ala
            195                 200                 205

Ile Ser Asn Tyr Thr Gly Leu Thr Gly Arg Leu Asn Lys Leu Leu Thr
210                 215                 220

Val Leu Asp Gly Ile Val Asp Ser Ala Ile Ser Val Lys Thr Thr Glu
225                 230                 235                 240

```
Thr Val Pro Asp Asp Ala Glu Thr Ser Ile Ser Ser Leu Lys Ser Leu
            245                 250                 255

Ile Lys Ala Ile Arg Asp Asn Ile Thr Thr Thr Arg Asn Glu Val Thr
            260                 265                 270

Lys Asp Asp Val Tyr Ala Leu Lys Lys Ala Leu Thr Cys Leu Thr Thr
            275                 280                 285

His Leu Ile Tyr His Ser Lys Val Asp Gly Ile Ser Phe Asp Met Leu
            290                 295                 300

Gly Thr Gln Lys Asn Lys Ser Ser Pro Leu Gly Lys Ile Gly Thr Ser
305                 310                 315                 320

Met Asp Asp Ile Ile Ala Met Phe Ser Asn Pro Asn Met Tyr Leu Val
                325                 330                 335

Lys Val Ala Tyr Leu Gln Ala Ile Glu His Ile Phe Leu Ile Ser Thr
                340                 345                 350

Lys Tyr Asn Asp Ile Phe Asp Tyr Thr Ile Asp Phe Ser Lys Arg Glu
                355                 360                 365

Ala Thr Asp Ser Gly Ser Phe Thr Asp Ile Leu Leu Gly Asn Lys Val
            370                 375                 380

Lys Glu Ser Leu Ser Phe Ile Glu Gly Leu Ile Ser Asp Ile Lys Ser
385                 390                 395                 400

His Ser Leu Lys Ala Gly Val Thr Gly Gly Ile Ser Ser Ser Ser Leu
                405                 410                 415

Phe Asp Glu Ile Phe Asp Glu Leu Asn Leu Asp Gln Ala Thr Ile Arg
            420                 425                 430

Thr Leu Val Ala Pro Leu Asp Trp Pro Leu Ile Ser Asp Lys Ser Leu
            435                 440                 445

His Pro Ser Leu Lys Met Val Val Leu Pro Gly Phe Phe Ile Val
            450                 455                 460

Pro
465

(2) INFORMATION FOR SEQ ID NO:31:

(i) SEQUENCE CHARACTERISTICS:
        (A) LENGTH: 128 amino acids
        (B) TYPE: amino acid
        (C) STRANDEDNESS:
        (D) TOPOLOGY: linear (xi) SEQUENCE DESCRIPTION: SEQ ID NO:31:

Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Ser Asp Thr Asp
            20                  25                  30

Pro Glu Ala Gly Gly Pro Ser Glu Ala Gly Gly Pro Ser Gly Thr Val
            35                  40                  45

Gly Pro Ser Glu Ala Gly Gly Pro Ser Glu Ala Gly Gly Pro Ser Gly
    50                  55                  60

Thr Gly Trp Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
                85                  90                  95

Trp Pro Ser Gly Thr Gly Trp Pro Ser Glu Ala Gly Trp Ser Ser Glu
            100                 105                 110

Arg Phe Gly Tyr Gln Leu Leu Pro Tyr Ser Arg Arg Ile Val Ile Phe
            115                 120                 125
```

(2) INFORMATION FOR SEQ ID NO:32:

(i) SEQUENCE CHARACTERISTICS:
        (A) LENGTH: 245 amino acids
        (B) TYPE: amino acid
        (C) STRANDEDNESS:
        (D) TOPOLOGY: linear (xi) SEQUENCE DESCRIPTION: SEQ ID NO:32:

```
Gln Glu Cys Cys Leu Val Val Lys Asp Lys Val Ile Arg His Ala Ala
 1               5                  10                  15

Phe Ala Ala Thr Ile Ile Ile Arg Arg Arg Val Ser Phe Ile Ile
             20                  25                  30

Leu Gly Leu Ile Ile Ala Thr Met Thr Pro Phe Phe Thr Lys Val Phe
             35                  40                  45

Phe Phe Gln Arg Cys Leu Ser Ile Met Arg Phe Tyr Ser Ser Leu Pro
             50                  55                  60

Thr Phe Ile Leu Ile Glu Ile Ala Met Leu Phe Phe Met Ser Val Thr
 65                  70                  75                  80

Cys Phe Leu Arg Cys Leu Ser Ile Ile Arg Phe Tyr Ser Ser Ile Ser
             85                  90                  95

Thr Phe Ile Leu Ile Asp Phe Val Met Pro Phe Phe Thr Leu Phe Thr
            100                 105                 110

Tyr Phe Leu Arg Cys Leu Ser Ile Met Arg Phe Ser Phe Ser Leu Leu
            115                 120                 125

Thr Phe Ile Arg Ile Asp Phe Val Met Pro Phe Phe Met Ser Val Thr
            130                 135                 140

Cys Phe Leu Arg Cys Leu Ser Ile Ile Arg Phe Tyr Ser Ser Ile Ser
145                 150                 155                 160

Thr Phe Ile Leu Ile Asp Phe Val Met Pro Phe Phe Thr Leu Phe Thr
            165                 170                 175

Tyr Phe Leu Arg Cys Leu Ser Ile Ile Arg Phe Tyr Ser Ser Ile Ser
            180                 185                 190

Thr Phe Ile Leu Ile Asp Phe Val Met Pro Phe Phe Thr Leu Phe Thr
            195                 200                 205

Tyr Phe Leu Arg Cys Leu Ser Ile Met Arg Phe Ser Phe Ser Leu Leu
            210                 215                 220

Thr Phe Ile Arg Ile Gly Phe Ala Met Pro Phe Phe Thr Leu Phe Ile
225                 230                 235                 240

Tyr Phe Leu Cys Arg
            245
```

(2) INFORMATION FOR SEQ ID NO:33:

(i) SEQUENCE CHARACTERISTICS:
        (A) LENGTH: 293 amino acids
        (B) TYPE: amino acid
        (C) STRANDEDNESS:
        (D) TOPOLOGY: linear (xi) SEQUENCE DESCRIPTION: SEQ ID NO:33:

```
Thr Ala Phe Ala Ala Phe Leu Ala Phe Gly Asn Ile Ser Pro Val Leu
 1               5                  10                  15

Ser Ala Gly Gly Ser Gly Gly Asn Gly Gly Asn Gly Gly Gly His Gln
             20                  25                  30

Glu Gln Asn Asn Ala Asn Asp Ser Ser Asn Pro Thr Gly Ala Gly Gly
             35                  40                  45
```

```
Gln Pro Asn Asn Glu Ser Lys Lys Ala Val Lys Leu Asp Leu Asp
    50                  55                  60

Leu Met Lys Glu Thr Lys Asn Val Cys Thr Thr Val Asn Thr Lys Leu
65                  70                  75                  80

Val Gly Lys Ala Lys Ser Lys Leu Asn Lys Leu Glu Gly Glu Ser His
                85                  90                  95

Lys Glu Tyr Val Ala Glu Lys Thr Lys Glu Ile Asp Glu Lys Asn Lys
                100                 105                 110

Lys Phe Asn Glu Asn Leu Val Lys Ile Glu Lys Lys Lys Ile Lys
            115                 120                 125

Val Pro Ala Asp Thr Gly Ala Glu Val Asp Ala Val Asp Asp Gly Val
    130                 135                 140

Ala Gly Ala Leu Ser Asp Leu Ser Ser Asp Ile Ser Ala Ile Lys Thr
145                 150                 155                 160

Leu Thr Asp Asp Val Ser Glu Lys Val Ser Glu Asn Leu Lys Asp Asp
                165                 170                 175

Glu Ala Ser Ala Thr Glu His Thr Asp Ile Lys Glu Lys Ala Thr Leu
                180                 185                 190

Leu Gln Glu Ser Cys Asn Gly Ile Gly Thr Ile Leu Asp Lys Leu Ala
            195                 200                 205

Glu Tyr Leu Asn Asn Asp Thr Thr Gln Asn Ile Lys Lys Glu Phe Asp
    210                 215                 220

Glu Arg Lys Lys Asn Leu Thr Ser Leu Lys Thr Lys Val Glu Asn Lys
225                 230                 235                 240

Asp Glu Asp Tyr Val Asp Val Thr Met Thr Ser Lys Thr Asp Leu Ile
                245                 250                 255

Ile His Cys Leu Thr Cys Thr Asn Asp Ala His Gly Leu Phe Asp Phe
            260                 265                 270

Glu Ser Lys Ser Leu Ile Lys Gln Thr Phe Lys Leu Arg Ser Lys Asp
        275                 280                 285

Glu Gly Glu Leu Cys
    290
```

(2) INFORMATION FOR SEQ ID NO:34:

(i) SEQUENCE CHARACTERISTICS:
        (A) LENGTH: 431 amino acids
        (B) TYPE: amino acid
        (C) STRANDEDNESS:
        (D) TOPOLOGY: linear (xi) SEQUENCE DESCRIPTION: SEQ ID NO:34:

```
Gly Pro Lys Met Lys Val Asn Ser Ala Asn Leu Asp Phe Arg Trp Ala
1               5                   10                  15

Met Tyr Met Leu Asn Ser Lys Ile His Leu Ile Glu Ser Ser Leu Ile
                20                  25                  30

Asp Asn Phe Thr Leu Asp Asn Pro Ser Ala Tyr Glu Ile Leu Arg Val
            35                  40                  45

Ser Tyr Asn Ser Asn Glu Phe Gln Val Gln Ser Pro Gln Asn Ile Asn
    50                  55                  60

Asn Glu Met Glu Ser Ser Thr Pro Glu Ser Asn Ile Ile Trp Val Val
65                  70                  75                  80

His Ser Asp Val Ile Met Lys Arg Phe Asn Cys Lys Asn Arg Lys Ser
                85                  90                  95

Leu Ser Thr His Ser Leu Thr Glu Asn Asp Ile Leu Lys Phe Gly Arg
```

-continued

```
                    100                 105                 110
Ile Glu Leu Ser Val Lys Cys Ile Ile Met Gly Ala Gly Ile Thr Ala
            115                 120                 125

Ser Asp Leu Asn Leu Lys Gly Leu Gly Phe Ile Ser Pro Asp Lys Gln
130                 135                 140

Ser Thr Asn Val Cys Asn Tyr Phe Glu Asp Met His Glu Ser Tyr His
145                 150                 155                 160

Ile Leu Asp Thr Gln Arg Ala Ser Asp Cys Val Ser Asp Asp Gly Ala
            165                 170                 175

Asp Ile Asp Ile Ser Asn Phe Asp Met Val Gln Asp Gly Asn Ile Asn
            180                 185                 190

Ser Val Asp Ala Asp Ser Glu Thr Cys Met Ala Asn Ser Gly Val Thr
            195                 200                 205

Val Asn Asn Thr Glu Asn Val Ser Asn Ser Glu Asn Phe Gly Lys Leu
            210                 215                 220

Lys Ser Leu Val Ser Thr Thr Thr Pro Leu Cys Arg Ile Cys Leu Cys
225                 230                 235                 240

Gly Glu Ser Asp Pro Gly Pro Leu Val Thr Pro Cys Asn Cys Lys Gly
            245                 250                 255

Ser Leu Asn Tyr Val His Leu Glu Cys Leu Arg Thr Trp Ile Lys Gly
            260                 265                 270

Arg Leu Ser Ile Val Lys Asp Asp Ala Ser Phe Phe Trp Lys Glu
            275                 280                 285

Leu Ser Cys Glu Leu Cys Gly Lys Pro Tyr Pro Ser Val Leu Gln Val
            290                 295                 300

Asp Asp Thr Glu Thr Asn Leu Met Asp Ile Lys Lys Pro Asp Ala Pro
305                 310                 315                 320

Tyr Val Val Leu Glu Met Arg Ser Asn Ser Gly Asp Gly Cys Phe Val
            325                 330                 335

Val Ser Val Ala Lys Asn Lys Ala Ile Ile Gly Arg Gly His Glu Ser
            340                 345                 350

Asp Val Arg Leu Ser Asp Ile Ser Val Ser Arg Met His Ala Ser Leu
            355                 360                 365

Glu Leu Asp Gly Gly Lys Val Val Ile His Asp Gln Gln Ser Lys Phe
            370                 375                 380

Gly Thr Leu Val Arg Ala Lys Ala Pro Phe Ser Met Pro Ile Lys Gly
385                 390                 395                 400

Pro Ile Cys Leu Gln Val Ser Ile Phe Phe Leu Asn Leu Lys Ile Ser
            405                 410                 415

Thr His Ser Leu Thr Met Glu Arg Gly Met Glu His Val Leu Leu
            420                 425                 430
```

(2) INFORMATION FOR SEQ ID NO:35:

(i) SEQUENCE CHARACTERISTICS:
        (A) LENGTH: 6 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 1
        (D) OTHER INFORMATION: /note= "Residue can be either GLU
           or GLY"

(ix) FEATURE:
        (A) NAME/KEY: Modified-site

```
            (B) LOCATION: 2
            (D) OTHER INFORMATION: /note= "Residue can be either ALA
                or THR"

(ix) FEATURE:
            (A) NAME/KEY: Modified-site
            (B) LOCATION: 3
            (D) OTHER INFORMATION: /note= "Residue can be either GLY
                or VAL"

(ix) FEATURE:
            (A) NAME/KEY: Modified-site
            (B) LOCATION: 4
            (D) OTHER INFORMATION: /note= "Residue can be either TRP
                or GLY"

(ix) FEATURE:
            (A) NAME/KEY: Modified-site
            (B) LOCATION: 5
            (D) OTHER INFORMATION: /note= "Residue can be either PRO
                or SER"

(xi) SEQUENCE DESCRIPTION: SEQ ID NO:35:

Xaa Xaa Xaa Xaa Xaa Ser
1               5

(2) INFORMATION FOR SEQ ID NO:36:

(i) SEQUENCE CHARACTERISTICS:
            (A) LENGTH: 32 amino acids
            (B) TYPE: amino acid
            (C) STRANDEDNESS:
            (D) TOPOLOGY: linear (ix) FEATURE:
            (A) NAME/KEY: Modified-site
            (B) LOCATION: 6
            (D) OTHER INFORMATION: /note= "Residue can be either Met
                or Ile"

(ix) FEATURE:
            (A) NAME/KEY: Modified-site
            (B) LOCATION: 9
            (D) OTHER INFORMATION: /note= "Residue can be either Tyr
                or Ser"

(ix) FEATURE:
            (A) NAME/KEY: Modified-site
            (B) LOCATION: 10
            (D) OTHER INFORMATION: /note= "Residue can be either Ser
                or Phe"

(ix) FEATURE:
            (A) NAME/KEY: Modified-site
            (B) LOCATION: 12
            (D) OTHER INFORMATION: /note= "Residue can be either Leu
                or Ile"

(ix) FEATURE:
            (A) NAME/KEY: Modified-site
            (B) LOCATION: 13
            (D) OTHER INFORMATION: /note= "Residue can be Pro, Ser or
                Leu"

(ix) FEATURE:
            (A) NAME/KEY: Modified-site
            (B) LOCATION: 17
            (D) OTHER INFORMATION: /note= "Residue can be either Leu
                or Arg"

(ix) FEATURE:
            (A) NAME/KEY: Modified-site
            (B) LOCATION: 19
            (D) OTHER INFORMATION: /note= "Residue can be Glu, Asp or
                Gly"

(ix) FEATURE:
```

(A) NAME/KEY: Modified-site
              (B) LOCATION: 20
              (D) OTHER INFORMATION: /note= "Residue can be either Ile
                  or Phe"

(ix) FEATURE:
              (A) NAME/KEY: Modified-site
              (B) LOCATION: 21
              (D) OTHER INFORMATION: /note= "Residue can be either Ala
                  or Val"

(ix) FEATURE:
              (A) NAME/KEY: Modified-site
              (B) LOCATION: 23
              (D) OTHER INFORMATION: /note= "Residue can be either Leu
                  or Pro"

(ix) FEATURE:
              (A) NAME/KEY: Modified-site
              (B) LOCATION: 26
              (D) OTHER INFORMATION: /note= "Residue can be either Met
                  or Thr"

(ix) FEATURE:
              (A) NAME/KEY: Modified-site
              (B) LOCATION: 27
              (D) OTHER INFORMATION: /note= "Residue can be either Ser
                  or Leu"

(ix) FEATURE:
              (A) NAME/KEY: Modified-site
              (B) LOCATION: 28
              (D) OTHER INFORMATION: /note= "Residue can be either Val
                  or Phe"

(ix) FEATURE:
              (A) NAME/KEY: Modified-site
              (B) LOCATION: 29
              (D) OTHER INFORMATION: /note= "Residue can be either Thr
                  or Ile"

(ix) FEATURE:
              (A) NAME/KEY: Modified-site
              (B) LOCATION: 30
              (D) OTHER INFORMATION: /note= "Residue can be either Cys
                  or Tyr"

(xi) SEQUENCE DESCRIPTION: SEQ ID NO:36:

Arg Cys Leu Ser Ile Xaa Arg Phe Xaa Xaa Ser Xaa Xaa Thr Phe Ile
1               5                  10                  15

Xaa Ile Xaa Xaa Xaa Met Xaa Phe Phe Xaa Xaa Xaa Xaa Xaa Phe Leu
            20                  25                  30

(2) INFORMATION FOR SEQ ID NO:37:

(i) SEQUENCE CHARACTERISTICS:
              (A) LENGTH: 1820 base pairs
              (B) TYPE: nucleic acid
              (C) STRANDEDNESS: single
              (D) TOPOLOGY: linear (xi) SEQUENCE DESCRIPTION: SEQ ID NO:37:

CGGCACGAGT AGCCCCCACC ATCTTTTGCA TTCATTTCAA GTTTCTCCAA ATCTCGATGG      60

GACCTCCAAT TTTGGCTCCA CCACAAACAA GTCTGACATA TTGAGCAAAA CATATTGATT    120

TAATTTAAAG AACAGACATC TGGCCATTCA TGCTAAGAGG TCTCTTCATT GTTGAGTGGG    180

AACAGCCTTG TATACGGGCT ACAACACAA TGGAAAAACA CCTTGTAGAA GAGATCATGC     240

TTCACTCAGT GCTAGATGTT GATGCCAGTG ATTTGCTTGG GGTAGTAAGC CAGTACTAGA    300

ATACAGGATG CACTTGGACT GGCAAACAGA ATACACCTGT TGCCTGAATA GAAACTCACA    360

GAGACCCGAT GCTGTCTGGT ACCAACAAGG TTCTGCTTCT GGGAAGAATT TACAGATATT    420

```
ATGTTGGGAA AAGAGACACC CTGTATGTGT AGAAACAAAG AAGCACAGAT CTTAGATGAA      480

TTAATATAAG AATGATACTT CTCTAGAAAC AAATGTAGTT ACCAACTATA TTCCAGAACC      540

CAATGCGGAT TCAGAATCTG TACATGTTGA AATCCAGGAA CATGATAACA TCAATCCACA      600

AGACGCTTGC GATAGTGAGC CGCTCGAACA AATGGATTCT GATACCAGGG TGTTGCCCGA      660

AAGTTTGGAT GAGGGGGTAC CACACCAATT CTCTAGATTA GGGCACCACT CAGACATGGC      720

ATCTGATATA AATGATGAAG AACCATCATT TAAAATCGGC GAGAATGACA TAATTCAACC      780

ACCCTGGGAA GATACAGCTC CATACCATTC AATAGATGAT GAAGAGCTTG ACAACTTAAT      840

GAGACTAACG GCGCAAGAAA CAAGTGACGA TCATGAAGAA GGGAATGGCA AACTCAATAC      900

GAATAAAAGT GAGAAGACTG AAAGAAAATC GCATGATACT CAGACACCGC AAGAAATATA      960

TGAAGAGCTT GACAACTTAC TGAGACTAAC GGCACAAGAA ATATATGAAG AGCGTAAAGA     1020

AGGGCATGGC AAACCCAATA CGAATAAAAG TGAGAAGGCT GAAAGAAAAT CGCATGATAC     1080

TCAGACAACG CAAGAAATAT GTGAAGAGTG TGAAGAAGGG CATGACAAAA TCAATAAGAA     1140

TAAAAGTGGA AATGCTGGAA TAAAATCGTA TGATACTCAG ACAACGCAAG AAATATGTGA     1200

AGAGTGTGAA GAAGGGCATG ACAAAATCAA TAAGAATAAA AGTGGAAATG CTGGAATAAA     1260

ATCGTATGAT ACTCAGACAC CGCAGGAAAC AAGTGACGCT CATGAAGAAG GGCATGACAA     1320

AATCAATACG AATAAAGTG AGAAGGCTGA AGAAAATCG CATGATACTC AGACAACGCA     1380

AGAAATATGT GAAGAGTGTG AAGAAGGGCA TGACAAAATC AATAAGAATA AAAGTGGAAA     1440

TGCTGGAATA AAATCGTATG ATACTCAGAC ACCGCAGGAA ACAAGTGACG CTCATGAAGA     1500

AGAGCATGGC AATCTCAATA AGAATAAAAG TGGGAAGGCT GGAATAAAAT CGCATAATAC     1560

TCAGACACCG CTGAAAAAAA AAGACTTTTG TAAAGAAGGG TGTCATGGTT GCAATAATAA     1620

GCCCGAGGAT AATGAAAGAG ACCCGTCGTC GCCTGATGAT GATGGTGGCT GCGAATGCGG     1680

CATGACGAAT CACTTTGTCT TTGACTACAA GACAACACTC TTGTTAAAGA GCCTCAAGAC     1740

TGAAACATCC ACTCATTATT ACATTGCCAT GGCTGCAATT TTTACTATTT CATTATTCCC     1800

ATGCATGTTT AAGGCTTTCC                                                 1820

(2) INFORMATION FOR SEQ ID NO:38:

(i) SEQUENCE CHARACTERISTICS:
        (A) LENGTH: 445 amino acids
        (B) TYPE: amino acid
        (C) STRANDEDNESS:
        (D) TOPOLOGY: linear (xi) SEQUENCE DESCRIPTION: SEQ ID NO:38:

Tyr Lys Asn Asp Thr Ser Leu Glu Thr Asn Val Val Thr Asn Tyr Ile
 1               5                  10                  15

Pro Glu Pro Asn Ala Asp Ser Glu Ser Val His Val Glu Ile Gln Glu
                20                  25                  30

His Asp Asn Ile Asn Pro Gln Asp Ala Cys Asp Ser Glu Pro Leu Glu
            35                  40                  45

Gln Met Asp Ser Asp Thr Arg Val Leu Pro Glu Ser Leu Asp Glu Gly
        50                  55                  60

Val Pro His Gln Phe Ser Arg Leu Gly His His Ser Asp Met Ala Ser
65                  70                  75                  80

Asp Ile Asn Asp Glu Glu Pro Ser Phe Lys Ile Gly Glu Asn Asp Ile
                85                  90                  95

Ile Gln Pro Pro Trp Glu Asp Thr Ala Pro Tyr His Ser Ile Asp Asp
```

```
            100                 105                 110
Glu Glu Leu Asp Asn Leu Met Arg Leu Thr Ala Gln Glu Thr Ser Asp
        115                 120                 125

Asp His Glu Gly Asn Gly Lys Leu Asn Thr Asn Lys Ser Glu Lys
    130                 135                 140

Thr Glu Arg Lys Ser His Asp Thr Gln Thr Pro Gln Glu Ile Tyr Glu
145                 150                 155                 160

Glu Leu Asp Asn Leu Leu Arg Leu Thr Ala Gln Glu Ile Tyr Glu Glu
                165                 170                 175

Arg Lys Glu Gly His Gly Lys Pro Asn Thr Asn Lys Ser Glu Lys Ala
                180                 185                 190

Glu Arg Lys Ser His Asp Thr Gln Thr Thr Gln Glu Ile Cys Glu Glu
                195                 200                 205

Cys Glu Glu Gly His Asp Lys Ile Asn Lys Asn Lys Ser Gly Asn Ala
                210                 215                 220

Gly Ile Lys Ser Tyr Asp Thr Gln Thr Thr Gln Glu Ile Cys Glu Glu
225                 230                 235                 240

Cys Glu Glu Gly His Asp Lys Ile Asn Lys Asn Lys Ser Gly Asn Ala
                245                 250                 255

Gly Ile Lys Ser Tyr Asp Thr Gln Thr Pro Gln Glu Thr Ser Asp Ala
                260                 265                 270

His Glu Glu Gly His Asp Lys Ile Asn Thr Asn Lys Ser Glu Lys Ala
                275                 280                 285

Glu Arg Lys Ser His Asp Thr Gln Thr Thr Gln Glu Ile Cys Glu Glu
                290                 295                 300

Cys Glu Glu Gly His Asp Lys Ile Asn Lys Asn Lys Ser Gly Asn Ala
305                 310                 315                 320

Gly Ile Lys Ser Tyr Asp Thr Gln Thr Pro Gln Glu Thr Ser Asp Ala
                325                 330                 335

His Glu Glu Glu His Gly Asn Leu Asn Lys Asn Lys Ser Gly Lys Ala
                340                 345                 350

Gly Ile Lys Ser His Asn Thr Gln Thr Pro Leu Lys Lys Lys Asp Phe
                355                 360                 365

Cys Lys Glu Gly Cys His Gly Cys Asn Asn Lys Pro Glu Asp Asn Glu
                370                 375                 380

Arg Asp Pro Ser Ser Pro Asp Asp Gly Gly Cys Glu Cys Gly Met
385                 390                 395                 400

Thr Asn His Phe Val Phe Asp Tyr Lys Thr Thr Leu Leu Leu Lys Ser
                405                 410                 415

Leu Lys Thr Glu Thr Ser Thr His Tyr Tyr Ile Ala Met Ala Ala Ile
                420                 425                 430

Phe Thr Ile Ser Leu Phe Pro Cys Met Phe Lys Ala Phe
                435                 440                 445

(2) INFORMATION FOR SEQ ID NO:39:

(i) SEQUENCE CHARACTERISTICS:
        (A) LENGTH: 32 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 3
        (D) OTHER INFORMATION: /note= "Residue can be either Gly
            or Asp"
```

```
(ix) FEATURE:
    (A) NAME/KEY: Modified-site
    (B) LOCATION: 5
    (D) OTHER INFORMATION: /note= "Residue can be either Pro
        or Ile"

(ix) FEATURE:
    (A) NAME/KEY: Modified-site
    (B) LOCATION: 7
    (D) OTHER INFORMATION: /note= "Residue can be either Lys
        or Thr"

(ix) FEATURE:
    (A) NAME/KEY: Modified-site
    (B) LOCATION: 11
    (D) OTHER INFORMATION: /note= "Residue can be either Glu
        or Gly"

(ix) FEATURE:
    (A) NAME/KEY: Modified-site
    (B) LOCATION: 12
    (D) OTHER INFORMATION: /note= "Residue can be either Lys
        or Asn"

(ix) FEATURE:
    (A) NAME/KEY: Modified-site
    (B) LOCATION: 14
    (D) OTHER INFORMATION: /note= "Residue can be either Glu
        or Gly"

(ix) FEATURE:
    (A) NAME/KEY: Modified-site
    (B) LOCATION: 15
    (D) OTHER INFORMATION: /note= "Residue can be either Ile
        or Arg"

(ix) FEATURE:
    (A) NAME/KEY: Modified-site
    (B) LOCATION: 18
    (D) OTHER INFORMATION: /note= "Residue can be either His
        or Tyr"

(ix) FEATURE:
    (A) NAME/KEY: Modified-site
    (B) LOCATION: 23
    (D) OTHER INFORMATION: /note= "Residue can be either Thr
        or Pro"

(ix) FEATURE:
    (A) NAME/KEY: Modified-site
    (B) LOCATION: 26
    (D) OTHER INFORMATION: /note= "Residue can be either Ile
        or Thr"

(ix) FEATURE:
    (A) NAME/KEY: Modified-site
    (B) LOCATION: 27
    (D) OTHER INFORMATION: /note= "Residue can be either Cys
        or Ser"

(ix) FEATURE:
    (A) NAME/KEY: Modified-site
    (B) LOCATION: 28
    (D) OTHER INFORMATION: /note= "Residue can be either Asp
        or Glu"

(ix) FEATURE:
    (A) NAME/KEY: Modified-site
    (B) LOCATION: 29
    (D) OTHER INFORMATION: /note= "Residue can be either Glu
        or Ala"

(ix) FEATURE:
    (A) NAME/KEY: Modified-site
    (B) LOCATION: 30
    (D) OTHER INFORMATION: /note= "Residue can be either Cys
        or His"
```

(xi) SEQUENCE DESCRIPTION: SEQ ID NO:39:

Gly His Xaa Lys Xaa Asn Xaa Asn Lys Ser Xaa Xaa Ala Xaa Xaa Lys
1               5                   10                  15
Ser Xaa Asp Thr Gln Thr Xaa Gln Glu Xaa Xaa Xaa Xaa Xaa Glu Glu
            20                  25                  30

(2) INFORMATION FOR SEQ ID NO:40:

(i) SEQUENCE CHARACTERISTICS:
        (A) LENGTH: 2430 base pairs
        (B) TYPE: nucleic acid
        (C) STRANDEDNESS: single
        (D) TOPOLOGY: linear (xi) SEQUENCE DESCRIPTION: SEQ ID NO:40:

```
TGTATTGTGT AGATAAAAAT GATGTTTCAT TATGGAAATC AAAACCTATA CAACTGTCA        60

GTACCACTAA TGATACTATT ACAAATACAC ACACTACTAA TGTAATTAAT GCCAATCTTA      120

TTGGCCACTT TAATTATAAG GATAGGGAAC CTTTAACAAT AGTATTTGTA TACATGATCG      180

ATGAATCAGA ACAAAATAAA TTATCACATC CGAATAAAAT TGATAAAATC AAAATTTCTG      240

ATTATATAAT TGAATTTGAT GACAATGCTA AATTACCAAC TGGTAGTGTT ATTGATTTAA      300

ACATCTATAC TTGCAAACAT AATAATCCAG TATTAATTGA ATTTTATGTT TCTATAGAAG      360

GATCTTTCTG CTATTATTTC TCTCATTGAA TAATGATACA AATGAATGGA ATAATCACAA      420

AATAAAATAT GATAAAAAAT ATAAAGAATA TACGACATG AATGGTATTC ATTATTATTA       480

TATTGATGGT AGTTTACTTG TAAGTGGCGA AGTTACATCT AATTTTCGTT ATATTTCTAA      540

AGAATATGAA TATGAGCATA CAGGATTAGT AAAAAAATAT TGTAATGAAG AAAGATGTGT     600

AAAATTGGAT AACATTAAGA TAAAGGATAA TAATTTGGAA ATTTATGTGA AATAATTTAA      660

TGAAGTATAA TATTATTTAT AATAATTCAA AGATTAATAT AATCAATTAT TATAATTACA      720

AAAATAATTA ATTGTAGAAT ATTATATTAT TAATCAATTC AGATTATAAA TACATATTTT      780

TACATACATT TCAATTTAAA CATTCAAATT AATGTCATTT TTATCTACAT TATTATAATT      840

ATAACTATAA TATTCATTAA ATACTATTAA AAAAAATATC CTCTACATTA TATTAATTAT      900

TATAGTATGT CATTATATAA CATATTCACA ACGTATAACA AATCAATCAT TAACATATAC      960

ATATATGATA TCATTAATAA TCAATATTTA ATTGATACAA TAATCAATAG TCATCTGTAA     1020

TATAATCATT GTATACTAAT TTATTATAAA TTATTACAAA ATACACTCTT TTACTTCATT     1080

TTATTTCTGT TAAATTTCAT ATTCTAATAT TATATTCATC TTTCTCATGT TACTTTAATC     1140

TATTTCCATA TTTATCCCAA TTTCTTCATT TAAGACTGAG ATGTTCGTTC GTTCATACAT     1200

AAATAATGTG TAAATTTTGT AATATATAAT AATGTATACA TCTGGTATTA CATCTATTTT     1260

GTAATAAATA TTAAAAAAAC GGTTAAAGTT AGTGCCTTAA TTCCAGGAAT TATTACATTA     1320

GAAACTTTGG TGATTTTAGT GATTTCGGTG ATCATTGAAA GAAATGGTTT GAAACTTGCA     1380

ATACTGTCAT ACTCATCATA ATCCCCAATG TTGGAAATCA TGATGTCAAC AATTTTATTA     1440

AATTCTTCTG CTGCACTATT CAACTCCTTA ATCATGTCCT CAAAATGAGT GTTATAATCT     1500

CCATCCTTTT TAGTGATCTT ATCCCTCAAA ACTAAAGCTT TAGATTTGGA TTCGTCAAAA     1560

TTTTTCTTGA TATCATTAAC GGTATTGTCA TAATAGAATT TATAGATTAA ATGTTGTAAT     1620

AATAAGTCAC AATATATAAA CATATCTTTA AGTACAATAG ACTTCCATAT ATTACGGAAA     1680

TGGTCAAAAT TATCAGCAGC TGGACCTTCC AATGTACCAT AGGCCTTGTT TGATATTTCA     1740

TCAACCAATA ACTTATATTT TGAAGAGATA GTGGATGCAT TATCAAATAT TCTAGCCAAT     1800
```

-continued

```
TCTTCTTTCT TCATAAGGGA ATATTGTTCA GGAAAACATT TTTCCAATTC TTTTTTCAAT      1860

TTATTCTTCT CCTTGGTTTT TTCTTCAATG TAGTCTTTAT GACCATCGTT CACCCTATCT      1920

CGTTCCAATA TCATAACACT ATGTTTGTAT ATATAAGATA AACAAACTTC ATTAAATATA      1980

ACTATTCTTC TAGAATACGG AAGAAGCTGA TATCCAAATC GTTCACTAGA CCAACCAGCT      2040

TCACTAGGCC AACCAGTTCC ACTAGGCCAA CCAGTTCCAC TAGGCCCACC AGCTTCACTA      2100

GGCCCACCAG CTTCACTAGG CCCACCAGCT TCACTAGGCC CACCAGCTTC ACTAGGCCAA      2160

CCAGTTCCAC TAGGCCCACC AGCTTCACTA GGCCCACCAG CTTCACTGGG CCCAACAGTT      2220

CCACTAGGCC CACCAGCTTC ACTAGGCCCA CCAGCTTCGG GATCGGTATC ACTTGCAAAG      2280

ACAGCACCGC TCATTAAAAA GAGTGTAATA TAAGGAACTA ATATTGATTT AAATGACACC      2340

ATCTTTATAA ACCATAGTTA TTGGTACATT ATTAGTACAT TATTGGTATA TGATTGGTAC      2400

GTGGTAGTGA TTGTGGTGCT GCATCTAGTT                                      2430
```

(2) INFORMATION FOR SEQ ID NO:41:

(i) SEQUENCE CHARACTERISTICS:
    (A) LENGTH: 128 amino acids
    (B) TYPE: amino acid
    (C) STRANDEDNESS:
    (D) TOPOLOGY: linear (xi) SEQUENCE DESCRIPTION: SEQ ID NO:41:

```
Tyr Cys Val Asp Lys Asn Asp Val Ser Leu Trp Lys Ser Lys Pro Ile
1               5                   10                  15

Thr Thr Val Ser Thr Thr Asn Asp Thr Ile Thr Asn Thr His Thr Thr
            20                  25                  30

Asn Val Ile Asn Ala Asn Leu Ile Gly His Phe Asn Tyr Lys Asp Arg
        35                  40                  45

Glu Pro Leu Thr Ile Val Phe Val Tyr Met Ile Asp Glu Ser Glu Gln
    50                  55                  60

Asn Lys Leu Ser His Pro Asn Lys Ile Asp Lys Ile Lys Ile Ser Asp
65                  70                  75                  80

Tyr Ile Ile Glu Phe Asp Asp Asn Ala Lys Leu Pro Thr Gly Ser Val
                85                  90                  95

Ile Asp Leu Asn Ile Tyr Thr Cys Lys His Asn Asn Pro Val Leu Ile
            100                 105                 110

Glu Phe Tyr Val Ser Ile Glu Gly Ser Phe Cys Tyr Tyr Phe Ser His
        115                 120                 125
```

(2) INFORMATION FOR SEQ ID NO:42:

(i) SEQUENCE CHARACTERISTICS:
    (A) LENGTH: 1271 base pairs
    (B) TYPE: nucleic acid
    (C) STRANDEDNESS: single
    (D) TOPOLOGY: linear (xi) SEQUENCE DESCRIPTION: SEQ ID NO:42:

```
TGAGAAAACG CATATAATTG TAACTACGCC AGAGAAGTTT GACGTAGTTA CACGTAAAAC       60

AGGCAATGAG CCCCTGCTTG AGCGGCTTAG ATTGGTTATA ATTGATGAAA TACACCTACT      120

CCATGACACT AGGGGTCCAG TGCTGGAGGC TATTGTGGCC CGCCTGAGTC AGAGGCCCGA      180

ACGCGTAAGG CTAGTTGGTC TATCGGCCAC GCTTCCAAAC TACGAAGACG TGGCTAGATT      240

TCTCACTGTT AATCTAGACC GAGGGCTTTT CTACTTTGGC AGCCACTTTA GGCCTGTGCC      300

CTTGGAGCAG GTGTATTATG GCGTGAAGGA GAAGAAGGCT ATCAAACGTT CAACGCAAT      360
```

```
CAACGAAATT CTCTACCAAG AGGTGATTAA CGATGTTTCT AGCTGCCAAA TTCTTGTTTT      420

TGTGCATTCT AGAAAGGAAA CGTACAGGAC GGCAAAATTT ATCAAAGACA CGGCCCTTTC      480

ACGGGACAAC TTGGGAGCCT AAACCCTAAA CCCTAAACCC TAAACCCTAA CCCTAAACCC      540

TAAACCCTAA ACCCTAAACC CTAAACCCTA ACCCTAACCC TAACCCTAAC CCTAACCTAG      600

CCTTCATTGA CGTCTATCCC AATCTTAGA AAAATCTTCA AATCGATTCT AGAATAACTG       660

GAAGCAATTA TCAGAAATTG TATAACTGCT TATTAGCTTA TTAGCTTATT AGTTAGGATG      720

TATGCACATT GATGACAACT AGATGCAGCA CCACAATCAC TACCACGTAC CAATCATATA     780

CCAATAATGT ACTAATAATG TACCAATAAC TATGGTTTAT AAAGATGGTG TCATTTAAAT     840

CAATATTAGT TCCTTATATT ACACTCTTTT TAATGAGCGG TGCTGTCTTT GCAGGTGATA    900

CCGATCGCGA AGCTGGTGGG CCTAGTGGAA CTGTTGGGCC TAGTGAAGCT GGTGGGCCTA    960

GTGAAGCTGG TGGGCCTAGT GAAGCTGGTG GGCCTAGTGA AGCTGGTGGG CCTAGTGAAG   1020

CTGGTGGGCC TAGTGAAGCT GGTGGGCCTA GTGAAGCTGG TGGGCCTAGT GAAGCTGGTG   1080

GGCCTAGTGG AACTGGTTGG CCTAGTGAAG CTGGTGGGCC TAGTGAAGCT GGTGGGCCTA   1140

GTGAAGCTGG TGGGCCTAGT GGAACTGGTT GGCCTAGTGA AGCTGGTTGG CCTAGTGAAG   1200

CTGGTTGGCC TAGTGAAGCT GGTTGGCCTA GTGAAGCTGG TTGGCCTAGT GAAGCTGGTT   1260

GGCCTAGTGA A                                                       1271
```

(2) INFORMATION FOR SEQ ID NO:43:

(i) SEQUENCE CHARACTERISTICS:
        (A) LENGTH: 166 amino acids
        (B) TYPE: amino acid
        (C) STRANDEDNESS:
        (D) TOPOLOGY: linear (xi) SEQUENCE DESCRIPTION: SEQ ID NO:43:

```
Glu Lys Thr His Ile Ile Val Thr Thr Pro Glu Lys Phe Asp Val Val
1               5                   10                  15

Thr Arg Lys Thr Gly Asn Glu Pro Leu Leu Glu Arg Leu Arg Leu Val
            20                  25                  30

Ile Ile Asp Glu Ile His Leu Leu His Asp Thr Arg Gly Pro Val Leu
        35                  40                  45

Glu Ala Ile Val Ala Arg Leu Ser Gln Arg Pro Glu Arg Val Arg Leu
    50                  55                  60

Val Gly Leu Ser Ala Thr Leu Pro Asn Tyr Glu Asp Val Ala Arg Phe
65                  70                  75                  80

Leu Thr Val Asn Leu Asp Arg Gly Leu Phe Tyr Phe Gly Ser His Phe
                85                  90                  95

Arg Pro Val Pro Leu Glu Gln Val Tyr Tyr Gly Val Lys Glu Lys Lys
            100                 105                 110

Ala Ile Lys Arg Phe Asn Ala Ile Asn Glu Ile Leu Tyr Gln Glu Val
        115                 120                 125

Ile Asn Asp Val Ser Ser Cys Gln Ile Leu Val Phe Val His Ser Arg
    130                 135                 140

Lys Glu Thr Tyr Arg Thr Ala Lys Phe Ile Lys Asp Thr Ala Leu Ser
145                 150                 155                 160

Arg Asp Asn Leu Gly Ala
                165
```

(2) INFORMATION FOR SEQ ID NO:44:

(i) SEQUENCE CHARACTERISTICS:
    (A) LENGTH: 154 amino acids
    (B) TYPE: amino acid
    (C) STRANDEDNESS:
    (D) TOPOLOGY: linear (xi) SEQUENCE DESCRIPTION: SEQ ID NO:44:

```
Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
    50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Glu Ala Gly Gly Pro Ser Gly Thr Gly
            85                  90                  95

Trp Pro Ser Glu Ala Gly Gly Pro Ser Glu Ala Gly Gly Pro Ser Glu
        100                 105                 110

Ala Gly Gly Pro Ser Gly Thr Gly Trp Pro Ser Glu Ala Gly Trp Pro
    115                 120                 125

Ser Glu Ala Gly Trp Pro Ser Glu Ala Gly Trp Pro Ser Glu Ala Gly
    130                 135                 140

Trp Pro Ser Glu Ala Gly Trp Pro Ser Glu
145                 150
```

(2) INFORMATION FOR SEQ ID NO:45:

(i) SEQUENCE CHARACTERISTICS:
        (A) LENGTH: 4223 base pairs
        (B) TYPE: nucleic acid
        (C) STRANDEDNESS: single
        (D) TOPOLOGY: linear (xi) SEQUENCE DESCRIPTION: SEQ ID NO:45:

```
CTCGTGCCTT TCTCAACTGA TAACAGCTAA CAAAAAGTCT CTTATCTTAA ACCATCCTAT     60

ACCTCGTATT ATAATATGAA AAGGGCCTTT TCTAAATCTT TCCCCAAAGT TCTGCTATTT    120

AATTAAAAAA AAAAAAGACT CATTCAATAA ACGGGTGGGG CAGAAAGGGT ACCTTTCCAA    180

GTGTTCTTCC ATGACGACCC ACAATGCAAA GTTCTTCTTA CAAAGAAAAG AGAAAGATCC    240

ACTGAGTGAT AAGTAACCCA GCTGGGGCCG GGCGGTGGTG GCGCACACCT TTAATCCCAG    300

CACTCGGGAG GCAGAGGCAG GCGGATCTCT GTGAGTTCGA GACCAGGCTG GACCGACAGC    360

CTCCAAAACA ATACAGAGAA ACCCTGTCTC ATAAAAAACC AAAAAAAAAG TAACCCAGCT    420

GGATTTGGTA ACTGTCTCAG AAACAGACTA TATAAAACCT CATCACCCTA CAACAAGTAG    480

GAAGCTAGCG CTCCCCACCC CATCCCAACA CACACACACA CACACACACA CACACACACA    540

CACACACACA CACGCACACA CGCACGCACG CACACACGCA CGCACGCACA CACGCACACA    600

CGCACGCACA CACGCACACA CGCACGCACG CACGCACGCA CGCACGCACG CACGCCCTTC    660

TGTGTCTGTT CTGTTCAAGA AGGGTACCAC AAAAAAGTAC CTTATGGCCA CATCAATGAC    720

AATTATTACT GTATATAAAA TGCCCCCATG GATGGCATTG TATTGTCGAA ATTAAAGGCA    780

CCCCCGAAAG AACAGCACAG AGGGGCTACC ACCAATTAAC TCCCAGGAGG AAATAAAGAC    840

AGAAGTGTGA AGGAGGGAGA GAGGGAGGGA GGAAGGGAGG GAGAAAAGGA GGGAAAGGAA    900
```

```
CAAGGAGTAA CAGGGACAAA AGCAGCAGAT GGTGCCAGGC AGGAGTGTGC CTACCACACC       960

GGGCCTTCCC GTTACTTCAT TTACTCTCCT TTGCAGCCTG GGAATAAACA AGTCACGCGT      1020

CACCCGGTGT CTCAAGCTCA GCATGGCTTG ATCTGAGTGC CCGTGTATGT GTTCATTCTA      1080

TAACTGATTT AAGGAACAAC TTTCTGCTCA TTGCCTCTAT CTTCTCAAAC ATTTCGAAGC      1140

AGTTATTTTT TATAAGAAAA TATAAACAG GCCGACTAAA TTCGATCTTT CTCTCCCCAG       1200

CTGCTAGTTT CTTATCTAGC TGCTTTAGGC AGTCTCCACA GATTGCAGCC AGGCCCCTAT      1260

TCTCAATTCC ATCTGACTTC TGACAGCGCT CTCCATTTCT TATTTGCAGC TTAGACATCT      1320

TCACTGAGAG CAGGAGTAAT TCATTCAAAT GACAATGAGG TATCTGAATA TCACACAAAC      1380

ACTTCAAATT CTGTTTATTG GAAATAGATC TGCTCCTGCC CCATCATAAC AATCCTTTTT      1440

ATCTTACTTA ACAGGGCAA GAAAATCTTT CACTTCATTT CCTATCATCT CAAATGAGTT       1500

CCTGTACATG AATGACTTAA GGTAACCATA TCCAACAACT GAAGCCAAC CAGTCCCTGG       1560

TCCTACTACA GACGTTAGGG AACATATGTG AAAACCTGGT GTACAACCTA ATCATAACT       1620

AGACAGAAGA CAGCACTATT TCCTGGTCAC ATAGAAAGCA GAATAGCATC CTCACACCAA      1680

TGAGGAAAAT GTCATGAAGG CAGGAGAGAT CATGACTGAG GTGATACTTT TACCAAAGAC      1740

TTGCCAGTGA TTAATTTCTC AATTAGTTAG CAAAAAATAT GGCTCTCTAG TGAATTTGTG      1800

TCCACACCAT TTTCCAGATG TTTTGATGTC ACTTAAATCA ATCTAATTAT TTAAGTTAAA     1860

AAATGTTACA GATCATTGCT TTTTTTCTTT TTTAGAAGAC ATCAAACAA TAGGATTTCT       1920

ATGAAATATT CTCACTTCAC AGCTGTGTCA GTTAAAGTGC TTTGGGTTAT ACATAAAGAA      1980

AACAGACTCA AGAAAGTAAG AACAGGAATT TGGAGCTTGC AACACTGATG TTCTTTGTAA      2040

AAAGAGAGAC TTTATCCAGG GATTAGATTC TGTCACAAGG CCTGGAACTC TCTCTTCTCA     2100

GCCTTATTTC CCCAATATGG ATTAGAATCT TACACTGCAA GCTTCCCACA AGGGTGGACA     2160

GGTCCTCACC ATTTGTTTCA GCAGGAAAAA GAGTCTGTAT GCATCCGTGA TATCTAAGTC     2220

ACAATTCCAG AAGTGAGCTT TCCTGGCTCC TATTGGTCGG ACTTAGGTCA GGTGTCACAT     2280

TTCCTTTTGG ATTAGTCTGT GATTAATGAA TGGGCCCACT TTGCTCACCC ATTAAGACAA     2340

TAGGCTTCCA TTCTCGAAGC TGGAAGCATG ACATGTCCCA CAGAAACTGT AATAAGAGAG     2400

AACATAGGTT GCTGTGTGGA GAAACGAGGC AACCGGCAAG TCATAAGATG ACAAAGTCTT     2460

GGAAAGTCTA AGTCAGTGGT TCTCAGCCTT CCCTAAACCC TAAACCCTAA ACCCTAAACC     2520

CTAAACCCTA AACCCTAAAC CCCTAAACCC TAAACCCTAA ACCCTAAACC CTAAACCCTA     2580

ACCCTAAACC CTAAACCCTA AACCCTAAAC CCTAAACCCT AACCCTAACC CTAACCCTAA     2640

CCCTAACCTA GCCTTCATTG ACGTCTATCC CCAATCTTAG AAAAATCTTC AAATCGATTC     2700

TAGAATAACT GGAAGCAATT ATCAGAAATT GTATAACTGC TTATTAGCTT ATTAGCTTAT     2760

TAGTTAGGAT GTATGCACAT TGATGACAAC TAGATGCAGC ACCACAATCA CTACCACGTA     2820

CCAATCATAT ACCAATAATG TACTAATAAT GTACCAATAA CTATGGTTTA TAAAGATGGT     2880

GTCATTTAAA TCAATATTAG TTCCTTATAT TACACTCTTT TTAATGAGCG GTGCTGTCTT     2940

TGCAGGTGAT ACCGATCGCG AAGCTGGTGG GCCTAGTGGA ACTGTTGGGC CTAGTGAAGC     3000

TGGTGGGCCT AGTGAAGCTG GTGGGCCTAG TGAAGCTGGT GGGCCAGTG AAGCTGGTGG      3060

GCCTAGTGAA GCTGGTGGGC CTAGTGAAGC TGGTGGGCCT AGTGAAGCTG TGGGCCTAG      3120

TGGAACTGTT GGGCCTAGTG AAGCTGGTGG GCCTAGTGAA GCTGGTGGGC CTAGTGAAGC     3180

TGGTGGGCCT AGTGAAGCTG GTTGGCCTAG TGAAGCTGGT TGGCCTAGTG AAGCTGGTTG     3240
```

-continued

```
GCCTAGTGAA GCTGGTTGGC CTAGTGAAGC TGGTTGGCCT AGTGAAGCTG GTTGGCCTAG    3300

TGAACGATTT GGATATCAGC TTCTTTGGTA TTCTAGAAGA ATAGTTATAT TTAATGAAAT    3360

TTATTTATCT CATATATACG AACATAGTGT TATGATATTG GAACGAGATA GGGTGAACGA    3420

TGGTCATAAA GACTACATTG AAGAAAAAAC CAAGGAGAAG AATAAATTGA AAAAGAATT     3480

GGAAAAATGT TTTCCTGAAC AATATTCCCT TATGAAGAAA GAAGAATTGG CTAGAATAAT    3540

TGATAATGCA TCCACTATCT CTTCAAAATA TAAGTTATTG GTTGATGAAA TATCCAACAA    3600

AGCCTATGGT ACATTGGAAG GTCCAGCTGC TGATGATTTT GACCATTTCC GTAATATATG    3660

GAAGTCTATT GTACCTAAAA ATATGTTTCT ATATTGTGAC TTATTATTAA AACATTTAAT    3720

CCGTTTAACC CCCAGAAAGA GCTGACCAGA CAAAGGTTAA CTCTTGAATC CCAGGCATCA    3780

GCCTGGGAAT CCATCATGGG ACTGATCAAG ACCCCCTGAA TGTGGGTGTC AGTGAGGAGG    3840

CCTAGGTAAT CTATTGAGCC TCGGGCAGCA GATCAGTACC CATCCCAATT ATACACAATT    3900

GCAGTGTTGT GGTTTCACAG TGAATAATTG TAGGTCACAG TCCATTATAT TGATGTCACA    3960

GTTTTTAATT GTCATGTCAC AGTGCAAGCT AGTGATGTCA GAGTGTATAA CTGTGTTCAT    4020

AGAGAATGTA TTGATGTCAC AGTCAATAAT CGTGATGTCA TAGTGCAGTA TATTGATGTC    4080

ACAATGTATA ATTGTGATGT TAAAGTGCAA GATAGTGAAG TCACAGTATA TAATTGTGAT    4140

GTCATATTGC ATTATAATGA TGTCACACTT TATAATTTTT TACATACAGC ACTATAGTGA    4200

TGTAACAGCC AATAATTGTG ATG                                           4223
```

(2) INFORMATION FOR SEQ ID NO:46:

(i) SEQUENCE CHARACTERISTICS:
        (A) LENGTH: 294 amino acids
        (B) TYPE: amino acid
        (C) STRANDEDNESS:
        (D) TOPOLOGY: linear (xi) SEQUENCE DESCRIPTION: SEQ ID NO:46:

```
Leu Trp Phe Ile Lys Met Val Ser Phe Lys Ser Ile Leu Val Pro Tyr
1               5                   10                  15

Ile Thr Leu Phe Leu Met Ser Gly Ala Val Phe Ala Gly Asp Thr Asp
            20                  25                  30

Arg Glu Ala Gly Gly Pro Ser Gly Thr Val Gly Pro Ser Glu Ala Gly
        35                  40                  45

Gly Pro Ser Glu Ala Gly Gly Pro Ser Glu Ala Gly Gly Pro Ser Glu
    50                  55                  60

Ala Gly Gly Pro Ser Glu Ala Gly Gly Pro Ser Glu Ala Gly Gly Pro
65                  70                  75                  80

Ser Glu Ala Gly Gly Pro Ser Gly Thr Val Gly Pro Ser Glu Ala Gly
                85                  90                  95

Gly Pro Ser Glu Ala Gly Gly Pro Ser Glu Ala Gly Gly Pro Ser Glu
                100                 105                 110

Ala Gly Trp Pro Ser Glu Ala Gly Trp Pro Ser Glu Ala Gly Trp Pro
            115                 120                 125

Ser Glu Ala Gly Trp Pro Ser Glu Ala Gly Trp Pro Ser Glu Ala Gly
        130                 135                 140

Trp Pro Ser Glu Arg Phe Gly Tyr Gln Leu Leu Trp Tyr Ser Arg Arg
145                 150                 155                 160

Ile Val Ile Phe Asn Glu Ile Tyr Leu Ser His Ile Tyr Glu His Ser
                165                 170                 175

Val Met Ile Leu Glu Arg Asp Arg Val Asn Asp Gly His Lys Asp Tyr
```

```
                  180                 185                 190
Ile Glu Glu Lys Thr Lys Glu Lys Asn Lys Leu Lys Lys Glu Leu Glu
            195                 200                 205

Lys Cys Phe Pro Glu Gln Tyr Ser Leu Met Lys Lys Glu Glu Leu Ala
        210                 215                 220

Arg Ile Ile Asp Asn Ala Ser Thr Ile Ser Ser Lys Tyr Lys Leu Leu
225                 230                 235                 240

Val Asp Glu Ile Ser Asn Lys Ala Tyr Gly Thr Leu Glu Gly Pro Ala
                245                 250                 255

Ala Asp Asp Phe Asp His Phe Arg Asn Ile Trp Lys Ser Ile Val Pro
            260                 265                 270

Lys Asn Asn Phe Leu Tyr Cys Asp Leu Leu Leu Lys His Leu Ile Arg
        275                 280                 285

Leu Thr Pro Arg Lys Ser
    290

(2) INFORMATION FOR SEQ ID NO:47:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:47:

Ser Glu Ala Gly Gly Pro Ser Glu Ala Gly Gly Pro Ser Gly Thr Gly
1               5                  10                  15

Trp Thr Ser Gly Thr Gly Trp Pro Ser Glu Ala Gly Trp Ser
            20                  25                  30

(2) INFORMATION FOR SEQ ID NO:48:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:48:

Glu Ala Gly Gly Pro Ser Gly Thr Val Gly Pro Ser Gly Thr Gly Trp
1               5                  10                  15

Pro Ser Glu Ala Gly Trp Gly Ser Glu Ala Gly Trp Ser Ser
            20                  25                  30

(2) INFORMATION FOR SEQ ID NO:49:

(i) SEQUENCE CHARACTERISTICS:
        (A) LENGTH: 367 amino acids
        (B) TYPE: amino acid
        (C) STRANDEDNESS: single
        (D) TOPOLOGY: linear (xi) SEQUENCE DESCRIPTION: SEQ ID NO:49:

Met Val Ser Phe Lys Ser Ile Leu Val Pro Tyr Ile Thr Leu Phe Leu
1               5                  10                  15

Met Ser Gly Ala Val Phe Ala Ser Asp Thr Asp Pro Glu Ala Gly Gly
            20                  25                  30

Pro Ser Glu Ala Gly Gly Pro Ser Gly Thr Val Gly Pro Ser Glu Ala
        35                  40                  45

Gly Gly Pro Ser Glu Ala Gly Gly Pro Ser Gly Thr Gly Trp Pro Ser
    50                  55                  60
```

```
Glu Ala Gly Gly Pro Ser Glu Ala Gly Gly Pro Ser Glu Ala Gly Gly
 65                  70                  75                  80

Pro Ser Glu Ala Gly Gly Pro Ser Gly Thr Gly Ser Glu Ala Gly Gly
                 85                  90                  95

Trp Pro Ser Gly Thr Gly Trp Pro Ser Glu Ala Gly Trp Ser Ser Glu
            100                 105                 110

Arg Phe Gly Tyr Gln Leu Leu Pro Tyr Ser Arg Ile Val Ile Phe
            115                 120                 125

Asn Glu Val Cys Leu Ser Tyr Ile Tyr Lys His Ser Val Met Ile Leu
        130                 135                 140

Glu Arg Asp Arg Val Asn Asp Gly His Lys Asp Tyr Ile Glu Lys
145                 150                 155                 160

Thr Lys Glu Lys Asn Lys Leu Lys Lys Glu Leu Glu Lys Cys Phe Pro
                165                 170                 175

Glu Gln Tyr Ser Leu Met Lys Lys Glu Glu Leu Ala Arg Ile Phe Asp
            180                 185                 190

Asn Ala Ser Thr Ile Ser Ser Lys Tyr Lys Leu Leu Val Asp Glu Ile
            195                 200                 205

Ser Asn Lys Ala Tyr Gly Thr Leu Glu Gly Pro Ala Ala Asp Asn Phe
210                 215                 220

Asp His Phe Arg Asn Ile Trp Lys Ser Ile Val Leu Lys Asp Met Phe
225                 230                 235                 240

Ile Tyr Cys Asp Leu Leu Leu Gln His Leu Ile Tyr Lys Phe Tyr Tyr
                245                 250                 255

Asp Asn Thr Val Asn Asp Ile Lys Lys Asn Phe Asp Glu Ser Lys Ser
                260                 265                 270

Lys Ala Leu Val Leu Arg Asp Lys Ile Thr Lys Lys Asp Gly Asp Tyr
275                 280                 285

Asn Thr His Phe Glu Asp Met Ile Lys Glu Leu Asn Ser Ala Ala Glu
            290                 295                 300

Glu Phe Asn Lys Ile Val Asp Ile Met Ile Ser Asn Ile Gly Asp Tyr
305                 310                 315                 320

Asp Glu Tyr Asp Ser Ile Ala Ser Phe Lys Pro Phe Leu Ser Met Ile
                325                 330                 335

Thr Glu Ile Thr Lys Ile Thr Lys Val Ser Asn Val Ile Ile Pro Gly
            340                 345                 350

Ile Lys Ala Leu Thr Leu Thr Val Phe Leu Ile Phe Ile Thr Lys
            355                 360                 365

(2) INFORMATION FOR SEQ ID NO:50:

(i) SEQUENCE CHARACTERISTICS:
        (A) LENGTH: 1908 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
         (A) ORGANISM: Babesia Microti (xi) SEQUENCE DESCRIPTION: SEQ ID NO:50:

AAAAGATTTA ATGAACATAC TGACATGAAT GGTATTCATT ATTATTATAT TGATGGTAGT      60

TTACTTGCGA GTGGCGAAGT TACATCTAAT TTTCGTTATA TTTCTAAAGA ATATGAATAT    120

GAGCATACAG AATTAGCAAA AGAGCATTGC AAGAAAGAAA AATGTGTAAA TGTGGATAAC    180
```

```
ATTGAGGATA ATAATTTGAA AATATATGCG AAACAGTTTA AATCTGTAGT TACTACTCCA      240

GCTGATGTAG CGGGTGTGTC AGATGGATTT TTTATACGTG GCCAAAATCT TGGTGCTGTG      300

GGCAGTGTAA ATGAACAACC TAATACTGTT GGTATGAGTT TAGAACAATT CATCAAGAAC      360

GAGCTTTATT CTTTTAGTAA TGAAATTTAT CATACAATAT CTAGTCAAAT CAGTAATTCT      420

TTCTTAATAA TGATGTCTGA TGCAATTGTT AAACATGATA ACTATATTTT AAAAAAAGAA      480

GGTGAAGGCT GTGAACAAAT CTACAATTAT GAGGAATTTA TAGAAAAGTT GAGGGGTGCT      540

AGAAGTGAGG GGAATAATAT GTTTCAGGAA GCTCTGATAA GGTTTAGGAA TGCTAGTAGT      600

GAAGAAATGG TTAATGCTGC AAGTTATCTA TCCGCCGCCC TTTTCAGATA TAAGGAATTT      660

GATGATGAAT TATTCAAAAA GGCCAACGAT AATTTTGGAC GCGATGATGG ATATGATTTT      720

GATTATATAA ATACAAAGAA AGAGTTAGTT ATACTTGCCA GTGTGTTGGA TGGTTTGGAT      780

TTAATAATGG AACGTTTGAT CGAAAATTTC AGTGATGTCA ATAATACAGA TGATATTAAG      840

AAGGCATTTG ACGAATGCAA ATCTAATGCT ATTATATTGA AGAAAAAGAT ACTTGACAAT      900

GATGAAGATT ATAAGATTAA TTTTAGGGAA ATGGTGAATG AAGTAACATG TGCAAACACA      960

AAATTTGAAG CCCTAAATGA TTTGATAATT TCCGACTGTG AGAAAAAAGG TATTAAGATA     1020

AACAGAGATG TGATTTCAAG CTACAAATTG CTTCTTTCCA CAATCACCTA TATTGTTGGA     1080

GCTGGAGTTG AAGCTGTAAC TGTTAGTGTG TCTGCTACAT CTAATGGAAC TGAATCTGGT     1140

GGAGCTGGTA GTGGAACTGG AACTAGTGTG TCTGCTACAT CTACTTTAAC TGGTAATGGT     1200

GGAACTGAAT CTGGTGGAAC AGCTGGAACT ACTACGTCTA GTGGAACTGA AGCTGGTGGA     1260

ACTAGTGGAA CTACTACGTC TAGTGGAGCT GCTAGTGGTA AAGCTGGAAC TGGAACAGCT     1320

GGAACTACTA CGTCTAGTGA AGGTGCTGGT AGTGATAAAG CTGGAACTGG AACTAGTGGA     1380

ACTACTACGT CTAGTGGAAC TGGTGCTGGT GGAGCTGGTA GTGGTGGACC TAGTGGACAT     1440

GCTTCTAATG CAAAAATTCC TGGAATAATG ACACTAACTC TATTTGCATT ATTAACATTT     1500

ATTGTAAATT GAATGAAACA CATGATTTAT ACATTATTAT ATATTACAAA ATTTACACAT     1560

TATTTATGTA TGAACGAACG AACATCTTGC TCTTAAATAA AGAAATTGAG ATATATATGG     1620

AAATAGATTA AAGTAACATG AGAAAGATGA ATATAATATT AGAATATGAA ATTTAACAGA     1680

AATAAAATGA AGTAAAAGAG TGTATTTTGT AATAATTTAT AATAAATTAG TATACAATGA     1740

TTATATTACA AATGGCTATT AAATATTTTA TTAATTAAAT ATTGATTAGT AATGATATTA     1800

TGTATGTACA TGTTAGGGTT GATTGTTATA CATTGTGAAT ATATTATATA ATTGTATATT     1860

ATATTGATTG ATATAATGTA GAGGATATTT TTTTAAATAG TATTTAAT                 1908

(2) INFORMATION FOR SEQ ID NO:51:

(i) SEQUENCE CHARACTERISTICS:
        (A) LENGTH: 1460 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:51:

AATCCAACAT CTAGCCTAGT TAGTATATAT AGGTTAAATA CACATTATAG ATTATCTTTG       60

GATGATTGGT TATTATATAA CATGTCGCTG AATGACGATT ATTTTGCTAG ATAATATAAC      120
```

-continued

```
TACCGGTGAT TCTGAGGACC TACTTTAAAG AGAATAATTA ACATATCTAC CAGAATCAGT      180

TCCAATTTAT GTATTTTAAA GCTAATCACT ACTCGAAAAC TACGGTGAAA ATGGAAAAAC      240

AAGTGGAAGC TGTATGTCGT GGAAAGTCAC TACATTTTAT GTGGGCAAAT TTAATAATTC      300

TAAATACTAT GTTTTTGATG TTAAAAAGCG AAAAACACAC TTTAATGCAC ATTTTAACAT      360

CATCTGTATA ATATATATAT CAGCGTTGAA ATCATATGGC AAAGGTAATA AAGCGTTACA      420

TTTTGAGCGA ATAAAGGCAC ATATGCAAAC GTATGAAGCC TTGTATATTT GTGGAATTAT      480

ATTATGCTAG TAATTTGTGA TTAATAATGG CAATATTTAT ATACAAATAT TCGAGCGTTC      540

TATTATATGC ATGCACATAA TTAATCACAA ACTCTCATAT CATGGGCGG TTTCGCCCAT       600

CATAAACATT ACTGTTAGCA CTCTGGTAGA TTAGCATGGT GAATCTCTCG ATACCTGGGC      660

TACTGTTGCT TTCCGCATAT TCCTTAAATT CTGCAAGTGC GGGGGATGTA TATGAGATAT      720

CTTCTGGTAA TCCACCCGAC ATAGAGCCAA CATCTACTTC TCTAGAAACA AATGTAGTTA      780

CCAACTATAT TCCAGAACCC AATGCGGATT CAGAATCTGT ACATGTTGAA ATCCAGGAAC      840

ATGATAACAT CAATCCACAA GACGCTTGCG ATAGTGAGCC GCTCGAACAA ATGGATTCTG      900

ATACCAGGGT GTTGCCCGAA AGTTTGGATG AGGGGGTACC ACACCAATTC TCTAGATTAG      960

GGCACCACTC AGACATGGCA TCTGATATAA ATGATGAAGA ACCATCATTT AAAATCGGCG     1020

AGAATGACAT AATTCAACCA CCCTGGGAAG ATACAGCTCC ATACCATTCA ATAGATGATG     1080

AAGAGCTTGA CAACTTAATG AGACTAACGG CGCAAGAAAC AAGTGACGAT CATGAAGAAG     1140

GGAATGGCAA ACTCAATACG AATAAAAGTG AGAAGACTGA AGAAAATCG CATGATACTC      1200

AGACACCGCA AGAAATATAT GAAGAGCTTG ACAACTTACT GAGACTAACG GCACAAGAAA     1260

TATATGAAGA GCGTAAAGAA GGGCATGGCA AACCCAATAC GAATAAAAGT GAGAAGGCTG     1320

AAAGAAAATC GCATGATACT CAGACAACGC AAGAAATATG TGAAGAGTGT GAAGAAGGGC     1380

ATGACAAAAT CAATAAGAAT AAAAGTGGAA ATGCTGGAAT AAAATCGTAT GATACTCAGA     1440

CACCGCAGGA AACAAGTGAC                                                 1460
```

(2) INFORMATION FOR SEQ ID NO:52:

(i) SEQUENCE CHARACTERISTICS:
        (A) LENGTH: 503 amino acids
        (B) TYPE: amino acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:52:

```
Lys Arg Phe Asn Glu His Thr Asp Met Asn Gly Ile His Tyr Tyr Tyr
1               5                   10                  15

Ile Asp Gly Ser Leu Leu Ala Ser Gly Glu Val Thr Ser Asn Phe Arg
            20                  25                  30

Tyr Ile Ser Lys Glu Tyr Glu Tyr Glu His Thr Glu Leu Ala Lys Glu
        35                  40                  45

His Cys Lys Lys Glu Lys Cys Val Asn Val Asp Asn Ile Glu Asp Asn
    50                  55                  60

Asn Leu Lys Ile Tyr Ala Lys Gln Phe Lys Ser Val Val Thr Thr Pro
65                  70                  75                  80

Ala Asp Val Ala Gly Val Ser Asp Gly Phe Phe Ile Arg Gly Gln Asn
                85                  90                  95
```

-continued

```
Leu Gly Ala Val Gly Ser Val Asn Glu Gln Pro Asn Thr Val Gly Met
            100                 105                 110
Ser Leu Glu Gln Phe Ile Lys Asn Glu Leu Tyr Ser Phe Ser Asn Glu
            115                 120                 125
Ile Tyr His Thr Ile Ser Ser Gln Ile Ser Asn Ser Phe Leu Ile Met
            130                 135                 140
Met Ser Asp Ala Ile Val Lys His Asp Asn Tyr Ile Leu Lys Lys Glu
145                 150                 155                 160
Gly Glu Gly Cys Glu Gln Ile Tyr Asn Tyr Glu Glu Phe Ile Glu Lys
                165                 170                 175
Leu Arg Gly Ala Arg Ser Glu Gly Asn Asn Met Phe Gln Glu Ala Leu
            180                 185                 190
Ile Arg Phe Arg Asn Ala Ser Ser Glu Glu Met Val Asn Ala Ala Ser
            195                 200                 205
Tyr Leu Ser Ala Ala Leu Phe Arg Tyr Lys Glu Phe Asp Asp Glu Leu
            210                 215                 220
Phe Lys Lys Ala Asn Asp Asn Phe Gly Arg Asp Asp Gly Tyr Asp Phe
225                 230                 235                 240
Asp Tyr Ile Asn Thr Lys Lys Glu Leu Val Ile Leu Ala Ser Val Leu
                245                 250                 255
Asp Gly Leu Asp Leu Ile Met Glu Arg Leu Ile Glu Asn Phe Ser Asp
            260                 265                 270
Val Asn Asn Thr Asp Asp Ile Lys Lys Ala Phe Asp Glu Cys Lys Ser
            275                 280                 285
Asn Ala Ile Ile Leu Lys Lys Lys Ile Leu Asp Asn Asp Glu Asp Tyr
            290                 295                 300
Lys Ile Asn Phe Arg Glu Met Val Asn Glu Val Thr Cys Ala Asn Thr
305                 310                 315                 320
Lys Phe Glu Ala Leu Asn Asp Leu Ile Ile Ser Asp Cys Glu Lys Lys
                325                 330                 335
Gly Ile Lys Ile Asn Arg Asp Val Ile Ser Ser Tyr Lys Leu Leu Leu
            340                 345                 350
Ser Thr Ile Thr Tyr Ile Val Gly Ala Gly Val Glu Ala Val Thr Val
            355                 360                 365
Ser Val Ser Ala Thr Ser Asn Gly Thr Glu Ser Gly Gly Ala Gly Ser
370                 375                 380
Gly Thr Gly Thr Ser Val Ser Ala Thr Ser Thr Leu Thr Gly Asn Gly
385                 390                 395                 400
Gly Thr Glu Ser Gly Gly Thr Ala Gly Thr Thr Thr Ser Ser Gly Thr
                405                 410                 415
Glu Ala Gly Gly Thr Ser Gly Thr Thr Thr Ser Ser Gly Ala Ala Ser
            420                 425                 430
Gly Lys Ala Gly Thr Gly Thr Ala Gly Thr Thr Thr Ser Ser Glu Gly
            435                 440                 445
Ala Gly Ser Asp Lys Ala Gly Thr Gly Thr Ser Gly Thr Thr Thr Ser
            450                 455                 460
Ser Gly Thr Gly Ala Gly Gly Ala Gly Ser Gly Gly Pro Ser Gly His
465                 470                 475                 480
Ala Ser Asn Ala Lys Ile Pro Gly Ile Met Thr Leu Thr Leu Phe Ala
                485                 490                 495
Leu Leu Thr Phe Ile Val Asn
            500
```

(2) INFORMATION FOR SEQ ID NO:53:

(i) SEQUENCE CHARACTERISTICS:
        (A) LENGTH: 275 amino acids
        (B) TYPE: amino acid
        (C) STRANDEDNESS: single
        (D) TOPOLOGY: linear (ii) MOLECULE TYPE: DNA (genomic)

(vi) ORIGINAL SOURCE:
        (A) ORGANISM: Babesia Microti (xi) SEQUENCE DESCRIPTION: SEQ ID NO:53:

```
Met Val Asn Leu Ser Ile Pro Gly Leu Leu Leu Ser Ala Tyr Ser
 1               5                  10                  15

Leu Asn Ser Ala Ser Ala Gly Asp Val Tyr Glu Ile Ser Ser Gly Asn
                20                  25                  30

Pro Pro Asp Ile Glu Pro Thr Ser Thr Ser Leu Glu Thr Asn Val Val
            35                  40                  45

Thr Asn Tyr Ile Pro Glu Pro Asn Ala Asp Ser Glu Ser Val His Val
        50                  55                  60

Glu Ile Gln Glu His Asp Asn Ile Asn Pro Gln Asp Ala Cys Asp Ser
65                  70                  75                  80

Glu Pro Leu Glu Gln Met Asp Ser Asp Thr Arg Val Leu Pro Glu Ser
                85                  90                  95

Leu Asp Glu Gly Val Pro His Gln Phe Ser Arg Leu Gly His His Ser
            100                 105                 110

Asp Met Ala Ser Asp Ile Asn Asp Glu Glu Pro Ser Phe Lys Ile Gly
        115                 120                 125

Glu Asn Asp Ile Ile Gln Pro Arg Trp Glu Asp Thr Ala Pro Tyr His
130                 135                 140

Ser Ile Asp Asp Glu Glu Leu Asp Asn Leu Met Arg Leu Thr Ala Gln
145                 150                 155                 160

Glu Thr Ser Asp Asp His Glu Glu Gly Asn Gly Lys Leu Asn Thr Asn
                165                 170                 175

Lys Ser Glu Lys Thr Glu Arg Lys Ser His Asp Thr Gln Thr Pro Gln
            180                 185                 190

Glu Ile Tyr Glu Glu Leu Asp Asn Leu Leu Arg Leu Thr Ala Gln Glu
        195                 200                 205

Ile Tyr Glu Glu Arg Lys Glu Gly His Gly Lys Pro Asn Thr Asn Lys
        210                 215                 220

Ser Glu Lys Ala Glu Arg Lys Ser His Asp Thr Gln Thr Thr Gln Glu
225                 230                 235                 240

Ile Cys Glu Glu Cys Glu Glu Gly His Asp Lys Ile Asn Lys Asn Lys
                245                 250                 255

Ser Gly Asn Ala Gly Ile Lys Ser Tyr Asp Thr Gln Thr Pro Gln Glu
            260                 265                 270

Thr Ser Asp
        275
```

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:54:

| | |
|---|---|
| TTTGCAGGTG ATACCGATCG CG | 22 |

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:55:

| | |
|---|---|
| TGGTATTCTA GAAGAATAGT TATA | 24 |

(2) INFORMATION FOR SEQ ID NO:56:

(i) SEQUENCE CHARACTERISTICS:
        (A) LENGTH: 306 base pairs
        (B) TYPE: nucleic acid
        (C) STRANDEDNESS: single
        (D) TOPOLOGY: linear (xi) SEQUENCE DESCRIPTION: SEQ ID NO:56:

| | |
|---|---|
| TTGCAGGTGA TACCGATCGC GAAGCTGGTG GGCCTAGTGG AACTGTTGGG CCCAGTGAAG | 60 |
| CTGGTGGGCC TAGTGAAGCT GGTGGGCCTA GTGGAACTGT TGGGCCCAGT GAAGCTGGTG | 120 |
| GGCCTAGTGA AGCTGGTGGG CCTAGTGGAA CTGGTTGGCC TAGTGAAGCT GGTGGGCCTA | 180 |
| GTGGAACTGT TGGGCCCAGT GAAGCTGGTG GCCTAGTGA AGCTGGTGGG CCTAGTGGAA | 240 |
| CTGGTTGGCC TAGTGGAACT GGTTGGCCTA GTGAAGTTGG TTGGCCCATT GAACCATTTG | 300 |
| GATATC | 306 |

(2) INFORMATION FOR SEQ ID NO:57:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO:57:

| | |
|---|---|
| TTGCAGGTGA TACCGATCGC GAAGCTGGTG GGCCTAGTGG AACTGTTGGG CCCAGTGAAG | 60 |
| CTGGTGGGCC TAGTGAAGCT GGTGGGCCTA GTGGAACTGT TGGGCCCAGT GAAGCTGGTG | 120 |
| GGCCTAGTGA AGCTGGTGGG CCTAGTGGAA CTGGTTGGCC TAGTGAAGCT GGTGGGCCTA | 180 |
| GTGGAACTGT TGGGCCCAGT GAAGCTGGTG GGCCTAGTGA AGCTGGTGGG CCTAGTGGAA | 240 |
| CTGGTTGGCC TAGTGGAACT GGTTGGCCTA GTGAAGTTGG TTGGCCTAAT GAACCATTTG | 300 |
| GATATCACCT TCTTTGGT | 318 |

(2) INFORMATION FOR SEQ ID NO:58:

(i) SEQUENCE CHARACTERISTICS:
        (A) LENGTH: 358 base pairs
        (B) TYPE: nucleic acid
        (C) STRANDEDNESS: single
        (D) TOPOLOGY: linear (xi) SEQUENCE DESCRIPTION: SEQ ID NO:58:

| | |
|---|---|
| TTGCAGGTGA TACCGATCGC GAAGCTGGTG GGCCTAGTGG AACTGTTGGG CCTAGTGAAG | 60 |
| CTGGTGGGCC TAGTGAAGCT GGTGGGCCTA GTGAAGCTGG TGGGCCTAGT GAAGCTGGTG | 120 |
| GGCCTAGTGA AGCTGGTGGG CCTAGTGAAG CTGGTGGGCC TAGTGAAGCT GGTGGGCCTA | 180 |

```
GTGAAGCTGG TGGGCCTAGT GAAGCTGGTG GGCCTAGTGA AGCTGGTTGG CCTAGTGAAG        240

CTGGTTGGCC TAGTGAAGCT GGTGGGCCTA GTGGAACTGG TTGGCCTAGT GAAGCTGGTT        300

GGCCTAGTGA AGCTGGTTGG CCTAGTGAAG CTGGTTGGCC TAGTGAAGCT GGTTGGCC          358
```

(2) INFORMATION FOR SEQ ID NO:59:

(i) SEQUENCE CHARACTERISTICS:
        (A) LENGTH: 409 base pairs
        (B) TYPE: nucleic acid
        (C) STRANDEDNESS: single
        (D) TOPOLOGY: linear (xi) SEQUENCE DESCRIPTION: SEQ ID NO:59:

```
TGCAGGTGAT ACCGATCGCG AAGCTGGTGG GCCTAGTGGA ACTGTTGGGC CTAGTGAAGC         60

TGGTGGGCCT AGTGAAGCTG GTGGGCCTAG TGAAGCTGGT GGGCCTAGTG AAGCTGGTGG        120

GCCTAGTGAA GCTGGTGGGC CTAGTGAAGC TGGTGGGCCT AGTGAAGCTG GTGGGCCTAG        180

TGAAGCTGGT GGGCCTAGTG AAGCTGGTGG GCCTAGTGAA GCTGGTTGGC CTAGTGAAGC        240

TGGTTGGCCT AGTGAAGCTG GTGGGCCTAG TGGAACTGGT TGGCCTAGTG AAGCTGGTTG        300

GCCTAGTGAA GCTGGTTGGC CTAGTGAAGC TGGTTGGCCT AGTGAAGCTG GTTGGCCTAG        360

TGAACGATTT GGATATCAGC TTCTTTGGTA TTCTAGAAGA ATAGTTATA                   409
```

(2) INFORMATION FOR SEQ ID NO:60:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (xi) SEQUENCE DESCRIPTION: SEQ ID NO:60:

```
GTGAAGCTGG TGGGCCTAGT GGAACTGTTG GGCCTAGTGA AGCTGGTGGG CCTAGTGAAG         60

CTGGTGGGCC TAGTGAAGCT GGTGGGCCTA GTGAAGCTGG TGGGCCTAGT GAAGCTGGTG        120

GGCCTAGTGA AGCTGGTGGG CCTAGTGAAG CTGGTGGGCC TAGTGAAGCT GGTGGGCCTA        180

GTGAAGCTGG TGGGCCTAGT GAAGCTGGTT GGCCTAGTGA AGCTGGTTGG CCTAGTGAAG        240

CTGGTGGGCC TAGTGGAACT GGTTGGCCTA GTGAAGCTGG TTGGCCTAGT GAAGCTGGTT        300

GGCCTAGTGA AGCTGGTTGG CCTAGTGAAG CTGGTTGGCC TAGTGAACGA T                 351
```

(2) INFORMATION FOR SEQ ID NO:61:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (xi) SEQUENCE DESCRIPTION: SEQ ID NO:61:

```
AGGTGATACC GATCGCGAAG CTGGTGGGCC TAGTGGAACT GTTGGGCCTA GTGAAGCTGG         60

TGGGCCTAGT GAAGCTGGTG GGCCTAGTGA AGCTGGTGGG CCTAGTGAAG CTGGTGGGCC        120

TAGTGAAGCT GGTGGGCCTA GTGAAGCTGG TGGGCCTAGT GAAGCTGGTG GGCCTAGTGA        180

AGCTGGTGGG CCTAGTGAAG CTGGTGGGCC TAGTGAAGCT GGTGGGCCTA GTGAAGCTGG        240

TTGGCCTAGT GAAGCTGGTT GGCCTAGTGA AGCTGGTGGG CCTAGTGGAA CTGGTTGGCC        300

TAGTGAAGCT GGTTGGCCTA GTGAAGCTGG TTGGCCTAGT GAAGCTGGTT GGCCTAGTGA        360

AGCTGGTTGG CCTAGTGAAC GATTTGGATA TCAGCTTCTT TGGTATTCTA                  410
```

(2) INFORMATION FOR SEQ ID NO:62:

(i) SEQUENCE CHARACTERISTICS:
        (A) LENGTH: 416 base pairs
        (B) TYPE: nucleic acid
        (C) STRANDEDNESS: single
        (D) TOPOLOGY: linear (xi) SEQUENCE DESCRIPTION: SEQ ID NO:62:

```
TTGCAGGTGA TACCGATCGC GAAGCTGGTG GGCCTAGTGG AACTGTTGGG CCTAGTGAAG      60
CTGGTGGGCC TAGTGAAGCT GGTGGGCCTA GTGAAGCTGG TGGGCCTAGT GAAGCTGGTG     120
GGCCTAGTGA AGCTGGTGGG CCTAGTGAAG CTGGTGGGCC TAGTGAAGCT GGTGGGCCTA     180
GTGAAGCTGG TGGGCCTAGT GAAGCTGGTG GGCCTAGTGA AGCTGGTGGG CCTAGTGAAG     240
CTGGTGGGCC TAGTGAAGCT GGTTGGCCTA GTGAAGCTGG TTGGCCTAGT GAAGCTGGTG     300
GGCCTAGTGG AACTGGTTGG CCTAGTGAAG CTGGTTGGCC TAGTGAAGCT GGTTGGCCTA     360
GTGAAGCTGG TTGGCCTAGT GAAGCTGGTT GGCCTAGTGA ACGATTTGGA TATCAG        416
```

(2) INFORMATION FOR SEQ ID NO:63:

(i) SEQUENCE CHARACTERISTICS:
        (A) LENGTH: 356 base pairs
        (B) TYPE: nucleic acid
        (C) STRANDEDNESS: single
        (D) TOPOLOGY: linear (xi) SEQUENCE DESCRIPTION: SEQ ID NO:63:

```
TTGCAGGTGA TACCGATCGC GAAGCTGGTG GGCCTAGTGG AACTGTTGGG CCTAGTGAAG      60
CTGGTGGGCC TAGTGAAGCT GGTGGGCCTA GTGAAGCTGG TGGGCCTAGT GAAGCTGGTG     120
GGCCTAGTGA AGCTGGTGGG CCTAGTGAAG CTGGTGGGCC TAGTGAAGCT GGTGGGCCTA     180
GTGAAGCTGG TGGGCCTAGT GGAACTGGTT GGCCTAGTGA AGCTGGTTGG CCTAGTGAAG     240
CTGGTTGGCC TAGTGAAGCT GGTTGGCCTA GTGAAGCTGG TTGGCCTAGT GAAGCTGGTT     300
GGCCTAGTGA ACGATTTGGA TATCAGCTTC TTTGGTATTC TAGAAGAATA GTTATA        356
```

(2) INFORMATION FOR SEQ ID NO:64:

(i) SEQUENCE CHARACTERISTICS:
        (A) LENGTH: 285 base pairs
        (B) TYPE: nucleic acid
        (C) STRANDEDNESS: single
        (D) TOPOLOGY: linear (xi) SEQUENCE DESCRIPTION: SEQ ID NO:64:

```
TTGCAGGTGA TACCGATCGC GAAGCTGGTG GGCCTAGTGG AACTGTTGGG CCTAGTGAAG      60
CTGGTGGGCC TAGTGAAGCT GGTGGGCCTA GTGAAGCTGG TGGGCCTAGT GAAGCTGGTG     120
GGCCTAGTGA AGCTGGTGGG CCTAGTGAAG CTGGTGGGCC TAGTGAAGCT GGTGGGCCTA     180
GTGGAACTGG TTGGCCTAGT GAAGCTGGTT GGCCTAGTGA AGCTGGTTGG CCTAGTGAAG     240
CTGGTTGGCC TAGTGAAGCT GGTTGGCCTA GTGAAGCTGG TTGGC                    285
```

(2) INFORMATION FOR SEQ ID NO:65:

(i) SEQUENCE CHARACTERISTICS:
        (A) LENGTH: 342 base pairs
        (B) TYPE: nucleic acid
        (C) STRANDEDNESS: single
        (D) TOPOLOGY: linear (xi) SEQUENCE DESCRIPTION: SEQ ID NO:65:

TTGCAGGTGA TACCGATCGC GAAGCTGGTG GGCCTAGTGG AACTGTTGGG CCTAGTGAAG      60

CTGGTGGGCC TAGTGAAGCT GGTGGGCCTA GTGAAGCTGG TGGGCCTAGT GAAGCTGGTG     120

GGCCTAGTGA AGCTGGTGGG CCTAGTGAAG CTGGTGGGCC TAGTGAAGCT GGTGGGCCTA     180

GTGAAGCTGG TGGGCCTAGT GGAACTGGTT GGCCTAGTGA AGCTGGTTGG CCTAGTGAAG     240

CTGGTTGGCC TAGTGAAGCT GGTTGGCCTA GTGAAGCTGG TTGGCCTAGT GAAGCTGGTT     300

GGCCTAGTGA ACGATTTGGA TATCAGCTTC TTTGGTATTC TA                        342

(2) INFORMATION FOR SEQ ID NO:66:

(i) SEQUENCE CHARACTERISTICS:
          (A) LENGTH: 363 base pairs
          (B) TYPE: nucleic acid
          (C) STRANDEDNESS: single
          (D) TOPOLOGY: linear (xi) SEQUENCE DESCRIPTION: SEQ ID NO:66:

TTGCAGGTGA TACCGATCGC GAAGCTGGTG GGCCTAGTGG AACTGTTGGG CCTAGTGAAG      60

CTGGTGGGCC TAGTGAAGCT GGTGGGCCTA GTGAAGCTGG TGGGCCTAGT GAAGCTGGTG     120

GGCCTAGTGA AGCTGGTGGG CCTAGTGAAG CTGGTGGGCC TAGTGAAGCT GGTGGGCCTA     180

GTGAAGCTGG TGGGCCTAGT GAAGCTGGTG GGCCTAGTGG AACTGGTTGG CCTAGTGAAG     240

CTGGTTGGCC TAGTGAAGCT GGTTGGCCTA GTGAAGCTGG TTGGCCTAGT GAAGCTGGTT     300

GGCCTAGTGA AGCTGGTTGG CCTAGTGAAC GATTTGGATA TCAGCTTCTT TGGTATTCTA     360

GAA                                                                  363

(2) INFORMATION FOR SEQ ID NO:67:

(i) SEQUENCE CHARACTERISTICS:
          (A) LENGTH: 363 base pairs
          (B) TYPE: nucleic acid
          (C) STRANDEDNESS: single
          (D) TOPOLOGY: linear (xi) SEQUENCE DESCRIPTION: SEQ ID NO:67:

TTGCAGGTGA TACCGATCGC GAAGCTGGTG GGCCTAGTGG AACTGTTGGG CCTAGTGAAG      60

CTGGTGGGCC TAGTGAAGCT GGTGGGCCTA GTGAAGCTGG TGGGCCTAGT GAAGCTGGTG     120

GGCCTAGTGA AGCTGGTGGG CCTAGTGAAG CTGGTGGGCC TAGTGAAGCT GGTGGGCCTA     180

GTGAAGCTGG TGGGCCTAGT GAAGCTGGTG GGCCTAGTGG AACTGGTTGG CCTAGTGAAG     240

CTGGTTGGCC TAGTGAAGCT GGTTGGCCTA GTGAAGCTGG TTGGCCTAGT GAAGCTGGTT     300

GGCCTAGTGA AGCTGGTTGG CCTAGTGAAC GATTTGGATA TCAGCTTCTT TGGTATTCTA     360

GAA                                                                  363

(2) INFORMATION FOR SEQ ID NO:68:

(i) SEQUENCE CHARACTERISTICS:
          (A) LENGTH: 101 amino acids
          (B) TYPE: amino acid
          (C) STRANDEDNESS:
          (D) TOPOLOGY: linear (xi) SEQUENCE DESCRIPTION: SEQ ID NO:68:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Gly Thr

```
                        20                  25                  30

Val Gly Pro Ser Glu Ala Gly Gly Pro Ser Glu Ala Gly Gly Pro Ser
            35                  40                  45

Gly Thr Gly Trp Pro Ser Glu Ala Gly Gly Pro Ser Gly Thr Val Gly
        50                  55                  60

Pro Ser Glu Ala Gly Gly Pro Ser Glu Ala Gly Gly Pro Ser Gly Thr
65                  70                  75                  80

Gly Trp Pro Ser Gly Thr Gly Trp Pro Ser Glu Val Gly Trp Pro Ile
                85                  90                  95

Glu Pro Phe Gly Tyr
            100

(2) INFORMATION FOR SEQ ID NO:69:

(i) SEQUENCE CHARACTERISTICS:
        (A) LENGTH: 105 amino acids
        (B) TYPE: amino acid
        (C) STRANDEDNESS:
        (D) TOPOLOGY: linear (xi) SEQUENCE DESCRIPTION: SEQ ID NO:69:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Gly Thr
            20                  25                  30

Val Gly Pro Ser Glu Ala Gly Gly Pro Ser Glu Ala Gly Gly Pro Ser
            35                  40                  45

Gly Thr Gly Trp Pro Ser Glu Ala Gly Gly Pro Ser Gly Thr Val Gly
        50                  55                  60

Pro Ser Glu Ala Gly Gly Pro Ser Glu Ala Gly Gly Pro Ser Gly Thr
65                  70                  75                  80

Gly Trp Pro Ser Gly Thr Gly Trp Pro Ser Glu Val Gly Trp Pro Asn
                85                  90                  95

Glu Pro Phe Gly Tyr His Leu Leu Trp
            100                 105

(2) INFORMATION FOR SEQ ID NO:70:

(i) SEQUENCE CHARACTERISTICS:
        (A) LENGTH: 118 amino acids
        (B) TYPE: amino acid
        (C) STRANDEDNESS:
        (D) TOPOLOGY: linear (xi) SEQUENCE DESCRIPTION: SEQ ID NO:70:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
        50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
                85                  90                  95

Glu Ala Gly Trp Pro Ser Glu Ala Gly Trp Pro Ser Glu Ala Gly Trp
```

```
                   100                 105                 110
Pro Ser Glu Ala Gly Trp
            115

(2) INFORMATION FOR SEQ ID NO:71:

(i) SEQUENCE CHARACTERISTICS:
        (A) LENGTH: 136 amino acids
        (B) TYPE: amino acid
        (C) STRANDEDNESS:
        (D) TOPOLOGY: linear (xi) SEQUENCE DESCRIPTION: SEQ ID NO:71:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Glu Ala Gly Trp Pro Ser Glu Ala
65                  70                  75                  80

Gly Trp Pro Ser Glu Ala Gly Gly Pro Ser Gly Thr Gly Trp Pro Ser
            85                  90                  95

Glu Ala Gly Trp Pro Ser Glu Ala Gly Trp Pro Ser Glu Ala Gly Trp
            100                 105                 110

Pro Ser Glu Ala Gly Trp Pro Ser Glu Arg Phe Gly Tyr Gln Leu Leu
            115                 120                 125

Trp Tyr Ser Arg Arg Ile Val Ile
            130                 135

(2) INFORMATION FOR SEQ ID NO:72:

(i) SEQUENCE CHARACTERISTICS:
        (A) LENGTH: 116 amino acids
        (B) TYPE: amino acid
        (C) STRANDEDNESS:
        (D) TOPOLOGY: linear (xi) SEQUENCE DESCRIPTION: SEQ ID NO:72:

Glu Ala Gly Gly Pro Ser Gly Thr Val Gly Pro Ser Glu Ala Gly Gly
1               5                   10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Trp Pro Ser Glu Ala Gly Trp Pro Ser Glu Ala
65                  70                  75                  80

Gly Gly Pro Ser Gly Thr Gly Trp Pro Ser Glu Ala Gly Trp Pro Ser
            85                  90                  95

Glu Ala Gly Trp Pro Ser Glu Ala Gly Trp Pro Ser Glu Ala Gly Trp
            100                 105                 110

Pro Ser Glu Arg
            115
```

(2) INFORMATION FOR SEQ ID NO:73:

(i) SEQUENCE CHARACTERISTICS:
        (A) LENGTH: 136 amino acids
        (B) TYPE: amino acid
        (C) STRANDEDNESS:
        (D) TOPOLOGY: linear (xi) SEQUENCE DESCRIPTION: SEQ ID NO:73:

```
Gly Asp Thr Asp Arg Glu Ala Gly Gly Pro Ser Gly Thr Val Gly Pro
 1               5                  10                  15

Ser Glu Ala Gly Gly Pro Ser Glu Ala Gly Gly Pro Ser Glu Ala Gly
            20                  25                  30

Gly Pro Ser Glu Ala Gly Gly Pro Ser Glu Ala Gly Gly Pro Ser Glu
        35                  40                  45

Ala Gly Gly Pro Ser Glu Ala Gly Gly Pro Ser Glu Ala Gly Gly Pro
    50                  55                  60

Ser Glu Ala Gly Gly Pro Ser Glu Ala Gly Gly Pro Ser Glu Ala Gly
65                  70                  75                  80

Trp Pro Ser Glu Ala Gly Trp Pro Ser Glu Ala Gly Gly Pro Ser Gly
                85                  90                  95

Thr Gly Trp Pro Ser Glu Ala Gly Trp Pro Ser Glu Ala Gly Trp Pro
                100                 105                 110

Ser Glu Ala Gly Trp Pro Ser Glu Ala Gly Trp Pro Ser Glu Arg Phe
            115                 120                 125

Gly Tyr Gln Leu Leu Trp Tyr Ser
        130                 135
```

(2) INFORMATION FOR SEQ ID NO:74:

(i) SEQUENCE CHARACTERISTICS:
        (A) LENGTH: 138 amino acids
        (B) TYPE: amino acid
        (C) STRANDEDNESS:
        (D) TOPOLOGY: linear (xi) SEQUENCE DESCRIPTION: SEQ ID NO:74:

```
Ala Gly Asp Thr Asp Arg Glu Ala Gly Gly Pro Ser Gly Thr Val Gly
 1               5                  10                  15

Pro Ser Glu Ala Gly Gly Pro Ser Glu Ala Gly Gly Pro Ser Glu Ala
            20                  25                  30

Gly Gly Pro Ser Glu Ala Gly Gly Pro Ser Glu Ala Gly Gly Pro Ser
        35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Glu Ala Gly Gly Pro Ser Glu Ala
65                  70                  75                  80

Gly Gly Pro Ser Glu Ala Gly Trp Pro Ser Glu Ala Gly Trp Pro Ser
                85                  90                  95

Glu Ala Gly Gly Pro Ser Gly Thr Gly Trp Pro Ser Glu Ala Gly Trp
                100                 105                 110

Pro Ser Glu Ala Gly Trp Pro Ser Glu Ala Gly Trp Pro Ser Glu Ala
            115                 120                 125

Gly Trp Pro Ser Glu Arg Phe Gly Tyr Gln
        130                 135
```

(2) INFORMATION FOR SEQ ID NO:75:

(i) SEQUENCE CHARACTERISTICS:

(A) LENGTH: 118 amino acids
            (B) TYPE: amino acid
            (C) STRANDEDNESS:
            (D) TOPOLOGY: linear (xi) SEQUENCE DESCRIPTION: SEQ ID NO:75:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Glu Ala Gly Gly
        50                  55                  60

Pro Ser Gly Thr Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Arg Phe Gly Tyr Gln Leu Leu Trp Tyr
                100                 105                 110

Ser Arg Arg Ile Val Ile
            115

(2) INFORMATION FOR SEQ ID NO:76:

(i) SEQUENCE CHARACTERISTICS:
        (A) LENGTH: 94 amino acids
        (B) TYPE: amino acid
        (C) STRANDEDNESS:
        (D) TOPOLOGY: linear (xi) SEQUENCE DESCRIPTION: SEQ ID NO:76:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Glu Ala Gly Trp
        50                  55                  60

Pro Ser Glu Ala Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp
                85                  90

(2) INFORMATION FOR SEQ ID NO:77:

(i) SEQUENCE CHARACTERISTICS:
        (A) LENGTH: 113 amino acids
        (B) TYPE: amino acid
        (C) STRANDEDNESS:
        (D) TOPOLOGY: linear (xi) SEQUENCE DESCRIPTION: SEQ ID NO:77:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

```
Glu Ala Gly Gly Pro Ser Glu Ala Gly Gly Pro Ser Glu Ala Gly Gly
    50                  55                  60

Pro Ser Gly Thr Gly Trp Pro Ser Glu Ala Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Arg Phe Gly Tyr Gln Leu Leu Trp Tyr
                100                 105                 110

Ser (2) INFORMATION FOR SEQ ID NO:78:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:78:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Gly Thr Gly Trp Pro Ser Glu Ala
65                  70                  75                  80

Gly Trp Pro Ser Glu Ala Gly Trp Pro Ser Glu Ala Gly Trp Pro Ser
                85                  90                  95

Glu Ala Gly Trp Pro Ser Glu Ala Gly Trp Pro Ser Glu Arg Phe Gly
                100                 105                 110

Tyr Gln Leu Leu Trp Tyr Ser Arg
        115                 120

(2) INFORMATION FOR SEQ ID NO:79:

(i) SEQUENCE CHARACTERISTICS:
        (A) LENGTH: 120 amino acids
        (B) TYPE: amino acid
        (C) STRANDEDNESS:
        (D) TOPOLOGY: linear (xi) SEQUENCE DESCRIPTION: SEQ ID NO:79:

Ala Gly Asp Thr Asp Arg Glu Ala Gly Gly Pro Ser Gly Thr Val Gly
1               5                   10                  15

Pro Ser Glu Ala Gly Gly Pro Ser Glu Ala Gly Gly Pro Ser Glu Ala
                20                  25                  30

Gly Gly Pro Ser Glu Ala Gly Gly Pro Ser Glu Ala Gly Gly Pro Ser
            35                  40                  45

Glu Ala Gly Gly Pro Ser Glu Ala Gly Gly Pro Ser Glu Ala Gly Gly
    50                  55                  60

Pro Ser Glu Ala Gly Gly Pro Ser Gly Thr Gly Trp Pro Ser Glu Ala
65                  70                  75                  80

Gly Trp Pro Ser Glu Ala Gly Trp Pro Ser Glu Ala Gly Trp Pro Ser
                85                  90                  95
```

-continued

```
Glu Ala Gly Trp Pro Ser Glu Ala Gly Trp Pro Ser Glu Arg Phe Gly
            100                 105                 110
Tyr Gln Leu Leu Trp Tyr Ser Arg
            115             120
```

What is claimed is:

1. An isolated polypeptide comprising an immunogenic portion of a *B. microti* antigen, wherein said antigen comprises an amino acid sequence encoded by a DNA sequence of SEQ ID NO: 17.

2. A fusion protein comprising the polypeptide according to claim 1.

3. An isolated polypeptide comprising an amino acid sequence of SEQ ID NO: 32.

4. A fusion protein comprising the polypeptide of claim 3.

* * * * *